(12) United States Patent
Christensen et al.

(10) Patent No.: US 11,059,937 B2
(45) Date of Patent: Jul. 13, 2021

(54) EPOXY RESIN

(71) Applicants: THE BOEING COMPANY, Chicago, IL (US); Commonwealth Scientific and Industrial Research Organisation, Acton (AU)

(72) Inventors: Stephen Christensen, Sammamish, WA (US); Samuel Tucker, St Louis, MO (US); Jeffrey Wiggins, Petal, MS (US); Russell John Varley, Camberwell (AU); Nguyen Buu Dao, Doncaster East (AU); Wendy Wenjun Tian, Wheelers Hill (AU)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 16/320,403

(22) PCT Filed: Jul. 20, 2017

(86) PCT No.: PCT/AU2017/050748
§ 371 (c)(1),
(2) Date: Jan. 24, 2019

(87) PCT Pub. No.: WO2018/018070
PCT Pub. Date: Feb. 1, 2018

(65) Prior Publication Data
US 2019/0248953 A1    Aug. 15, 2019

Related U.S. Application Data

(60) Provisional application No. 62/366,443, filed on Jul. 25, 2016.

(30) Foreign Application Priority Data

Oct. 4, 2016   (AU) .............................. 2016904019

(51) Int. Cl.
C07D 407/14    (2006.01)
C08J 5/24    (2006.01)
(Continued)

(52) U.S. Cl.
CPC ....... C08G 59/3227 (2013.01); C07D 303/23 (2013.01); C07D 407/12 (2013.01);
(Continued)

(58) Field of Classification Search
CPC .. C07D 303/23; C07D 407/12; C07D 407/14; C08G 59/245; C08G 59/50;
(Continued)

(56) References Cited

U.S. PATENT DOCUMENTS 3,219,670 A * 11/1965 Smith .................. C08G 59/245
    549/560
4,649,181 A    3/1987 Darms et al.
(Continued)

FOREIGN PATENT DOCUMENTS

CN    104761874 A    7/2015
JP    62-114981 A    5/1987
(Continued)

OTHER PUBLICATIONS

International Search Report and Written Opinion—PCT/AU2017/050748—International Search Authority—Australian Patent Office—dated Aug. 11, 2017, 11 pages.
(Continued)

*Primary Examiner* — David T Karst
(74) *Attorney, Agent, or Firm* — Patterson + Sheridan, LLP

(57)    ABSTRACT

The present disclosure relates to epoxide containing compounds comprising three benzene units linked by bridging groups. The disclosure also relates to the production of curable epoxy resin formulations comprising said epoxide
(Continued)

containing compounds, and their possible incorporation into composite materials such as fibre reinforced composites. Possible methods for formulating the compounds epoxide containing compounds, as described herein, are also disclosed.

26 Claims, 26 Drawing Sheets

(51) Int. Cl.
    *C08G 59/24*     (2006.01)
    *C08J 5/04*     (2006.01)
    *C08K 5/14*     (2006.01)
    *C07D 303/23*     (2006.01)
    *C08G 59/50*     (2006.01)
    *C07D 407/12*     (2006.01)
    *C08K 5/00*     (2006.01)
    *C08G 59/32*     (2006.01)

(52) U.S. Cl.
    CPC ......... *C07D 407/14* (2013.01); *C08G 59/245* (2013.01); *C08G 59/50* (2013.01); *C08G 59/504* (2013.01); *C08G 59/5033* (2013.01); *C08J 5/04* (2013.01); *C08J 5/24* (2013.01); *C08K 5/14* (2013.01); *C08J 2363/00* (2013.01); *C08J 2363/02* (2013.01); *C08K 5/0025* (2013.01)

(58) Field of Classification Search
    CPC .............. C08G 59/5033; C08G 59/504; C08G 59/3227; C08J 5/04; C08J 5/24; C08J 2363/00; C08J 2363/02; C08K 5/14; C08K 5/0025
    USPC .......................................................... 528/87
    See application file for complete search history.

(56) References Cited

U.S. PATENT DOCUMENTS

| | | |
|---|---|---|
| 2015/0045505 A1 | 2/2015 | Christensen et al. |
| 2016/0152785 A1* | 6/2016 | Ueno ..................... B32B 27/26 523/468 |

FOREIGN PATENT DOCUMENTS

| | | |
|---|---|---|
| JP | H0820628 A | 1/1996 |
| JP | 5320384 B2 | 10/2013 |
| WO | 2007/102766 A1 | 9/2007 |

OTHER PUBLICATIONS

European Search Report for Application No. 17833085.8-1110/3487 dated May 12, 2020.
Japanese Examiners Decision of Final Refusal for Application No. 2019-503437 dated Dec. 1, 2020.
Leyong Wang, Haitao Xi, Xiaoqiang Sun, Yingzhong Shen, Yaang Yang, Yi Pan and Hongwen Hu, "Synthesis of Functionalized p-Phenylene Oxide Oligomers." Synthetic Communications, USA, vol. 30, No. 2, 2000, pp. 227-234.

* cited by examiner a)

b)

a)

b)

EPOXY RESIN

CROSS-REFERENCE TO RELATED APPLICATIONS

The present application is the national stage application of International Application No PCT/AU2017/050748 filed Jul. 20, 2017, which claims priority from U.S. Provisional Patent Application No. 62/366,443 filed on 25 Jul. 2016 and Australian Provisional Patent Application No 2016904019 filed on 4 Oct. 2016, the contents of which are incorporated herein by reference.

TECHNICAL FIELD

Disclosed herein are: epoxide containing compounds comprising three benzene units linked by bridging atoms; the production of curable epoxy resin formulations comprising said epoxide containing compounds; and the possible incorporation of the compounds into composite materials.

BACKGROUND ART

For fibre reinforced composites, efficiency of load transfer between fibres and the surrounding matrix on the micro-scale directly affects the overall mechanical performance of the composite at the continuum level. The region of the matrix that can be substantially affected by the presence of fibres, sometimes referred to as the "inter-phase" region, is the interfacial area of the matrix directly surrounding the fibre. In composites, it is this inter-phase region that experiences high shear strain due to the mismatch in elastic stiffness between the fibres and the surrounding matrix.

While various resin matrix formulations have been developed to maximize the distortional capability of a polymer resin, formulations demonstrating higher performance potential still have limitations such as limited fluid resistance and less than desired pre-impregnated composite material (prepreg) handling characteristics such as insufficient tack and/or prepreg handling life. These problems can be partially addressed by modifying the chemistry of the bulk polymer resin forming the matrix. However these modifications require development of specialized monomers or additives which may add to production cost. Moreover, while these specialized formulations and additives can improve fluid resistance of the matrix resin, they can reduce other performance properties of the composite.

Epoxies may deform by dilatational and/or distortional deformation. Materials that respond primarily with distortional deformation, as opposed to dilatational deformation, tend to show high strength and improved properties in comparison to materials that rely on dilatational deformation. Herein, the present inventors have undertaken extensive research and development to identify alternative types of epoxy resins that display enhanced distortional deformation, whilst displaying appropriate matrix modulus, glass transition temperature (Tg) and environmental resistance, characteristics.

Epoxy resins are versatile materials which can be combined with fibres to produce a variety of composite materials, including a raft of prepreg compositions.

For composite materials comprising an epoxy resin and fibres, the angle of the fibres influences the distribution of distortional vs. dilatational deformation. Therefore the angle of the incorporated fibres is selected in order to absorb mechanical energy and create an environment of distortional deformation rather than dilatational deformation. As the angle approaches parallel with a major loading direction the mode of deformation decreases in the form of dilatational deformation and increases in the form of distortional deformation. Finding the optimum angle for the fibres allows an increase in the loading carried by the fibres in these composite materials.

Whilst dilation deformation characteristics are generally similar amongst various epoxies, intramolecular torsional conformational arrangements within the components of epoxies means that distortional deformation properties can be markedly different for the various epoxy resins.

As distortional deformation is generally preferred, a challenge is to identify materials which possess optimal distortional attributes, whist balancing said distortional attributes with characteristics of the materials such as Tg and stiffness.

Accordingly, there is a need to develop and identify alternative types of epoxy resins that display enhanced distortional behaviour, while maintaining high performance properties. The distortional epoxy resins can then be combined with fibres to produce composite materials which absorb mechanical energy and dissipate this energy as heat, forestalling potential dilatational fractures and allowing increased loads to be carried by the fibres.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

In one aspect, disclosed herein is a compound of Formula 1 or Formula 2:

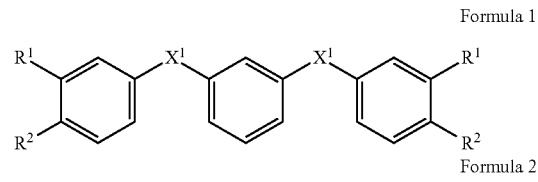

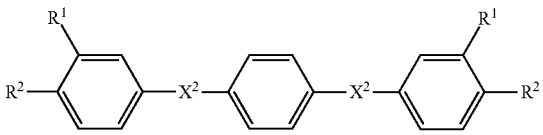

wherein:
each $X^1$ is the same and is selected from O and C(O);
each $X^2$ is the same and is selected from C(O); and
each $R^1$ is hydrogen and each $R^2$ is selected from an epoxide group, or each $R^2$ is hydrogen and each $R^1$ is selected from an epoxide group.

In one example, the epoxide group is selected from:

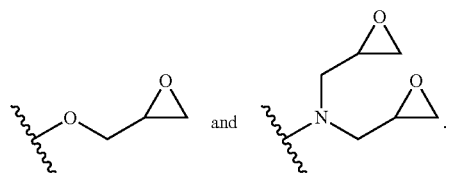 [SMILES: *OCC1CO1 ; *N(CC1CO1)CC1CO1]

In another example:
(a) when $X^1$ is O the epoxide group is

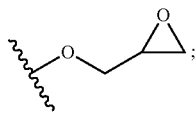 [SMILES: *OCC1CO1]

(b) when $X^1$ is C(O) the epoxide group is;

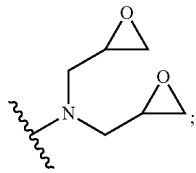 [SMILES: *N(CC1CO1)CC1CO1]

and
(c) when $X^2$ is C(O) either:
(i) $R^2$ is H and $R^1$ is

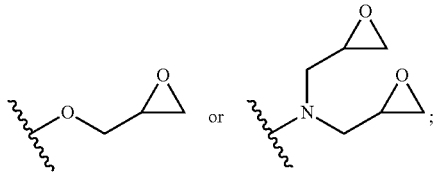 [SMILES: *OCC1CO1 ; *N(CC1CO1)CC1CO1]

or
(ii) $R^1$ is H and $R^2$ is

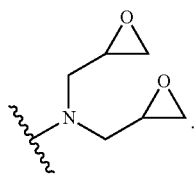 [SMILES: *N(CC1CO1)CC1CO1]

In another aspect, disclosed herein is a curable epoxy resin formulation comprising an epoxide comprising a compound as defined herein and a curing agent.

In another aspect, disclosed herein is a curable epoxy resin formulation comprising an epoxy resin and a curing agent wherein:
the epoxy resin comprises a compound of Formula 3:

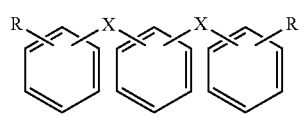

Formula 3 wherein
each X is the same and is selected from O, $CH_2$ and C(O);
each R is the same and is an epoxide group; and
the curing agent comprises a diamine curing agent of Formula 4:

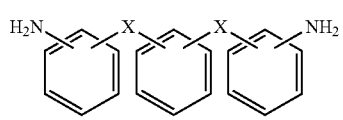

Formula 4 wherein each Y is the same and is selected from O, $CH_2$ and C(O).

In one example, the epoxide group is selected from:

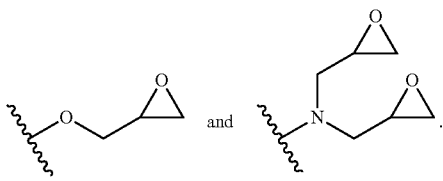 [SMILES: *OCC1CO1 ; *N(CC1CO1)CC1CO1]

In another example, each R is the same and is an epoxide group selected from the group consisting of:

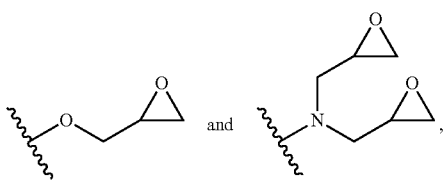

and optionally when R is

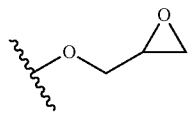 [SMILES: *OCC1CO1]

and X is $CH_2$, the $CH_2$ groups are meta with respect to one another.

In another aspect, disclosed herein is an impregnated fibre reinforced material comprising fibres impregnated with a curable epoxy resin formulation as defined herein.

In another aspect, disclosed herein is a composite material comprising a fibrous material in a matrix of a cured epoxy resin, wherein the cured epoxy resin is formed from a curable epoxy resin formulation as defined herein.

In another aspect, disclosed herein is a method of forming an impregnated fibre reinforced material, the method comprising the steps of:
a) providing:
  (i) a curable epoxy resin formulation as defined herein; and
  (ii) a fibrous material; and
b) combining the resin formulation of step (a)(i) with the fibrous material of step (a)(ii) and subjecting the material to an elevated temperature capable of curing to form the impregnated fibre reinforced material.

In another aspect, disclosed herein is use of a compound as defined herein as a curable epoxy resin or in the preparation of a curable epoxy resin formulation.

In another aspect, disclosed herein is a process for preparing a compound of Formula 8 comprising the steps of:

i) reacting together a compound of Formula 5 with a compound of Formula 6 in the presence of a catalyst to form a compound of Formula 7, wherein P is a protecting group, M is a metal and LG is a leaving group:

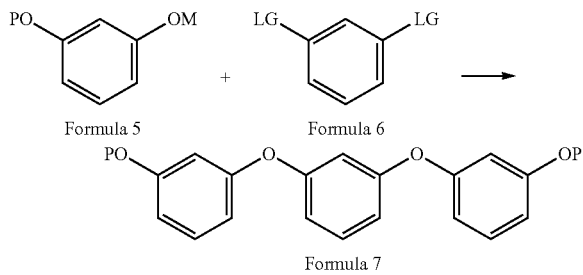

Formula 5  Formula 6

Formula 7 ii) further reacting the compound of Formula 7 with an acid catalyst to form a compound of Formula 8:

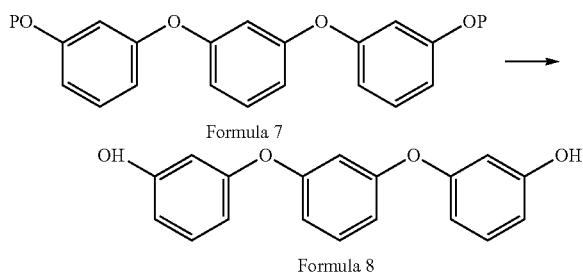

Formula 7

Formula 8

In another aspect, disclosed herein is a process for preparing a compound of Formula 10 comprising a step of reacting a compound of Formula 8 with a halogenated epoxy compound of Formula 9 to form the compound of Formula 10:

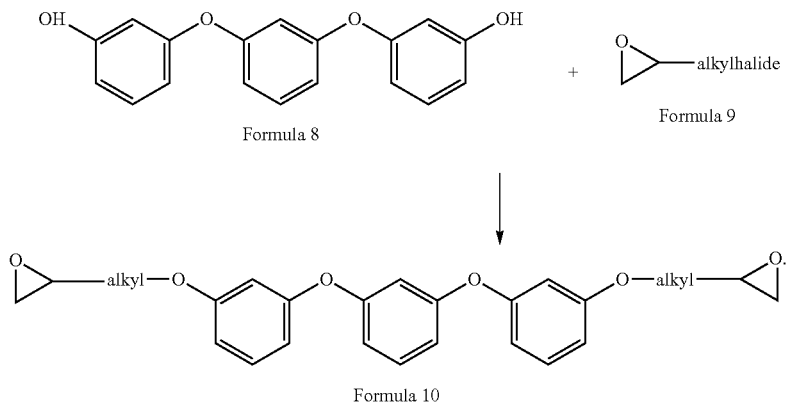

Formula 8

Formula 9

Formula 10

In one example, a compound of Formula 8 is prepared by a process according to the above-aspect.

BRIEF DESCRIPTION OF DRAWINGS

Whilst it will be appreciated that a variety of examples of the disclosure may be utilised, in the following we describe a number of examples with reference to the following drawings.

DETAILED DESCRIPTION

Figure 1:
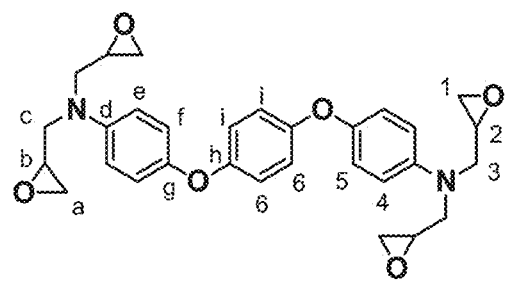
FIG. 1—$^1$H (image a)) and $^{13}$C (image b)) nuclear magnetic resonance spectra for N,N,N,N-tetraglycidyl 1,4-bis(4-aminophenoxy)benzene (144-TGAPB).
Figure 1:
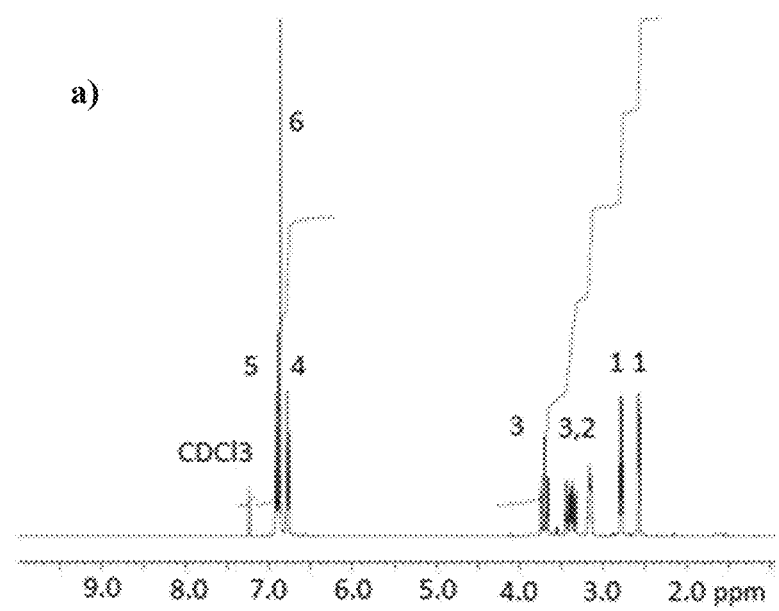
Figure 1:
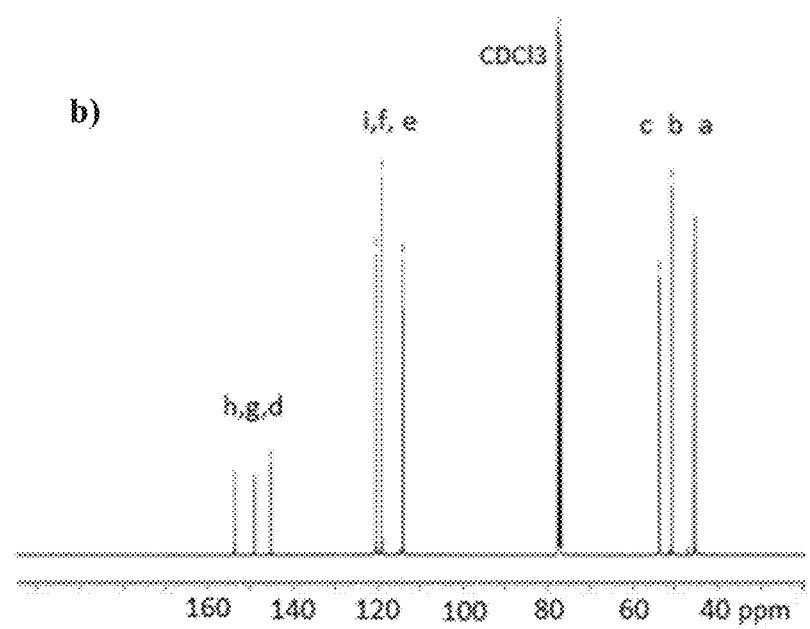

In the present disclosure curable epoxy resin formulations have been developed that include compounds comprising three aromatic rings linked together via ether, carbonyl or methylene groups, and end capped by two or four epoxide groups. The aromatic structures provide strength, and the ether, carbonyl or methylene bridging groups allow for torsional rotation to dissipate any mechanical energy and increase the distortional ability of cured epoxy resins. In addition, epoxide groups incorporated in the herein defined compounds, enable crosslinking into a polymer network structure.

The curable epoxy resins and formulations thereof, as described herein, have been developed for the possible production of composite materials. An aim of the present disclosure is to develop curable epoxy resin formulations with increased distortional properties to improve the performance of composite materials.

The compounds, composites, methods and uses defined herein will now be described more fully hereafter.

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular examples, and are not intended to limit the claims, because the scope is limited only by the claims. Furthermore, unless otherwise required by context, singular terms shall include pluralities and plural terms shall include the singular.

Throughout the present specification, various aspects and components of the invention can be presented in a range format. The range format is included for convenience and should not be interpreted as an inflexible limitation on the scope of the disclosure. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial (except where integers are required), numbers within the recited range, for example, 1, 2, 3, 4, 5, 5.5 and 6. This applies regardless of the breadth of the disclosed range. Where specific values are required, these will be indicated in the specification.

Terms

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term "consisting essentially of" is intended to exclude elements which would materially affect the properties of the claimed composition, although may include elements that do not materially affect properties.

Epoxide Containing Compounds

Disclosed herein are compounds of Formula 1:

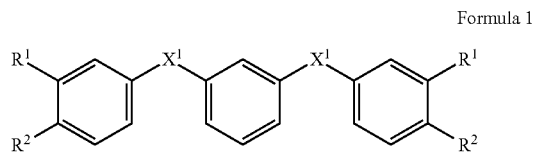

Formula 1 wherein:
each $X^1$ is the same and is selected from O, $CH_2$ and C(O); and each $R^1$ is hydrogen and each $R^2$ is selected from an epoxide group, or each $R^2$ is hydrogen and each $R^1$ is selected from an epoxide group.

Also disclosed herein are compounds of Formula 2:

Formula 2

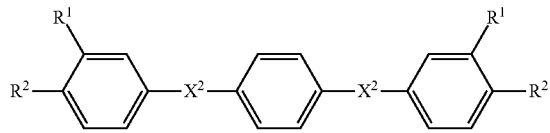

wherein:
each $X^2$ is the same and is selected from O, $CH_2$ and C(O); and
each $R^1$ is hydrogen and each $R^2$ is selected from an epoxide group, or each $R^2$ is hydrogen and each $R^1$ is selected from an epoxide group.

Also disclosed herein are compounds of Formula 1a:

Formula 1a

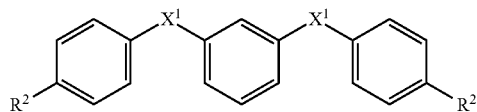

wherein:
each $X^1$ is the same and is selected from O, $CH_2$ and C(O); and
each $R^2$ is selected from an epoxide group.

Also disclosed herein are compounds of Formula 1b:

Formula 1b

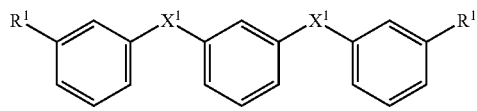

wherein:
each $X^1$ is the same and is selected from O, $CH_2$ and C(O); and
each $R^1$ is selected from an epoxide group.

Also disclosed herein are compounds of Formula 2a:

Formula 2a

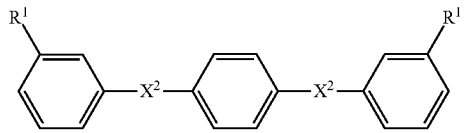

wherein:
each $X^2$ is the same and is selected from O, $CH_2$ and C(O); and
each $R^1$ is selected from an epoxide group.

Disclosed herein are compounds of Formula 2b:

Formula 2b

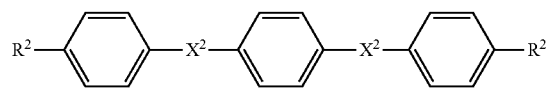

wherein:
each $X^2$ is the same and is selected from O, $CH_2$ and C(O); and
each $R^2$ is selected from an epoxide group.

Substituents $X^1$, $X^2$, $R^1$ and $R^2$

In any compound of Formula 1, 1a or 1b, $X^1$ can be O, $CH_2$ or C(O).

In one example $X^1$ is O. In another example $X^1$ is C(O). In another example $X^1$ is $CH_2$.

In any compound of Formula 2, 2a or 2b, $X^2$ can be O, $CH_2$ or C(O).

In one example $X^2$ is O. In another example $X^2$ is C(O). In another example $X^2$ is $CH_2$.

In another example each $X^1$ is the same and is selected from O and C(O); and each $X^2$ is the same and is selected from C(O).

In any compound of Formula 1 1b, 2 or 2a, $R^1$ can be hydrogen or an epoxide group.

In any compound of Formula 1, 1a, 2 or 2b, $R^2$ can be hydrogen or an epoxide group.

In one example each $R^1$ is hydrogen and each $R^2$ is selected from an epoxide group.

In one example each $R^2$ is hydrogen and each $R^1$ is selected from an epoxide group.

Epoxide Group

For compounds of Formula 1, 1a or 1b, the epoxide group can be selected from:

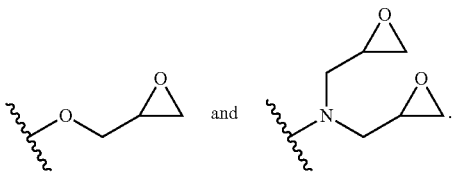 [SMILES: *OCC1CO1 ; *N(CC1CO1)CC1CO1]

For compounds of Formula 2, 2a or 2b, the epoxide group can be selected from:

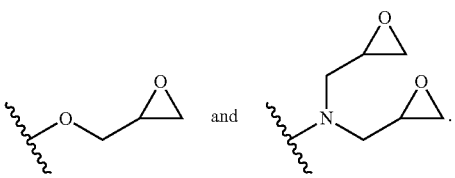 [SMILES: *OCC1CO1 ; *N(CC1CO1)CC1CO1]

In one example $R^1$ is

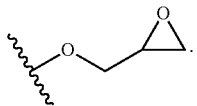

In another example $R^1$ is

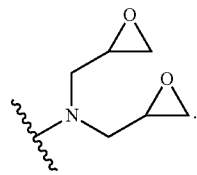 [SMILES: *N(CC1CO1)CC1CO1]

In one example $R^2$ is

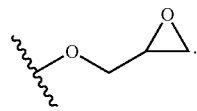 [SMILES: *OCC1CO1]

In yet another example $R^2$ is

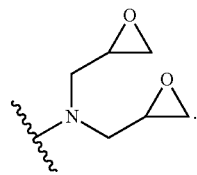 [SMILES: *N(CC1CO1)CC1CO1]

In one example, when $X^1$ is O the epoxide group is

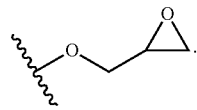 [SMILES: *OCC1CO1]

In another example, when $X^1$ is O the epoxide group is

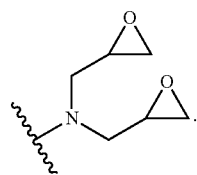 [SMILES: *N(CC1CO1)CC1CO1]

In one example, when $X^2$ is O the epoxide group is

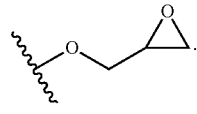 [SMILES: *OCC1CO1]

In another example, when $X^2$ is O the epoxide group is

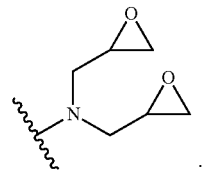

In one example, when $X^1$ is $CH_2$ the epoxide group is

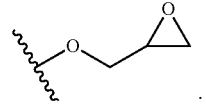 [SMILES: *OCC1CO1]

In another example, when $X^1$ is $CH_2$ the epoxide group is

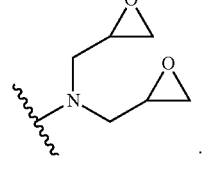

In one example, when $X^2$ is $CH_2$ the epoxide group is

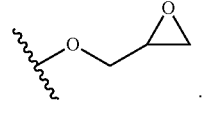 [SMILES: *OCC1CO1]

In another example, when $X^2$ is $CH_2$ the epoxide group is

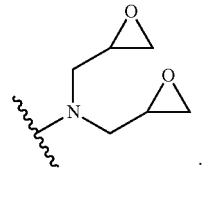 [SMILES: *N(CC1CO1)CC1CO1]

In one example, when $X^1$ is C(O) the epoxide group is

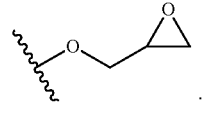 [SMILES: *OCC1CO1]

In another example, when $X^1$ is C(O) the epoxide group is

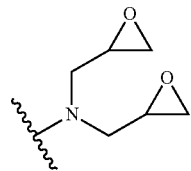

In one example, when $X^2$ is C(O) the epoxide group is

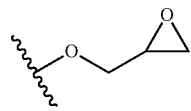

In another example, when $X^2$ is C(O) the epoxide group is

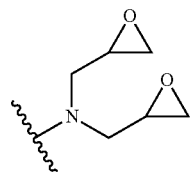

In an example, the compound of Formula 1 or Formula 2 can be selected from any one of:

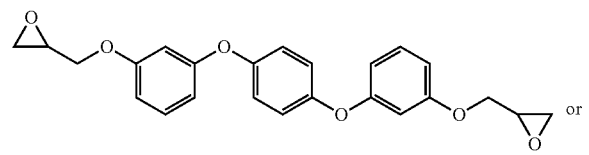 or

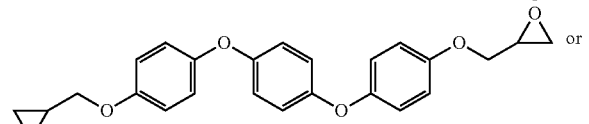 or

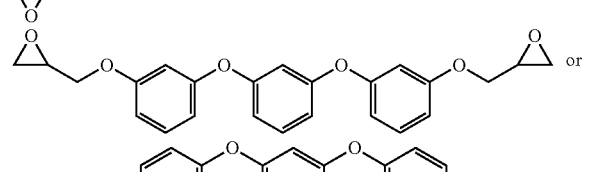 or

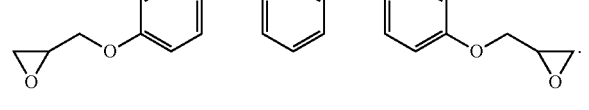.

In an example the compound of Formula 1 or Formula 2 can be selected from any one of:

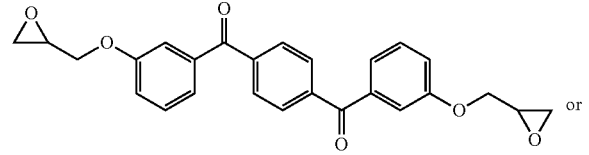 or

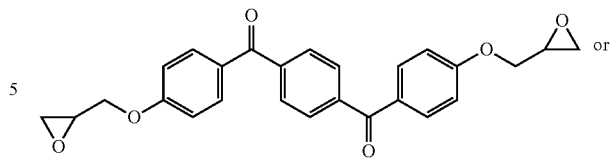 or

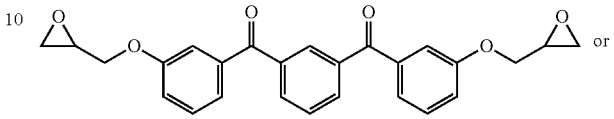 or

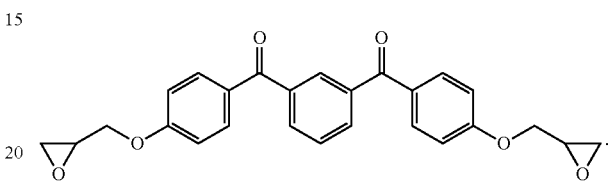.

In an example the compound of Formula 1 or Formula 2 can be selected from any one of:

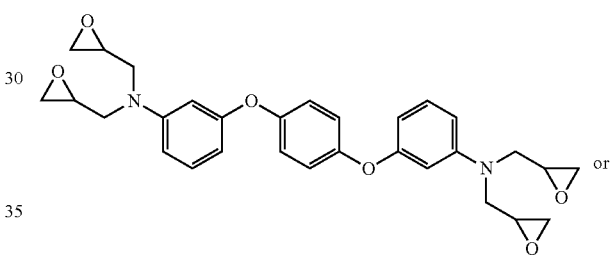 or

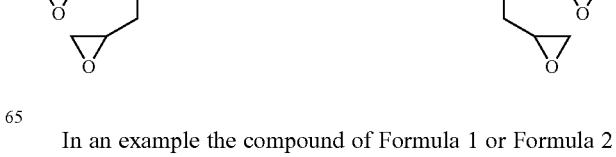.

In an example the compound of Formula 1 or Formula 2 can be selected from any one of:

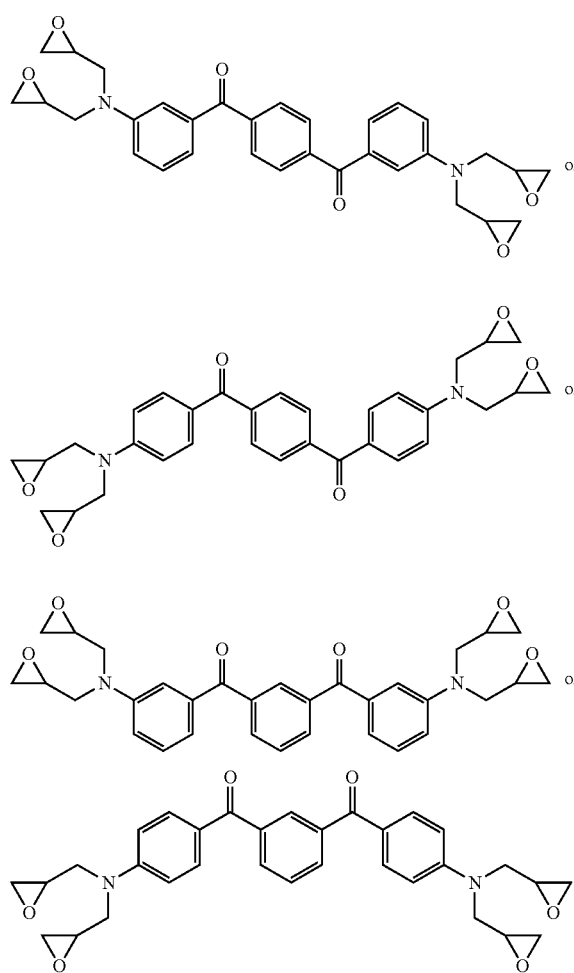

In an example the compound of Formula 1 or Formula 2 can be selected from an one of:

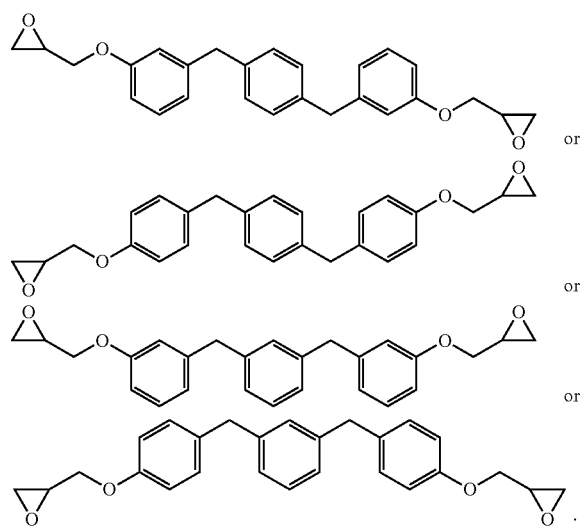

In an example the compound of Formula 1 or Formula 2 can be selected from any one of:

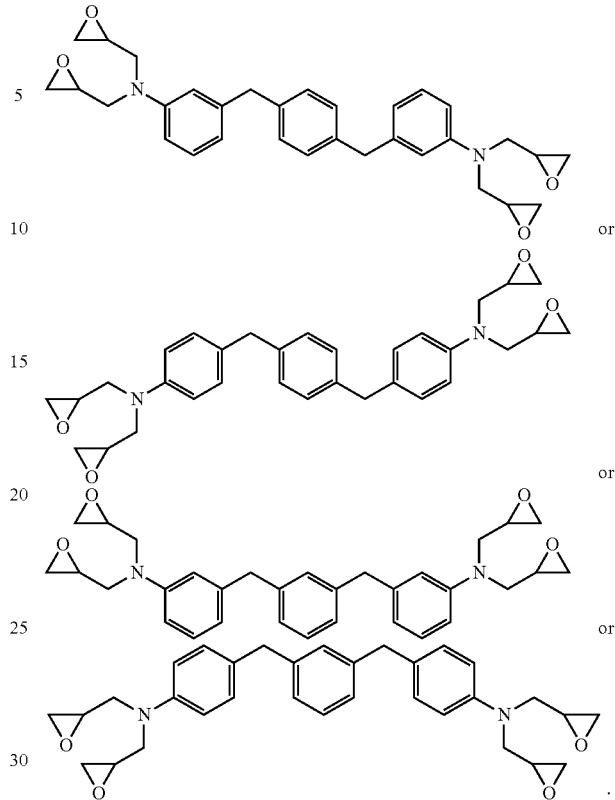

Curable Epoxy Resin Formulations

Disclosed herein are curable epoxy resin formulations comprising a compound of Formula 1, 1a, 1b, 2, 2a, or 2b, or a mixture thereof.

Disclosed herein are curable epoxy resin formulations comprising a compound of Formula 1, 1a, 1b, 2, 2a, or 2b, or a mixture thereof, and a curing agent.

Also disclosed herein are curable epoxy resin formulations consisting of or consisting essentially of a compound of any one of Formula 1, 1a, 1b, 2, 2a, or 2b, or a mixture thereof, and a curing agent.

In one example the curable epoxy resin formulation comprises a compound of Formula 1.

In one example the curable epoxy resin formulation comprises a compound of Formula 2.

Disclosed herein are curable epoxy resin formulations comprising an epoxy resin and a curing agent wherein:

the epoxy resin comprises a compound of Formula 3:

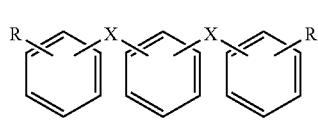

Formula 3 wherein:
each X is the same and is selected from O, CH$_2$ and C(O); and
each R is the same and is an epoxide group.

Disclosed herein are curable epoxy resin formulations consisting essentially of an epoxy resin and a curing agent wherein:

the epoxy resin comprises a compound of Formula 3:

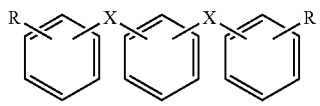
Formula 3 wherein:
each X is the same and is selected from O, CH$_2$ and C(O); and
each R is the same and is an epoxide group.

Disclosed herein are curable epoxy resin formulations comprising an epoxy resin and a curing agent wherein:
the epoxy resin comprises a compound of Formula 3:

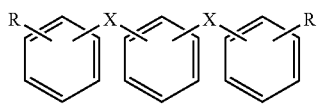
Formula 3 wherein:
each X is the same and is selected from O, CH$_2$ and C(O);
each R is the same and is an epoxide group; and
the curing agent comprises a diamine curing agent of Formula 4:

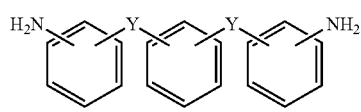
Formula 4 wherein each Y is the same and is selected from O, CH$_2$ and C(O).

Disclosed herein are curable epoxy resin formulations consisting of or consisting essentially of an epoxy resin and a curing agent, wherein:
the epoxy resin comprises a compound of Formula 3:

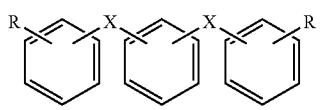
Formula 3 wherein:
each X is the same and is selected from O, CH$_2$ and C(O);
each R is the same and is an epoxide group; and
the curing agent comprises a diamine curing agent of Formula 4:

Formula 4 wherein each Y is the same and is selected from O, CH$_2$ and C(O).

In Formula 3, the two X substituents can be connected to the central benzene ring in the ortho, meta or para positions with respect to one another. In one example the two X substituents are in the 1 and 2 positions on the central benzene ring (ortho substitution). In another example the two X substituents are in the 1 and 3 positions on the central benzene ring (meta substitution). In yet another example the two X substituents are in the 1 and 4 positions on the central benzene ring (para substitution).

Herein the compound of Formula 3 can be a compound of Formula 3a:

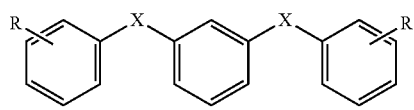
Formula 3a wherein:
each X is the same and is selected from O, CH$_2$ and C(O); and
each R is the same and is an epoxide group.

Herein the compound of Formula 3 can be a compound of Formula 3a-i:

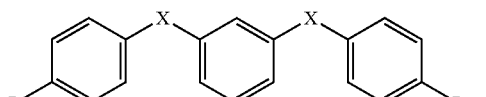
Formula 3a-i wherein:
each X is the same and is selected from O, CH$_2$ and C(O); and
each R is the same and is an epoxide group.

Herein the compound of Formula 3 can be a compound of Formula 3a-ii:

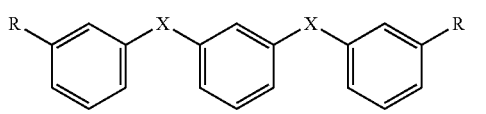
Formula 3a-ii wherein:
each X is the same and is selected from O, CH$_2$ and C(O); and
each R is the same and is an epoxide group.

Herein the compound of Formula 3 can be a compound of Formula 3b:

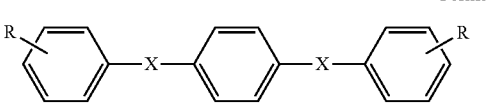
Formula 3b wherein:
  each X is the same and is selected from O, CH$_2$ and C(O); and
  each R is the same and is an epoxide group.

Herein the compound of Formula 3 can be a compound of Formula 3b-i:

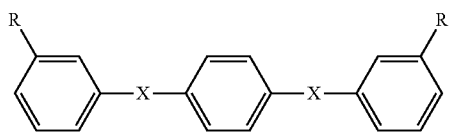

Formula 3b-i wherein:
  each X is the same and is selected from O, CH$_2$ and C(O); and
  each R is the same and is an epoxide group.

Herein the compound of Formula 3 can be a compound of Formula 3b-ii:

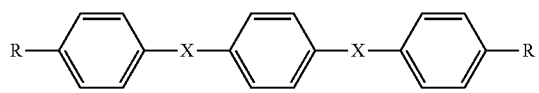

Formula 3b-ii wherein:
  each X is the same and is selected from O, CH$_2$ and C(O); and
  each R is the same and is an epoxide group.

In an example for any one of the above curable epoxy resin formulations, the epoxy resin can consist of or consist essentially of a compound of Formula 3 or any example thereof as described herein, and optionally a curing agent.

In another example for any of the above curable epoxy resin formulations, the curing agent present in the curable epoxy resin formulation can consist of, or consist essentially of, a diamine curing agent of Formula 4 or any example thereof as described herein.

The compound of Formula 3 can be selected from a compound of Formula 1 as defined herein. Alternatively, the compound of Formula 3 can be selected from a compound of Formula 1a or Formula 1b as defined herein.

The compound of Formula 3 can be selected from a compound of Formula 2 as defined herein. Alternatively, the compound of Formula 3 can be selected from a compound of Formula 2a or Formula 2b, as defined herein.

The compound of Formula 3 can be selected from a compound of Formula 3a as defined herein. Alternatively, the compound of Formula 3 can be selected from a compound of Formula 3a-i or Formula 3a-ii, as defined herein.

The compound of Formula 3 can be selected from a compound of Formula 3b as defined herein. Alternatively, the compound of Formula 3 can be selected from a compound of Formula 3b-i or Formula 3b-ii, as defined herein.

Substituents R and X

For a compound of Formula 3, X can be O, CH$_2$ or C(O).

In one example X is O. In another example X is C(O). In yet another example X is CH$_2$.

In a compound of Formula 3, each R group can be an epoxide group selected from:

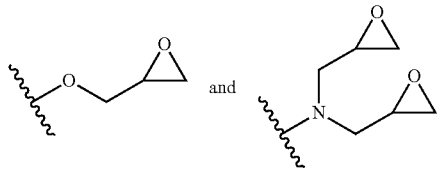

and

In one example substituent R in a compound of Formula 3 is

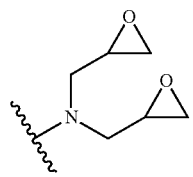

In one example substituent R in a compound of Formula 3 is

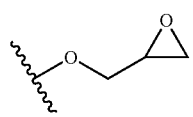

In one example when X is O, substituent R is

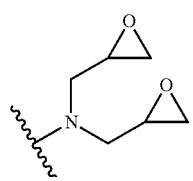

In another example when X is O, substituent R is

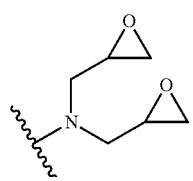

In one example when X is CH$_2$, substituent R is

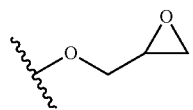

In another example when X is CH$_2$, substituent R is

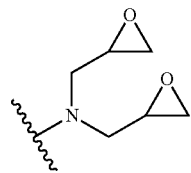

In one example when X is C(O), substituent R is

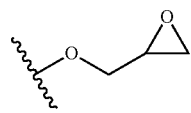

In another example when X is C(O), substituent R is

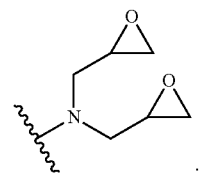 [SMILES: *N(CC1CO1)CC1CO1]

In one example the compound of Formula 3 can be selected from any one of:

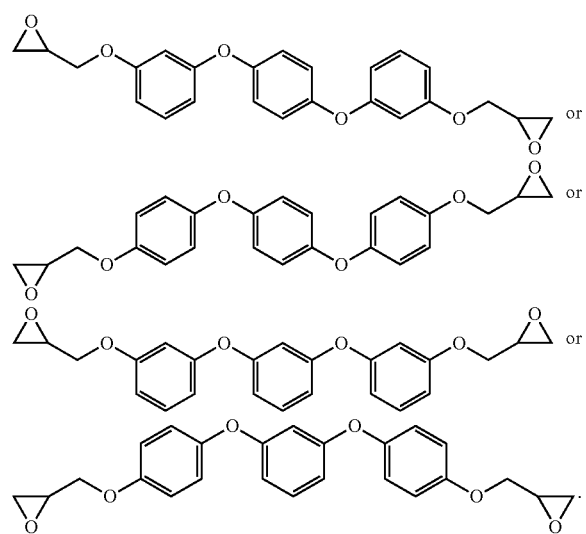

In one example the compound of Formula 3 can be selected from any one of:

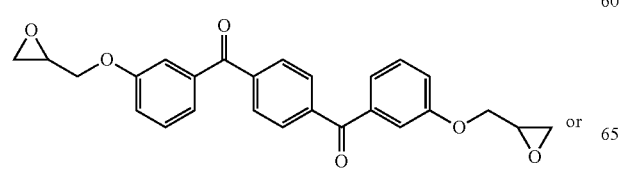

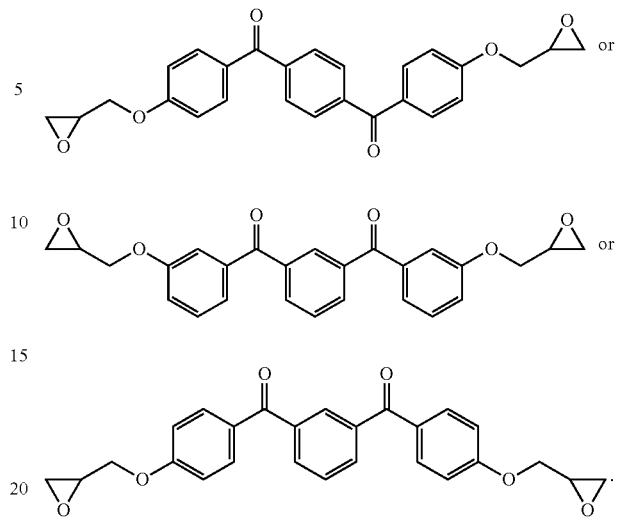

In one example the compound of Formula 3 can be selected from any one of:

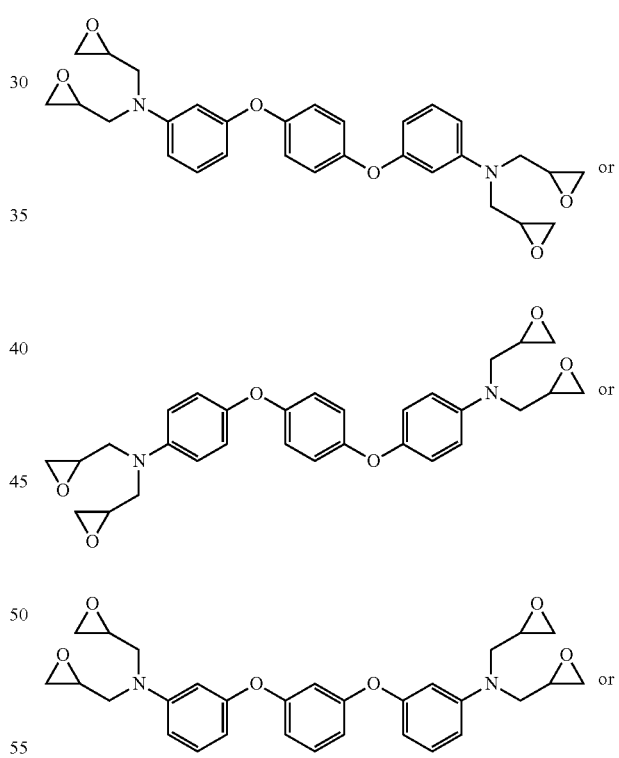

In one example the compound of Formula 3 can be selected from any one of:

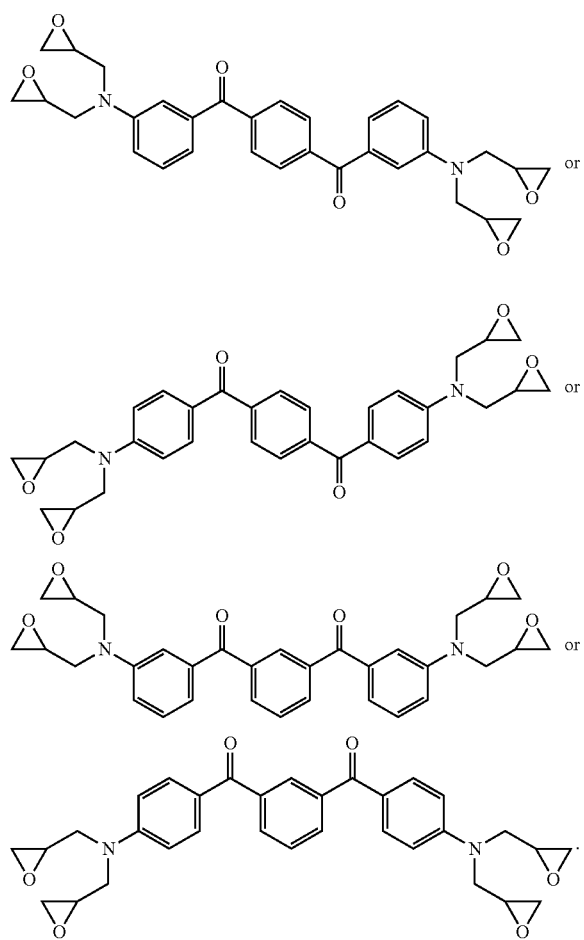

In one example the compound of Formula 3 can be selected from any one of:

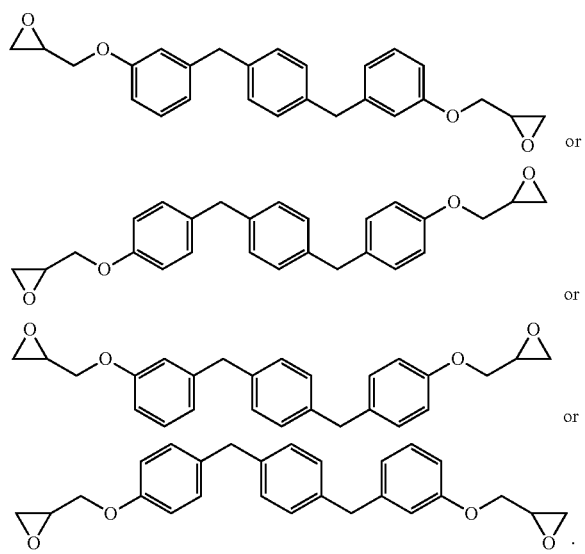

In one example the compound of Formula 3 can be selected from any one of:

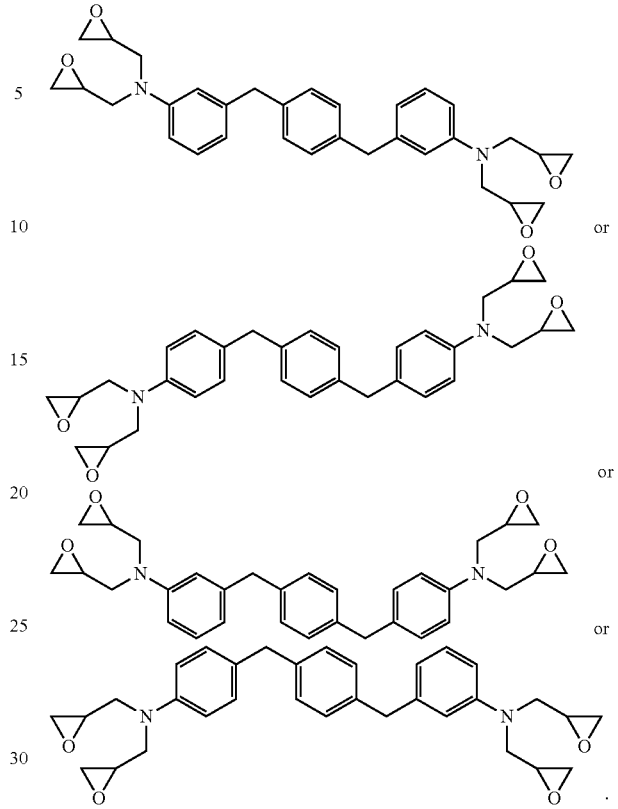

Curing Agents

Curing agents, such as amines, imidazoles, anhydrides, phenols and mercaptans, are known to those skilled in the art, and can be used in the compositions described herein.

Herein, the ratio of a curing agent and a compound of Formula 1, Formula 2 or Formula 3, can vary from a balanced stoichiometry of about 1.0:1.0 to a stoichiometry of about 0.6:1.0. For example, the ratio of a curing agent and a compound of Formula 1, Formula 2 or Formula 3 can be about 1.0:1.0, about 0.95:1.0, about 0.90:1.0, about 0.85:1.0, about 0.75:1.0, about 0.70:1.0, about 0.65:1.0, or about 0.6:1.0. In one example the ratio is 0.7:1.0.

For the curable epoxy resin formulations disclosed herein, the curing agent can be an amine.

In one example the curing agent is an aliphatic amine, cycloaliphatic amine, or an aromatic amine. Examples of possible amine curing agents include, but are not limited to: N-aminoethylpiperazine, menthanediamine, isophoronediamine, m-xylenediamine, metaphenylene diamine, diaminodiphenylmethane, diaminodiphenylsulfone, 3,3'-sulfonyldianiline, 4,4'-sulfonyldianiline, 4,4'-methylenedianiline, 4,4'-oxydianiline, 4,4'-methylenebis(2-ethylaniline), 3,3'-((2,2-dimethylpropane-1,3-diyl)bis(oxy))dianiline, 4,4'-(1,4-phenylenebis-(propane-2,2-diyl))dianiline, 3-(4-(4-aminobenzyl)-benzyl)aniline, 4,4'-(1,4-phenylenebis(propane-2,2-diyl))bis(2,6-dimethylaniline), 4,4'-(1,4-phenylenebis (oxy))-dianiline, 3,3'-((propane-2,2-diylbis-(4,1 phenylene)) bis(oxy))-dianiline, 4,4'-methylenebis(cyclohexan-1-amine), 4,4'-thiodianiline, 3,3'-((sulfonylbis(4,1-phenylene))bis(oxy))dianiline, 4,4'-(1,4-phenylenedisulfonyl)dianiline, 4,4'-(pentane-1,5-diylbis-(oxy))dianiline, 4,4'-([1,1'-biphenyl]-4,4'-diylbis(oxy))dianiline, 4,4'-(1,3-phenylenebis-(propane-2,2-diyl))bis(2,6-diisopropylaniline), 4,4'-(1,3-phenylenebis-(propane-2,2-diyl))dianiline, 4,4'-((sulfonylbis(4,1-phenylene))bis(oxy))dianiline, 4,4'-((propane-2,2-diylbis(4,1-phenylene))bis(oxy))dianiline, 4,4'-disulfanediyldianiline, and 4,4'-disulfanediyldianiline.

In one example the curing agent is an amine, wherein the ratio of the amine and a compound of Formula 1, Formula 2 or Formula 3, can vary from a balanced stoichiometry of about 1.0:1.0 to a stoichiometry of about 0.6:1.0. For example, the ratio of an amine curing agent and a compound of Formula 1, Formula 2 or Formula 3 can be about 1.0:1.0, about 0.95:1.0, about 0.90:1.0, about 0.85:1.0, about 0.75:1.0, about 0.70:1.0, about 0.65:1.0, or about 0.6:1.0. In one example the ratio is 0.7:1.0.

The curing agent can be a diamine curing agent of Formula 4:

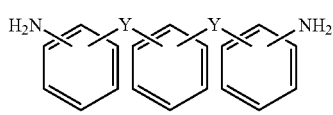

Formula 4 wherein each Y is the same and is selected from O, $CH_2$ and C(O).

In Formula 4, the two Y substituents can be connected to the central benzene ring in the ortho, meta or para positions with respect to one another. In one example the two Y substituents are in the 1 and 2 positions on the central benzene ring (ortho substitution). In another example the two Y substituents are in the 1 and 3 positions on the central benzene ring (meta substitution). In yet another example the two Y substituents are in the 1 and 4 positions on the central benzene ring (para substitution).

The curing agent can be a diamine curing agent of Formula 4a:

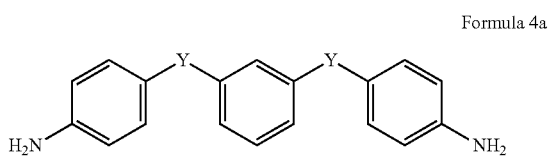

Formula 4a wherein each Y is the same and is selected from O, $CH_2$ and C(O).

The curing agent can be a diamine curing agent of Formula 4b:

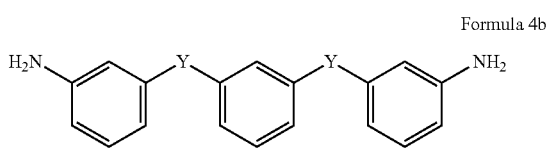

Formula 4b wherein each Y is the same and is selected from O, $CH_2$ and C(O).

The curing agent can be a diamine curing agent of Formula 4c:

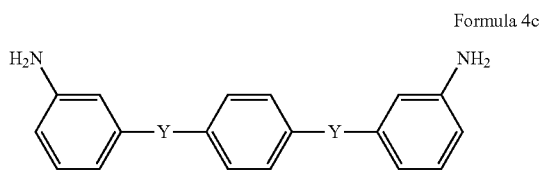

Formula 4c wherein each Y is the same and is selected from O, $CH_2$ and C(O).

The curing agent can be a diamine curing agent of Formula 4d:

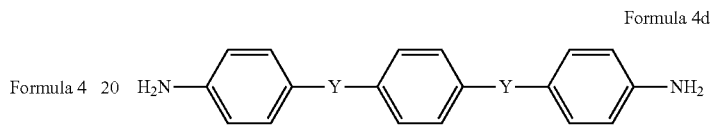

Formula 4d wherein each Y is the same and is selected from O, $CH_2$ and C(O).

For a compound of any one Formula 4, 4a, 4b, 4c or 4d, Y can be O, $CH_2$ or C(O).

In one example Y is O. In another example Y is C(O). In another example Y is $CH_2$.

In an example the compound of Formula 4 can be selected from any one of:

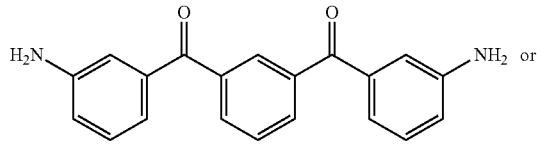

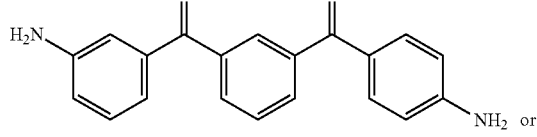

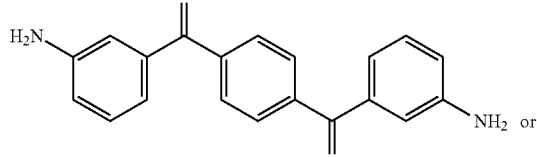

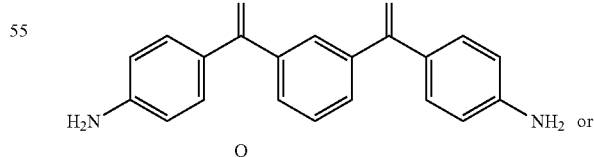

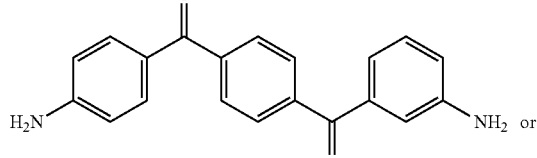

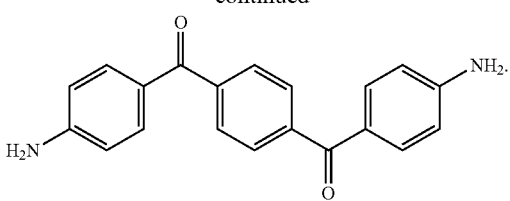

In an example the compound of Formula 4 can be selected from any one of:

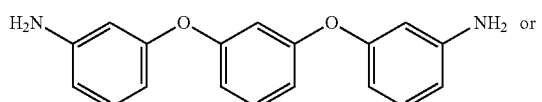
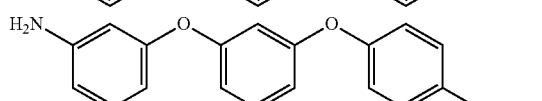
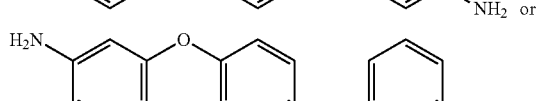
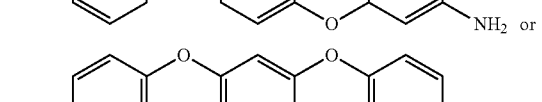
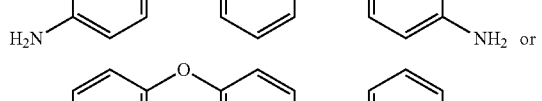
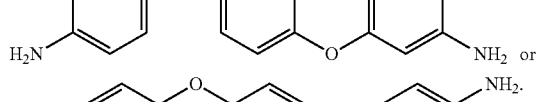

In an example the compound of Formula 4 can be selected from any one of:

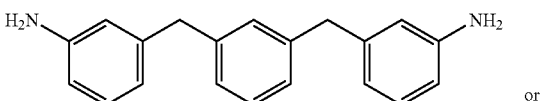
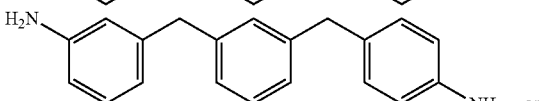
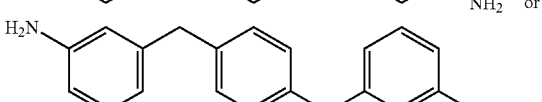
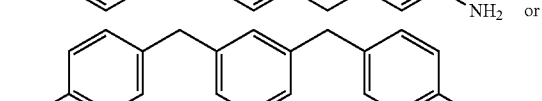
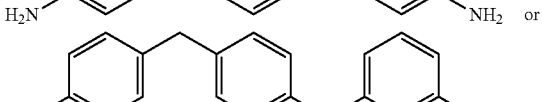

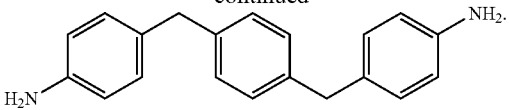

Herein, the ratio of a curing agent of Formula 4 and a compound of Formula 1, Formula 2 or Formula 3, can vary from a balanced stoichiometry of about 1.0:1.0 to a stoichiometry of about 0.6:1.0. For example, the ratio of a compound of Formula 4 and a compound of Formula 1, Formula 2 or Formula 3 can be about 1.0:1.0, about 0.95:1.0, about 0.90:1.0, about 0.85:1.0, about 0.75:1.0, about 0.70:1.0, about 0.65:1.0, or about 0.6:1.0. In one example the ratio is 0.7:1.0.

A curable epoxy resin formulation, as described herein, can further comprise one or more additives or one or more additional epoxy resins which are known in the art. These include: diglycidyl ethers of Bisphenol A, F epoxy resins, triglycidyl p-amino phenol epoxy resins and tetra glycidyl amine epoxy resins. For example, the curable epoxy resin formulation can further comprise 4,4'-methylenediphenol (Bisphenol F). Bisphenol F can be added as a liquid carrier for the manufacture of prepreg materials.

Examples of additives includes, but is not limited to, functional additives which can be added to the curable epoxy resin formulation in order to impart characteristics affecting the: mechanical, rheological, electrical, optical, chemical, flame resistance and/or thermal properties, of the cured or uncured epoxy resin formulation. Examples of additives include, but are not limited to: flame retardants, ultraviolet (UV) stabilisers and inorganic fillers.

Additives such as rheology modifiers, fillers, thermal or UV stabilizers, fire retardants, lubricants, surface active agents, can further include:

a) film formers such as esters of dicarboxylic acid (e.g. Lusolvan FBH, BASF) and glycol ethers (e.g. Dowanol, Dow); and b) surfactants such as fatty acid derivatives (e.g. Bermadol SPS 2543, Akzo) and quaternary ammonium salts.

In one example the curable epoxy resin formulation comprises no additives.

Composite Materials

Disclosed herein are impregnated fibre reinforced materials comprising fibres impregnated with a curable epoxy resin formulation as defined herein.

The fibre reinforced materials can comprise fibres selected from, but not limited to, fibres composed of: fibreglass, carbon, or aramid (aromatic polyamide).

In one example the impregnated fibre reinforced materials comprise a compound of any one of Formula 1, 1a, 1b, 2, 2a, 2b or a mixture thereof, and a curing agent.

In one example the impregnated fibre reinforced materials comprise a compound of Formula 3 and a curing agent, for example a curing agent of any one of Formula 4, 4a, 4b, 4c, or 4d, or a mixture thereof.

Also disclosed herein are composite materials comprising a fibrous material in a matrix of a cured epoxy resin, wherein the cured epoxy resin is formed from a curable epoxy resin formulation as defined herein.

In one example the composite materials comprise a compound of any one of Formula 1, 1a, 1b, 2, 2a, 2b or a mixture thereof, and a curing agent.

In one example the composite materials comprise a compound of Formula 3 and a curing agent of any one of Formula 4, 4a, 4b, 4c, 4d or a mixture thereof.

Also disclosed herein are methods of forming an impregnated fibre reinforced material, the method comprising the steps of:
a) providing:
   (i) a curable epoxy resin formulation as defined herein; and
   (ii) a fibrous material; and
b) combining the resin formulation of step (a)(i) with the fibrous material of step (a)(ii) and subjecting the material to an elevated temperature capable of curing to form the impregnated fibre reinforced material.

The fibrous material can comprise fibres composed of: fibreglass, carbon, aramid (aromatic polyamide) fibres.

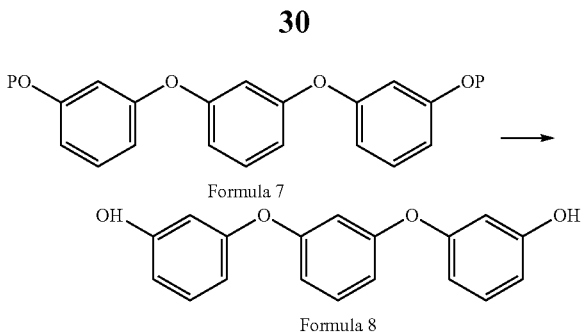

Also disclosed herein is a process for preparing a compound of Formula 10, comprising a step of reacting a dihydroxyl compound of Formula 8 with a halogenated epoxy compound of Formula 9 to form the compound of Formula 10:

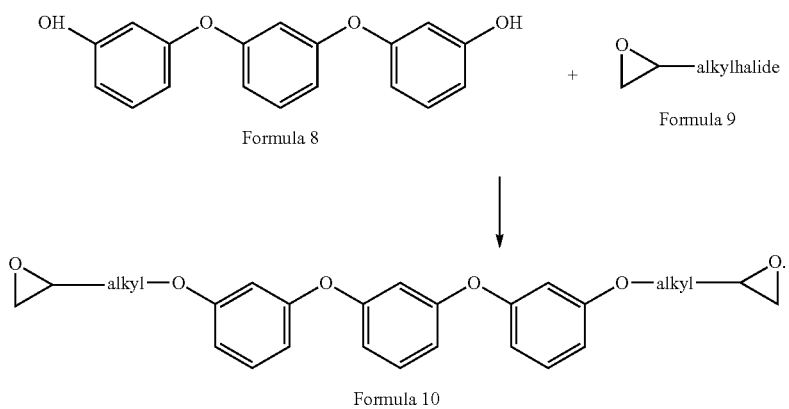

In addition, also disclosed herein is a use of a compound of any one of Formula 1, 1a, 1b, 2, 2a, 2b, or a mixture thereof, as a curable epoxy resin or in the preparation of a curable epoxy resin formulation. The curable epoxy resin formulation can be used in the production of an impregnated fibre reinforced material or composite material thereof.

Furthermore, disclosed herein is a process for preparing a compound of Formula 8 comprising the steps of:
i) reacting together a compound of Formula 5 with a compound of Formula 6 in the presence of a catalyst to form a compound of Formula 7, wherein P is a protecting group, M is a metal and LG is a leaving group:

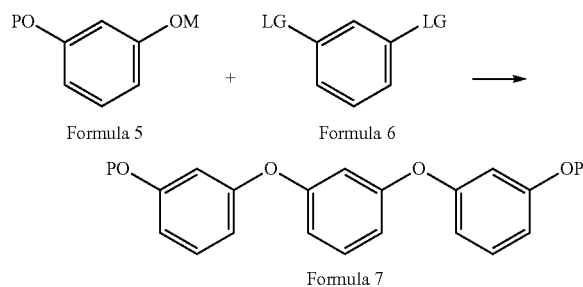

ii) further reacting the compound of Formula 7 with an acid catalyst to form a compound of Formula 8:

For Formula 9, the alkyl group can be a $C_{1-3}$ alkyl group. For example, the compound of Formula 9 can be epichlorohydrin.

Protecting groups, can be temporary or permanent, are known in the art, and methods for their installation and removal are described in standard references such as *Protective Groups in Organic Synthesis*, T. W. Greene and P Wutz, John Wiley and Son, $2^{nd}$ Edition (1991), the contents of which are incorporated by reference. In Formulae 5 and 7, hydroxyl groups can be protected using groups such as: acetyl, benzoyl, benzyl, methoxymethyl ether, methoxytrityl, methylthiomethyl ether, pivaloyl, tetrahydropyranyl, tetrahydrofuran, trityl, silyl ether (including trimethylsilyl, tert-butyldimethylsilyl, tri-iso-propylsilyloxymethyl and tri-isopropylsilyl ether), alkyl ethers (such as methyl ethers) and ethoxyethyl ether, protecting groups. For example, protecting group "P", for formulae 5 and 7, can be an alkyl group, such as a methyl group.

Examples of metal "M" includes, but is not limited to: potassium or sodium.

The term "leaving group" or "LG" will be understood by the skilled person and means a molecular fragment which is capable of being displaced as a stable species taking it with it the bonding electrons. Leaving groups are used in organic chemistry to facilitate covalent bonding between two moieties. The term "leaving group" or "LG" includes, but is not limited to: halo groups (such as iodo, bromo, and chloro) or sulfonate ester groups such as mesylate, tosylate, osylate, nosylate, or besylate.

EXAMPLES

Raw Materials

Certain chemicals referred to within the specification, including the following examples, can be obtained from the suppliers indicted in Table 1.

TABLE 1

| Suppliers for selected compounds disclosed in the examples. | |
| --- | --- |
| Component(s) | Example Supplier |
| 1,4-Dihydroxybenzene, 4-fluoroacetophenone, 3-methoxyphenol, 1,3-dibromobenzene, m-chlorobenzoic acid, dimethyl acetamide, cuprous chloride, lanthanum nitrate and epichlorohydrin | Sigma Australia |
| Ethanol, toluene, dichloromethane, dichloroethane, diethylether, iso-propanol, chloroform, methanol, epichlorohydrin, potassium hydroxide, sodium hydroxide, sodium sulphate, sodium sulphite, sodium bicarbonate and acetic acid | Merck, (Germany) |
| Hydrogen bromide | Fluka (Japan) |
| 1,4 bis-(4-aminophenoxy)benzene | Chriskev (USA) |
| Diglycidyl ether of Bis phenol A, diglycidyl ether of Bis phenol F | Momentive Chemicals (Malaysia) |
| 4,4-diaminodiphenyl sulfone | Vantico (Australia) |

Equipment

Nuclear Magnetic Resonance (NMR) Spectroscopy

The NMR experiments were performed on a Bruker Avance 400 NMR spectrometer (400.13 MHz $^1$H frequency) equipped with a 5 mm triple resonance broadband probe (BB/$^2$H-$^1$H/$^{19}$F) or a 5 mm inverse broadband probe ($^1$H/$^2$H-BB). Solutions for analysis by NMR were prepared by dissolving the material in 0.6 ml of deuterated chloroform (CDCl$_3$). NMR experiments were performed with the sample held at 25±0.1° C. Chemical shifts for $^1$H experiments are referenced to the residual solvent signal (CHCl$_3$, δ 7.24 ppm) and for $^{13}$C referenced to the solvent signal (CDCl3, δ 77.23 ppm).

High Performance Liquid Chromatography (HPLC)

High Performance Liquid Chromatograph was performed using a Waters 2695 Separation Module and a Waters 2996 Photodiode Array (PDA) or a 2414 Refractive Index (RI) detector. The column was a reverse phase Alltima C18 150×4.6 mm column. The flow rate used was 1.00 mL/min, while the mobile phase changed from 55% acetonitrile (CAN)/45% H$_2$O to 65% acetonitrile (CAN)/35% H$_2$O.

Electron Spray Ionisation (ESI) Mass Spectrometry (MS)

Mass spectrometric analyses were performed on a Thermo Scientific Q Exactive mass spectrometer fitted with a HESI-II ion source. Positive and/or negative ion electrospray mass spectra were recorded in an appropriate mass range set for 140,000 mass resolution. The probe was used with 0.3 ml/min flow of solvent. The nitrogen nebulizing/desolvation gas used for vaporization was heated to 350° C. in these experiments. The sheath gas flow rate was set to 35 and the auxiliary gas flow rate to 25 (both arbitrary units). The spray voltage was 3.0 kV and the capillary temperature was 300° C.

Differential Scanning Calorimetry (DSC)

Differential Scanning Calorimetry (DSC) was performed using a Mettler DSC821$^e$ DSC in the dynamic mode using, approximately 5-10 mg of sample. The sample was placed in a sealed alumina crucible and placed inside the furnace under a blanket of nitrogen. Both cured and uncured samples were heated from 50° C. to 300° C. at a rate of 10° C./min to determine the best cure temperature, get an initial understanding of the reactivity, determine the glass transition temperature of the network and also gain an informal understanding of the extent of cure.

Abbreviated Terms

Table 2 lists a series of abbreviated terms which are used herein.

TABLE 2

| Acronyms used for compounds and components described herein | |
| --- | --- |
| Acronym | Compound/Component |
| TPE-Q | 1,4-bis(4-aminophenoxy)benzene |
| TPE-R | 1,3-bis(4-aminophenoxy)benzene |
| 133-APB | 1,3-bis(3-aminophenoxy)benzene |
| BHPmX | Bis(4-hydroxyphenyl)m-xylene |
| BHPpX | Bis(4-hydroxyphenyl)-p-xylene |
| 144 TGAPP | N,N,N,N-Tetraglycidyl 1,4-Bis(4-aminophenoxy)Benzene |
| 134 TGAPB | N,N,N,N-Tetraglycidyl 1,3-Bis(4-aminophenoxy)Benzene |
| 133TGAPB | N,N,N,N-Tetraglycidyl 1,3-Bis(3-aminophenoxy)Benzene |
| 133-BGOPB | 1,3-Bis(3-glycidyloxyphenoxy)benzene |
| 144-BGOPB | 1,4-Bis(4-glycidyloxyphenoxy)benzene |

Example 1—Synthesis of N,N,N,N-Tetraglycidyl 1,4-Bis(4-aminophenoxy)Benzene (144-TGAPB)

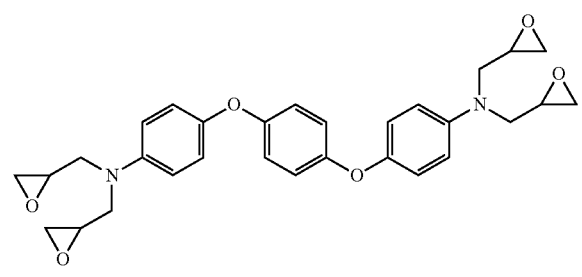 [SMILES: c1cc(Oc2ccc(N(CC3CO3)CC3CO3)cc2)ccc1Oc1ccc(N(CC2CO2)CC2CO2)cc1]

1,4-Bis(4-aminophenoxy)Benzene (144-TGAPB)

The materials used in the synthesis of 144-TGAPB are shown below:

1,4-bis(4-aminophenoxy)benzene (TPE-Q) 5.84 g (2.00×10$^{-2}$ mole);
epichlorohydrin (27.75 g, 3.00×10$^{-1}$ mole);
dichloroethane (50 ml);
lanthanum nitrate hexahydrate (55 mg);
NaOH (4.00 g, 1.00×10$^{-1}$ mole); and
isopropanol (30 ml).

TPE-Q, epichlorohydrin, dichloroethane and lanthanum nitrate (in 2 ml of isopropanol) were placed in a 250 ml three necks round bottom flask. The mixture was refluxed in an oil bath for 90 minutes (oil bath temperature ~100° C., inside reaction flask ~87° C.). After the 980 minutes had elapsed, the temperature of the oil bath was dropped to ~80° C. in order to reduce the temperature inside the reaction flask to ~70-75° C.

NaOH was ground to coarse powder and suspended in isopropanol. This suspended solution was added slowly to the TPE-Q/Epichlorohydrin solution in small portions (by spoon) over 30 minutes. After the addition was complete, the mixture was stirred at 70-75° C. for further 15 minutes then allowed to cool to room temperature.

The salt was filtered, and the solvents and excess epichlorohydrin were removed under rotary evaporator (oil pump) at ~50° C. for 1-2 hours. The residue was then suspended in methanol (50 ml). The solid product was filtered and then resuspended in methanol (50 ml) and filtered again. The white solid product was dried in a vacuum oven at ~70° C. overnight. The yield was 9.70 g (94%). The product was analysed by NMR ($^1$H and $^{13}$C) (FIG. 1, images a) and b), respectively), high performance liquid chromatography (HPLC) (FIG. 2), mass spectrometry (MS), differential scanning calorimetry (DSC) and thin-layer chromatography (TLC).

TLC (silica plate; solvents: 2% v/v MeOH in DCM)-$R_f$ value ~0.8.

MS (ESI) m/z 516.

Figure 2:
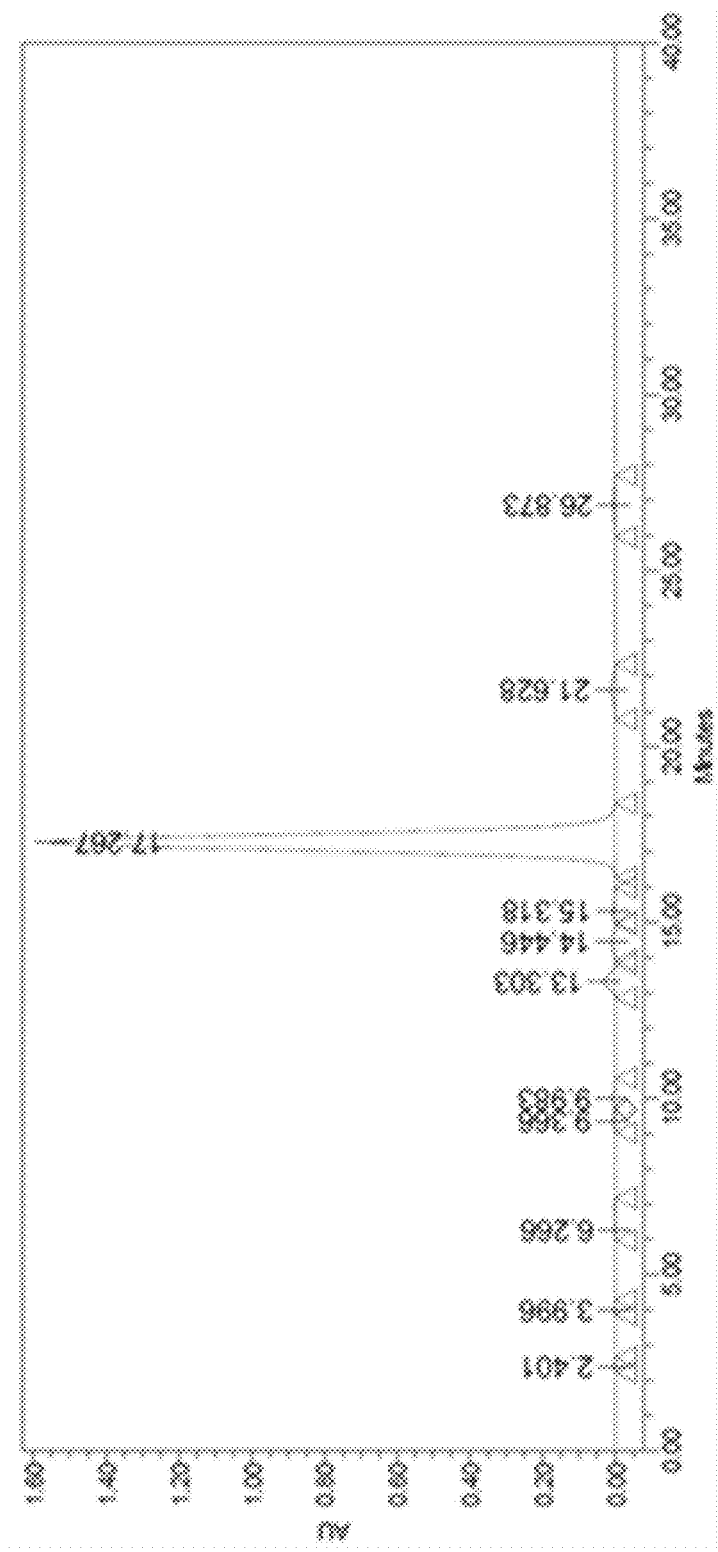
FIG. 2—High performance liquid chromatogram showing the resolution times for components in the synthesis of N,N,N,N-tetraglycidyl 1,4-bis(4-aminophenoxy)benzene (144-TGAPB).

HPLC: HPLC column Altima C18; mobile phase: 55% acetonitrile/water; single peak with retention time (RT) of 17.267 minutes; 95.7% (FIG. 2).

Example 2—Synthesis of N,N,N,N-Tetraglycidyl 1,3-Bis(4-aminophenoxy)Benzene (134-TGAPB)

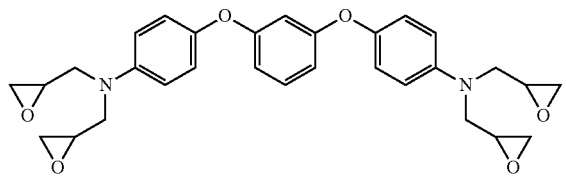 [SMILES: c1cc(Oc2ccc(N(CC3CO3)CC3CO3)cc2)cc(Oc2ccc(N(CC3CO3)CC3CO3)cc2)c1]

1,3-Bis(4-aminophenoxy)benzene (134-TGAPB)

The materials used in the synthesis of 134-TGAPB are shown below:

1,3-bis(4-aminophenoxy)benzene (TPE-R) 5.84 g ($2.00 \times 10^{-2}$ mole);
epichlorohydrin (27.75 g, $3.00 \times 10^{-1}$ mole);
dichloroethane (50 ml);
lanthanum nitrate hexahydrate (55 mg);
NaOH (4.0 g, $1.00 \times 10^{-1}$ mole); and
isopropanol (30 ml).

TPE-R, epichlorohydrin, dichloroethane and lanthanum nitrate (in 2 ml of isopropanol) were placed in a 250 ml three necks round bottom flask. The mixture was refluxed in an oil bath for 90 minutes (oil bath temperature ~100° C., inside reaction flask ~87° C.). After the 90 minutes has elapsed, the temperature of the oil bath was dropped to ~80° C. in order to reduce the temperature inside the reaction flask to ~70-75° C.

Figure 3:
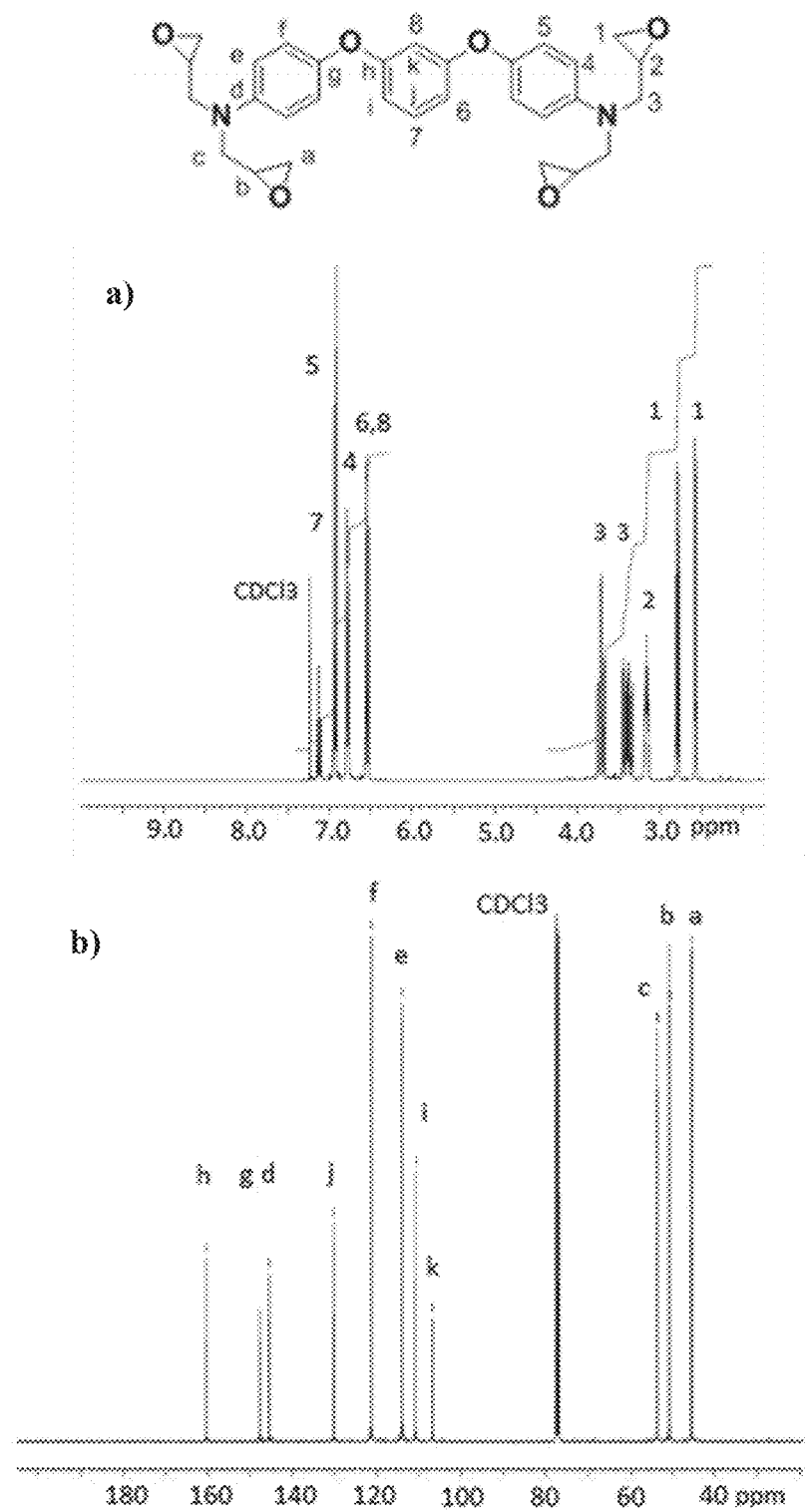
FIG. 3—$^1$H (image a)) and $^{13}$C (image b)) nuclear magnetic resonance spectra for N,N,N,N-tetraglycidyl 1,3-bis(4-aminophenoxy)benzene (134-TGAPB).

NaOH was ground to form a coarse powder which was suspended in isopropanol. This suspended solution was added slowly to the TPE-R/epichlorohydrin solution in small portions (using a spoon) over 30 minutes. After the addition was complete, the mixture was stirred at 70-75° C. for a further 15 minutes. The solution was then allowed to cool to room temperature. The salt was filtered, and the solvents and excess epichlorohydrin were removed under rotary evaporator (oil pump) at ~50° C. for 1-2 hours. The residue was dissolved in dichloromethane (50 ml), washed with water (50 ml) and dried over Na$_2$SO$_4$ (anhydrous). The Na$_2$SO$_4$ was then filtered off (with celite) and the dichloromethane was removed. The product was a dark oil with a yield of 9.90 g (96% yield). The oily product was analysed by NMR ($^1$H and $^{13}$C—FIG. 3, images a) and b), respectively), HPLC (FIG. 4), MS and TLC.

TLC (silica plate; solvents: 2% v/v MeOH in DCM), $R_f$ value ~0.7.

MS (ESI) 516.

Figure 4:
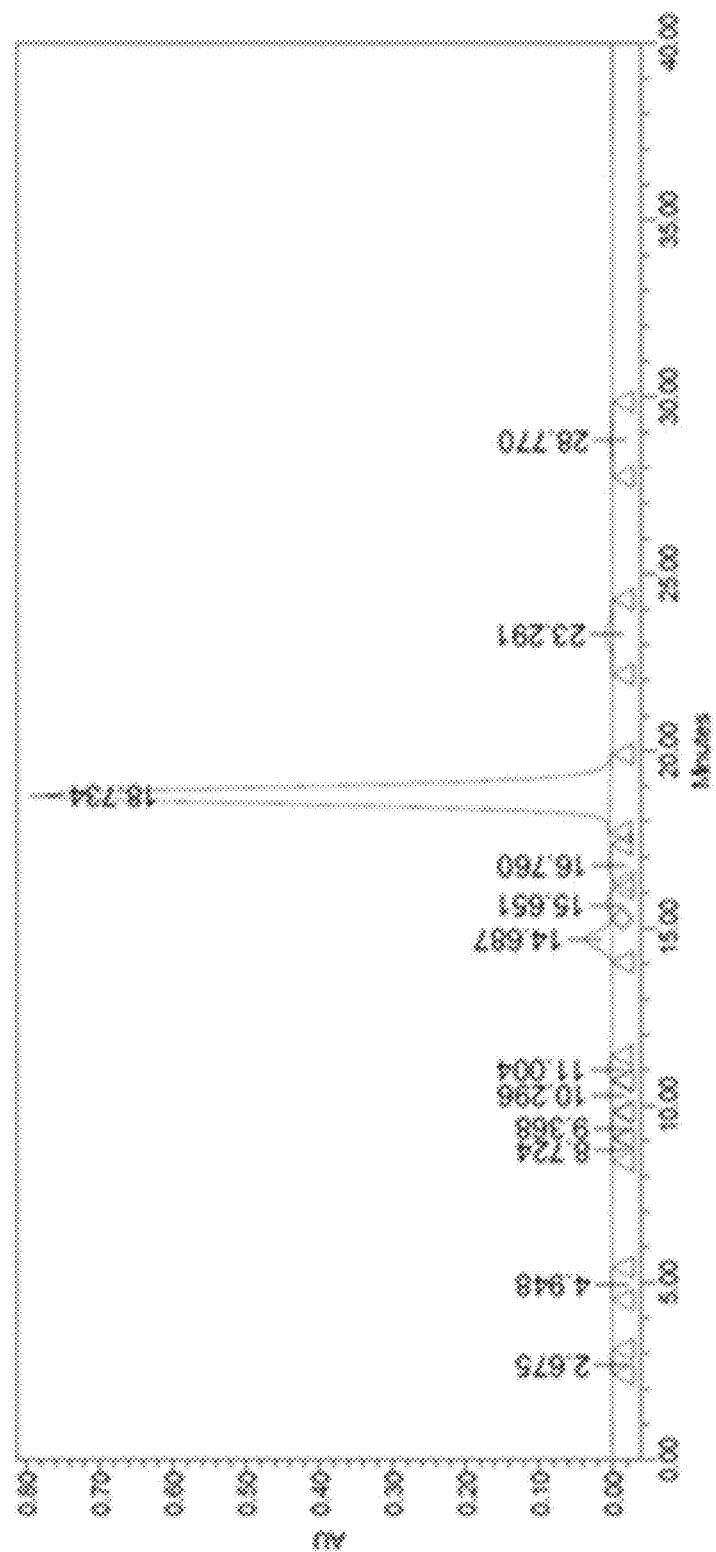
FIG. 4—High performance liquid chromatogram showing the resolution times for components in the synthesis of N,N,N,N-tetraglycidyl 1,3-bis(4-aminophenoxy)benzene (134-TGAPB).

HPLC: HPLC column Altima C18; mobile phase: 55% acetonitrile/water; single peak with RT 18.73 minutes; 92.4% (FIG. 4).

Example 3—Synthesis of N,N,N,N-Tetraglycidyl 1,3-Bis(3-aminophenoxy)Benzene (133-TGAPB)

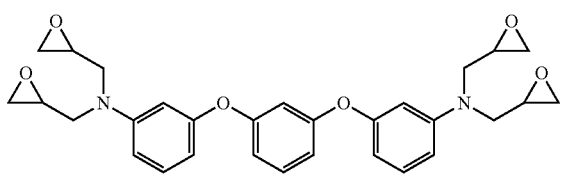 [SMILES: c1cc(Oc2cccc(N(CC3CO3)CC3CO3)c2)cc(Oc2cccc(N(CC3CO3)CC3CO3)c2)c1]

1,3-Bis(3-aminophenoxy)Benzene (133-TGAPB)

The materials used for the synthesis of 133-TGAPB are shown below:

1,3-bis(3-aminophenoxy)benzene (133-APB) 5.84 g ($2.00 \times 10^{-2}$ mole);
epichlorohydrin (27.75 g, $3.00 \times 10^{-1}$ mole);
dichloroethane (50 ml);
lanthanum nitrate hexahydrate (55 mg);
NaOH (4.0 g, $1.00 \times 10^{-1}$ mole); and
isopropanol (30 ml).

133-APB, epichlorohydrin, dichloroethane and lanthanum nitrate (in 2 ml of isopropanol) were placed in a 250 ml three necks round bottom flask. The mixture was refluxed in an oil bath for 90 minutes (oil bath temperature ~100° C., inside reaction flask ~87° C.). After the 90 minutes had elapsed the temperature of the oil bath was dropped to ~80° C. in order to reduce the temperature inside the reaction flask to ~70-75° C.

Figure 5:
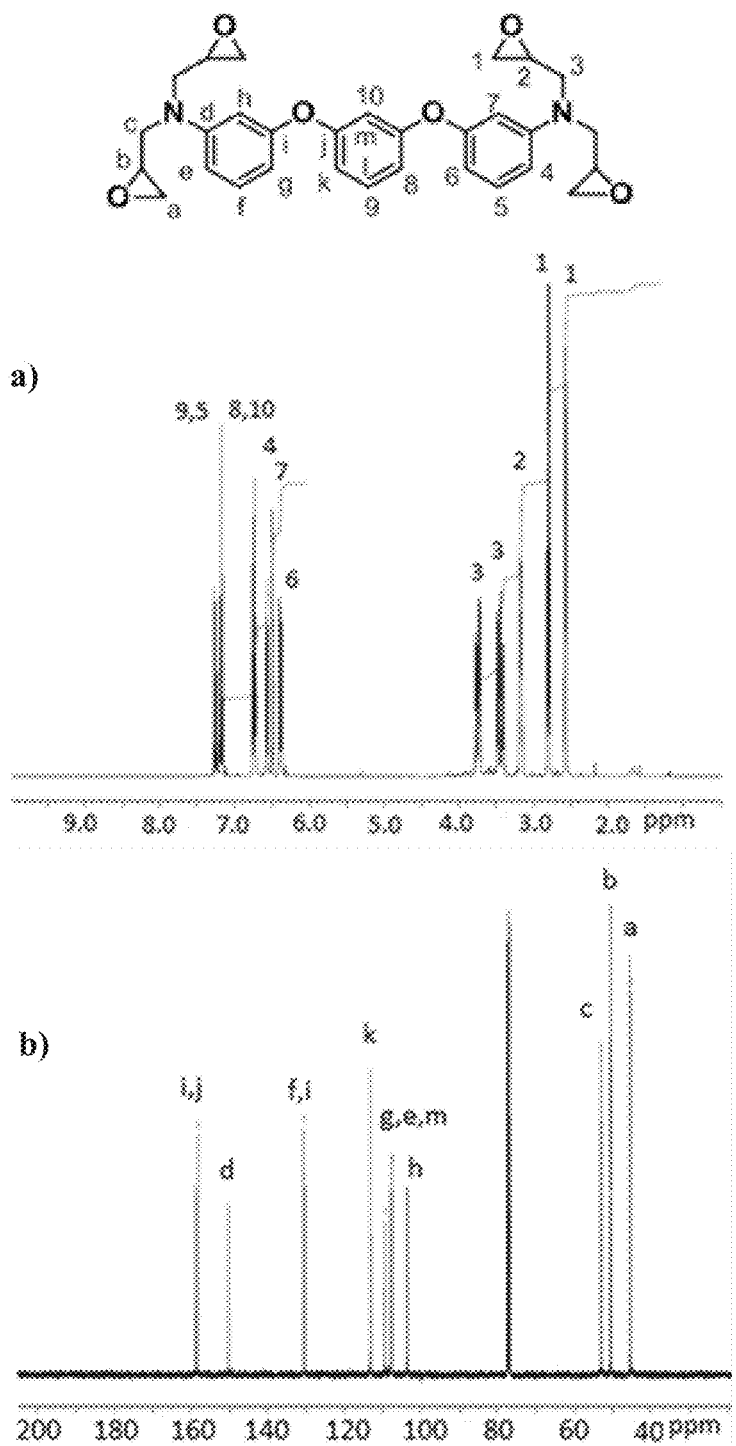
FIG. 5—$^1$H (image a)) and $^{13}$C (image b)) nuclear magnetic resonance spectra for N,N,N,N-tetraglycidyl 1,3-bis(3-aminophenoxy)benzene (133-TGAPB).

NaOH was ground to form a coarse powder and then suspended in isopropanol. This suspended solution was added slowly to the 133-APB/epichlorohydrin solution in small portions (by spoon) over 30 minutes. After the addition was complete, the mixture was stirred at 70-75° C. for a further 15 minutes, and then allowed to cool to room temperature. The salt was filtered and the solvents and excess epichlorohydrin were removed under rotary evaporator (oil pump) at ~50° C. for 1-2 hours. The residue was dissolved in dichloromethane (50 ml), washed with water (50 ml) and dried over Na$_2$SO$_4$ (anhydrous). The Na$_2$SO$_4$ was filtered off (with celite) and the dichloromethane was removed. The product was a yellow oil with a yield of 9.90 g (96% yields). The oily product was analysed by NMR ($^1$H and $^{13}$C, FIG. 5, images a) and b), respectively), HPLC (FIG. 6), MS and TLC.

TLC (silica plate; solvents: 2% v/v MeOH in DCM), $R_f$ value ~0.85.

MS (ESI) 516.

Figure 6:
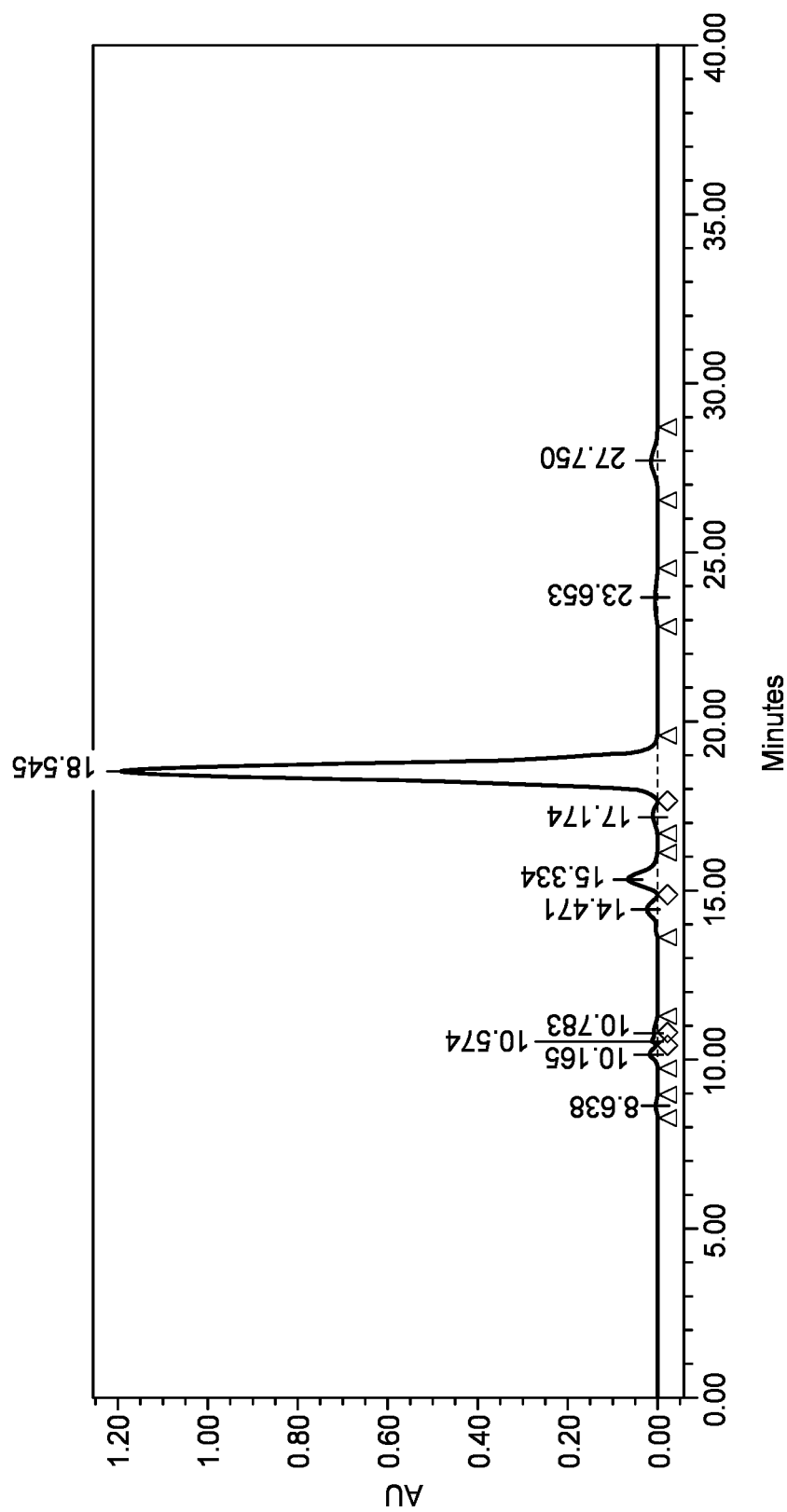
FIG. 6—High performance liquid chromatogram showing the resolution times for components in the synthesis of N,N,N,N-tetraglycidyl 1,3-bis(3-aminophenoxy)benzene (133-TGAPB).

HPLC: HPLC column Altima C18; mobile phase: 55% acetonitrile/water; single peak with RT 18.56 minutes; 90.2% (FIG. 6).

Example 4—Synthesis of 1,3-Bis(3-glycidyloxyphenoxy)benzene (133-BGOPB)

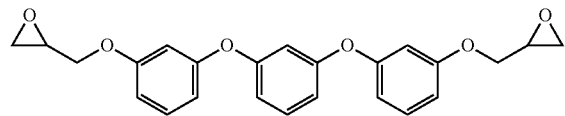 [SMILES: c1cc(OCC2CO2)cc(Oc2cccc(Oc3cccc(OCC4CO4)c3)c2)c1]

1,3-Bis(3-glycidyloxyphenoxy)benzene (133-BGOPB)

Step 1—Synthesis of 1,3-Bis(3-methoxyphenoxy)benzene

This synthesis utilised a modified form of a process published in L. Wang et al., *Synthesis Communication*, 30(2), 227-234, 2000, the content of which is hereby incorporated herein by reference.

Scheme 1 - Synthesis of 1,3-bis(3-methoxyphenoxy)benzene.

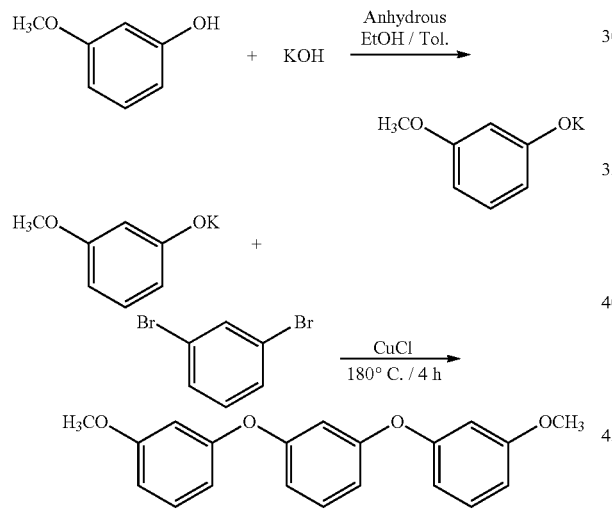

3-Methoxyphenol (62.05 g, $5.00 \times 10^{-1}$ mol) was added to a mixture of KOH (30.85 g, $5.50 \times 10^{-1}$ mol) dissolved in ethanol/toluene (75 ml/150 ml). The mixture was stirred and refluxed under a nitrogen atmosphere until the solid had completely dissolved. The solvents were removed, initially by distillation and then using a rotary evaporator. Cuprous chloride (1.25 g, $1.25 \times 10^{-2}$ mol) and 1,3-dibromobenzene (59 g, $2.50 \times 10^{-1}$ mol) were added to the residues which were then stirred at 170-180° C. for 16 hours. The following day, the reaction flask was warmed to approximately 50° C., and then ethanol (200 ml) and water (200 mL) were added to the mixture. The product was extracted with $CH_2Cl_2$ (250 ml×2), washed separately with a 5% aqueous NaOH solution (250 ml×2) and finally with water (250 ml×2). After drying with $Na_2SO_4$, the $CH_2Cl_2$ solvent was removed to produce 46.9 g of a dark oil (58.2% yield). NMR analysis proved that was an expected product and ready for next step.

Step 2—Synthesis of 1,3-Bis(3-hydroxyphenoxy)benzene (133-BGOPB)

Scheme 2 - Synthesis of 133-BGOPB.

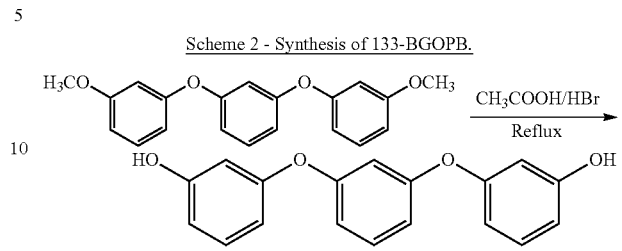

A mixture of 1,3-bis(3-methoxyphenoxy)benzene (46.89 g, $1.46 \times 10^{-1}$ mol), glacial acetic acid (460 ml) and HBr (300 ml) was refluxed for 5 hours after which time the reaction mixture was allowed to cool to room temperature. The reaction mixture was then poured into water (5 L) before the product was extracted with 2 L of ether (500 ml×4). The combined ether solution was then washed with water (750 ml×2), dried over $Na_2SO_4$ and filtered. The ether was removed under vacuum and the product obtained was a dark oil (40.0 g) (93% yield). The NMR analysis showed the product which was used in the next step.

Step 3—Synthesis of 1,3-Bis(3-glycidyloxyphenoxy)benzene (133-BGOPB)

Scheme 3 - Synthesis of 133-BGOPB.

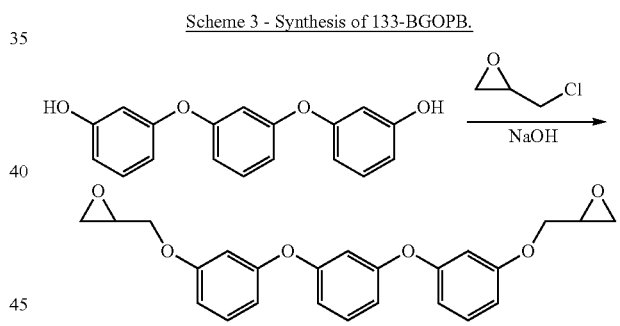

Synthesis of the epoxy resin was completed by mixing together the 1,3-bis(3-hydroxyphenoxy)benzene, epichlorohydrin (125.58 g, 1.36 mol) and isopropanol (57 g, $9.50 \times 10^{-1}$ mol) together, and heating at 70° C. with stirring. The epoxide ring was closed by adding 100 ml of 15% w/v NaOH aqueous solution to the above stirring solution in two stages. First, 8-9 ml was added drop wise over 5 minutes then the remaining 90 ml was slowly added over 10 minutes. After such time the mixture was heated at 70-75° C. for a further 30 minutes then allowed to cool to room temperature. The organic phase (lower phase which contains the product) was separated from the aqueous phase (top phase) and washed with water (250 ml×2). The organic solution was then diluted with $CH_2Cl_2$ (200 ml), dried over $Na_2SO_4$ and filtered. The solvents were removed under vacuum and the product was obtained as a dark oil. This product was purified by passed through a short $SiO_2$ column with $CH_2Cl_2$ as solvent. The pure product was obtained as a yellow oil (40 g, 72.6% yield). The epoxy equivalent weight of 133-BGOPB was determined to be 239 mol/g.

Figure 7:
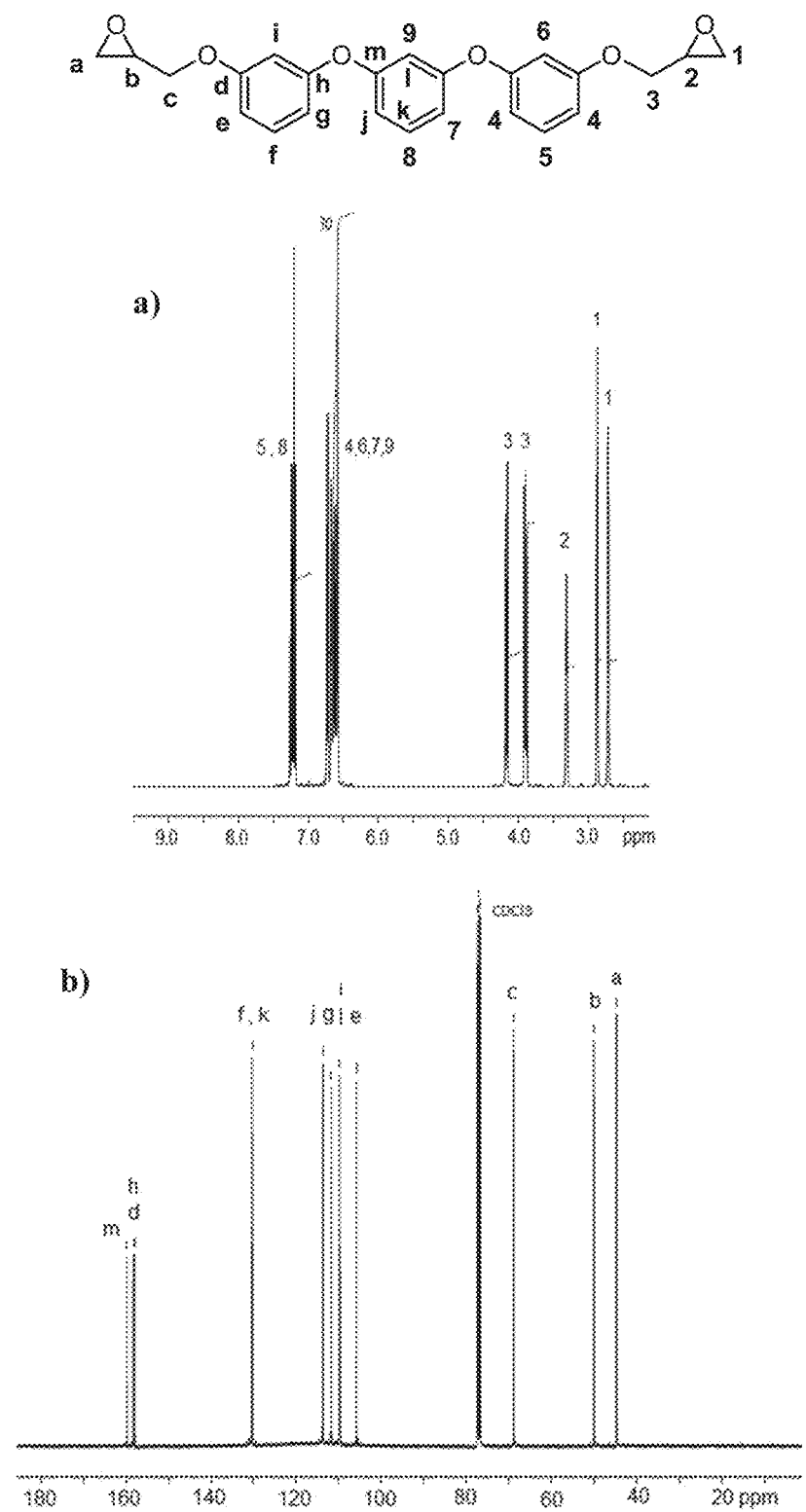
FIG. 7—$^1$H (image a)) and $^{13}$C (image b)) nuclear magnetic resonance spectra for 1,3-bis(3-glycidyloxyphenoxy)benzene.
Figure 8:
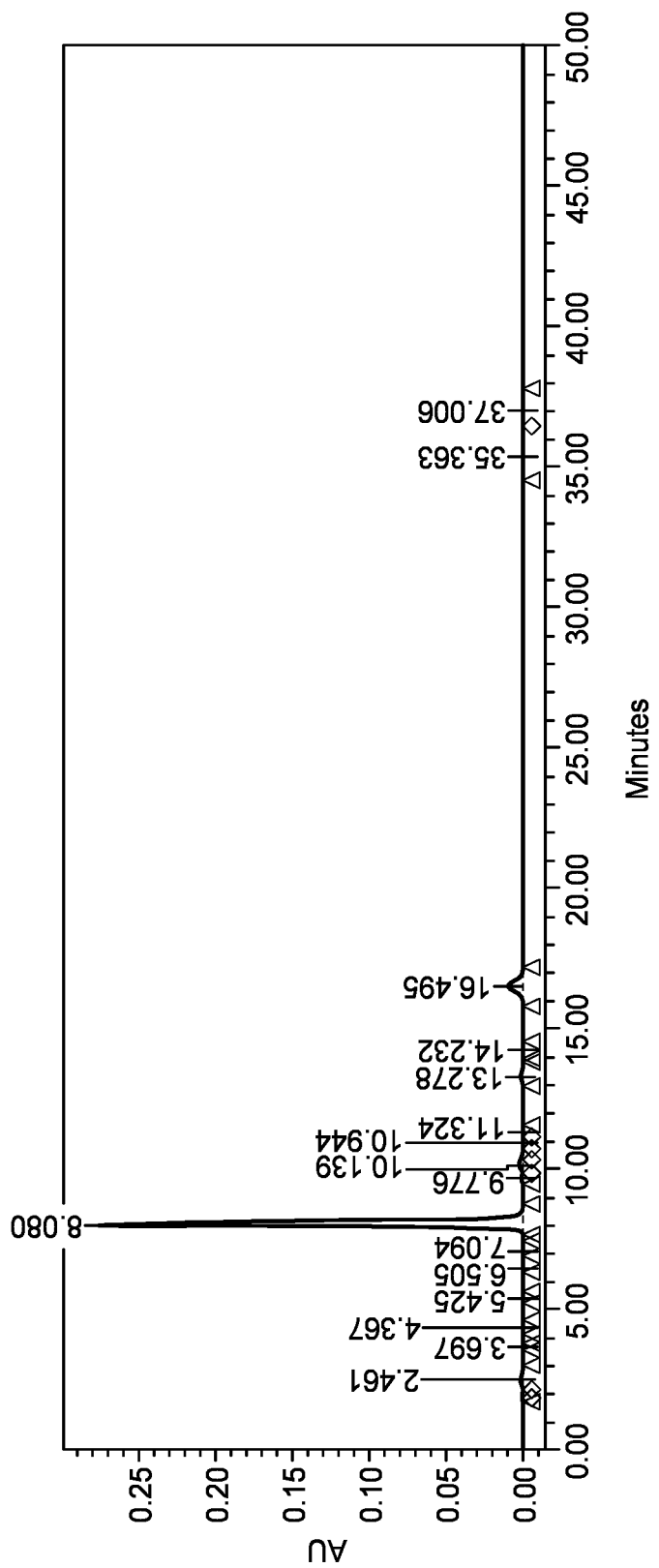
FIG. 8—High performance liquid chromatogram showing the resolution times for components in the synthesis of 1,3-bis(3-glycidyloxyphenoxy)benzene.

The proton and carbon NMR spectra are shown in FIG. 7, images a) and b), respectively. The spectra show that the product is clean and free of impurities. Each peak can be assigned conveniently to the relevant hydrogen or carbon atom as shown in the insert. The integration of the hydrogen peaks aligns conveniently with what is expected for the 133 BGOPB molecule. The synthesis provides a clean synthesis, free from easily detectable impurities. In addition to this, the HPLC chromatogram in FIG. 8 shows the separated components of the 133 BGOPB providing clear evidence that the molecule is a pure single component epoxy resin. For the HPLC analysis a 150×4.6 mm Altima C18 column was used. The mobile phase was 65% acetonitrile/water with a flow rate of 1.0 mL min$^{-1}$.

Example 5—Synthesis of 1,4-Bis(4-glycidyloxyphenoxy)benzene (144-BGOPB)

Step 1—Synthesis of 1,4-Bis(4-acetophenoxy)benzene

This synthesis utilised a modified form of a process published in G. W. Yeager et al., *Synthesis,* 1991, 63-68, the content of which is hereby incorporated herein by reference.

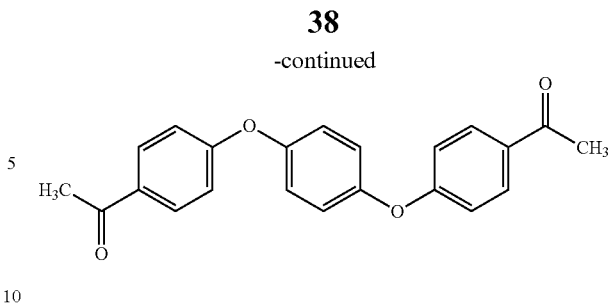

Anhydrous K$_2$CO$_3$ (64.27 g, 4.65×10$^{-1}$ mol) was added slowly to a stirred solution of 1,4-dihydroxybenzene (25.6 g, 2.33×10$^{-1}$ mol), 4-fluoroacetophenone (64.17 g, 4.65×10$^{-1}$ mol) and DMAc (700 ml), the resulting mixture was then refluxed overnight under nitrogen. The following day the mixture was allowed to cool to room temperature and poured slowly into water (2.0 L). The product was precipitated out as a solid and isolated from solution by filtration. The product was suspended in water (2×1 L), filtered and dried in a vacuum oven at 50-70° C. for 24 hours. The yield was 74 g (92%). NMR analysis proved that was an expected product and ready for next step.

Step 2. Synthesis of 1,4-Bis(4-acetoxyphenoxy)benzene

Scheme 5 - Synthesis of 1,4-bis(4-acetoxyphenoxy)benzene.

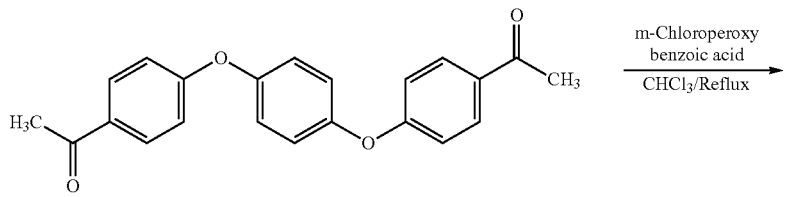

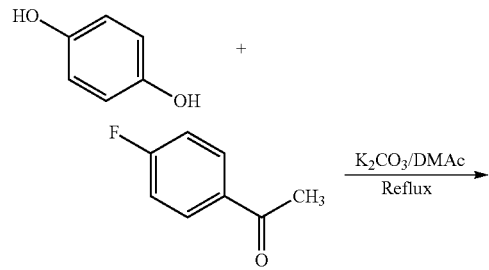

Scheme 4 - Synthesis of 1,4-bis(4-acetophenoxy)benzene.

A mixture of 1,4-bis(4-acetophenoxy)benzene (69.2 g, 2.00×10$^{-1}$ mol), m-chloroperoxybenzoic acid (107.5 g) and CHCl$_3$ (500 ml) was stirred under reflux for 5 hours. After this time, the reaction mixture was allowed to cool to room temperature then the solid was filtered and washed with CH$_2$Cl$_2$ (200 ml). The combined organic solvent was washed with saturated NaHSO$_3$ solution (2×250 ml) then saturated NaHCO$_3$ solution (2×250 ml) and finally with water (2×500 ml). The organic phase was dried in anhydrous Na$_2$SO$_4$, filtered and organic solvent was removed by rotary evaporator. The product formed as a yellow solid. This solid product was dried in a vacuum oven at 50° C. overnight. The yield was 64 g (84.6%). The NMR showed the product which was used in the next step.

Step 3—Synthesis of
1,4-Bis(4-hydroxyphenoxy)benzene

Scheme 6 - Synthesis of 1,4-bis(4-hydroxyphenoxy)benzene.

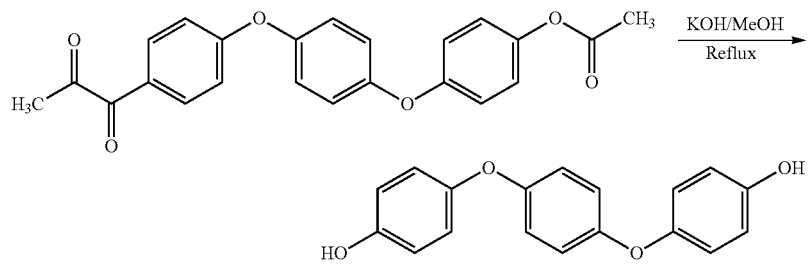

To a stirred solution of 1,4-bis(4-acetatephenoxy)benzene (63.75 g, 1.69×10$^{-1}$ mol) in MeOH (700 ml), 0.5M KOH/MeOH solution (85 ml) was added and heated to reflux for 1 hour. After this time, the solvent was then removed by rotary evaporator. The residue was suspended in water (800 ml) and acidified with concentrated HCl. The solid product was isolated from the solution by filtration and washed twice with water before dried in a vacuum oven at 70° C. overnight. The yield was 46.5 g (93.8%). The product was checked by NMR and ready for next step.

Step 4—Synthesis of
1,4-Bis(4-glycidyloxyphenoxy)benzene
(144-BGOPB)

Scheme 7 -
Synthesis of 1,4-Bis(4-glycidyloxyphenoxy)benzene (144-BGOPB).

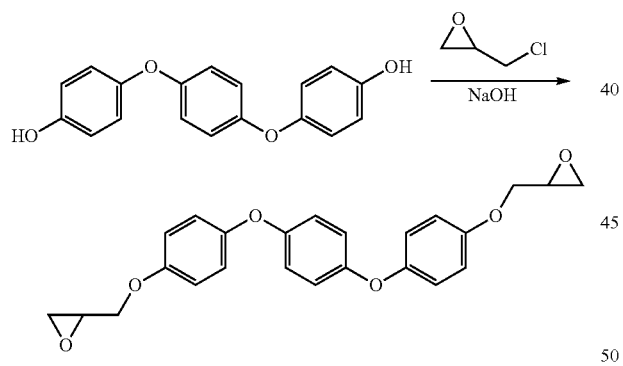

1,4-Bis(4-hydroxyphenoxy)benzene (46.5 g, 1.58×10$^{-1}$ mol), epichlorohydrin (146.4 g, 1.58×10$^{-1}$ mol) and isopropanol (66.4 g, 1.11 mol) were dissolved together in a round bottom flask and heated and stirred at 70° C. Following this, 115 ml of 15% w/v aqueous NaOH solution was added to the above stirring solution in two stages. First 10 ml was added drop wise over 5 minutes and the remaining 105 ml was slowly added over 10 minutes. After such time, the mixture was held at 70-75° C. for a further 30 minutes and then allowed to cool to room temperature while stirring was continued. The solid in the reaction flask was filtered and washed with water (250 ml×2), then suspended in methanol (300 ml×2), and again filtered and dried in a vacuum oven at 50° C. overnight. The product was redissolved in CH$_2$Cl$_2$ (300 ml) and filtered off very fine insoluble solid, CH$_2$Cl$_2$ was then removed by rotary evaporator. The yield was 52.0 g (81%). $^1$H and $^{13}$C NMR again provided evidence for a clean expected product while DSC exhibited a sharp melting point at around 133° C. The epoxy equivalent weight of 144-BGOPB was determined to be 226 mol/g.

Figure 9:
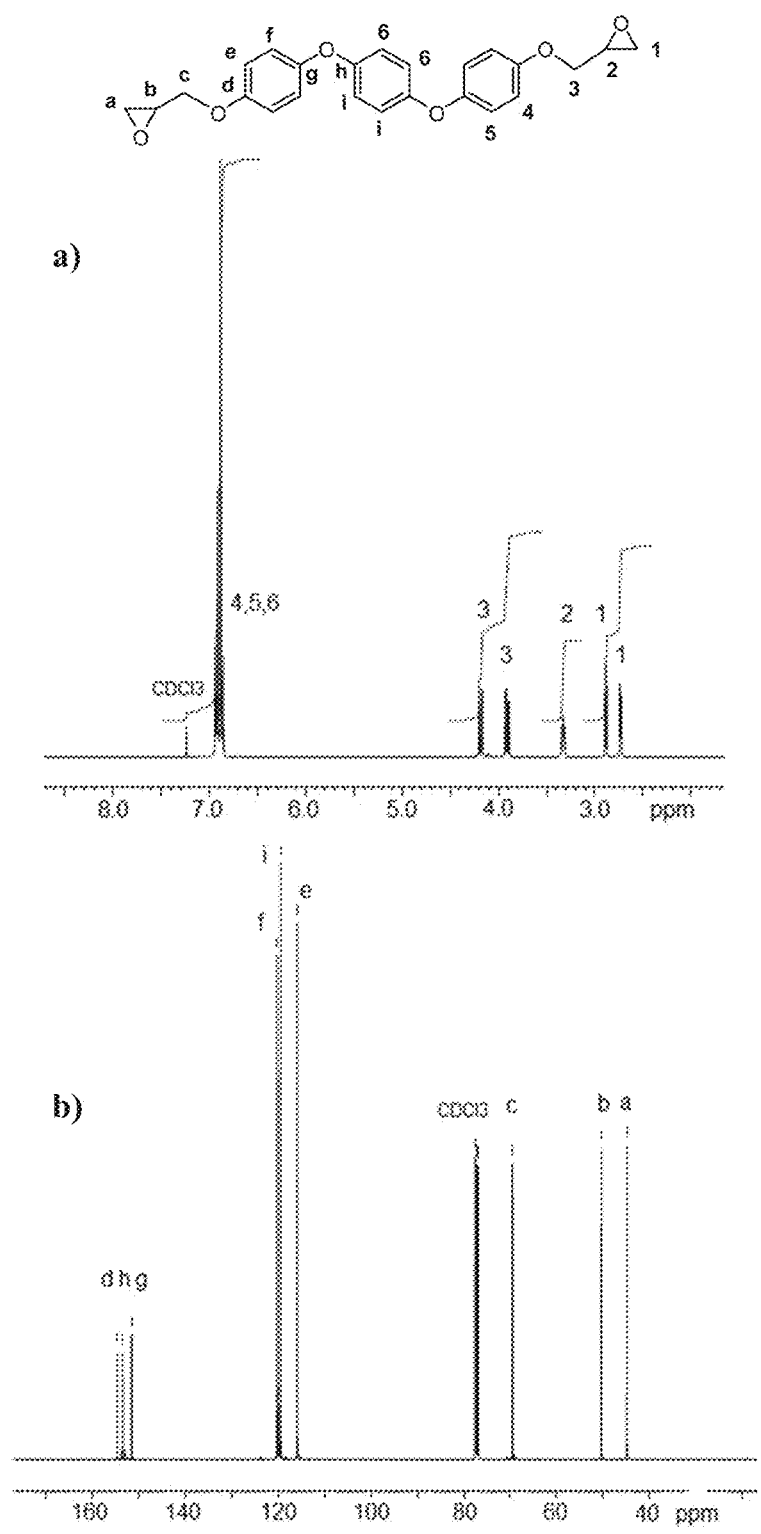
FIG. 9—$^1$H (image a)) and $^{13}$C (image b)) nuclear magnetic resonance spectra for 1,4-bis(4-glycidyloxyphenoxy)benzene.

The proton and carbon NMR spectra shown in FIG. 9, images a) and b), respectively. The spectra show that the product is clean and free of impurities. Each peak can be assigned conveniently to the relevant hydrogen or carbon atom as shown in the insert.

Figure 10:
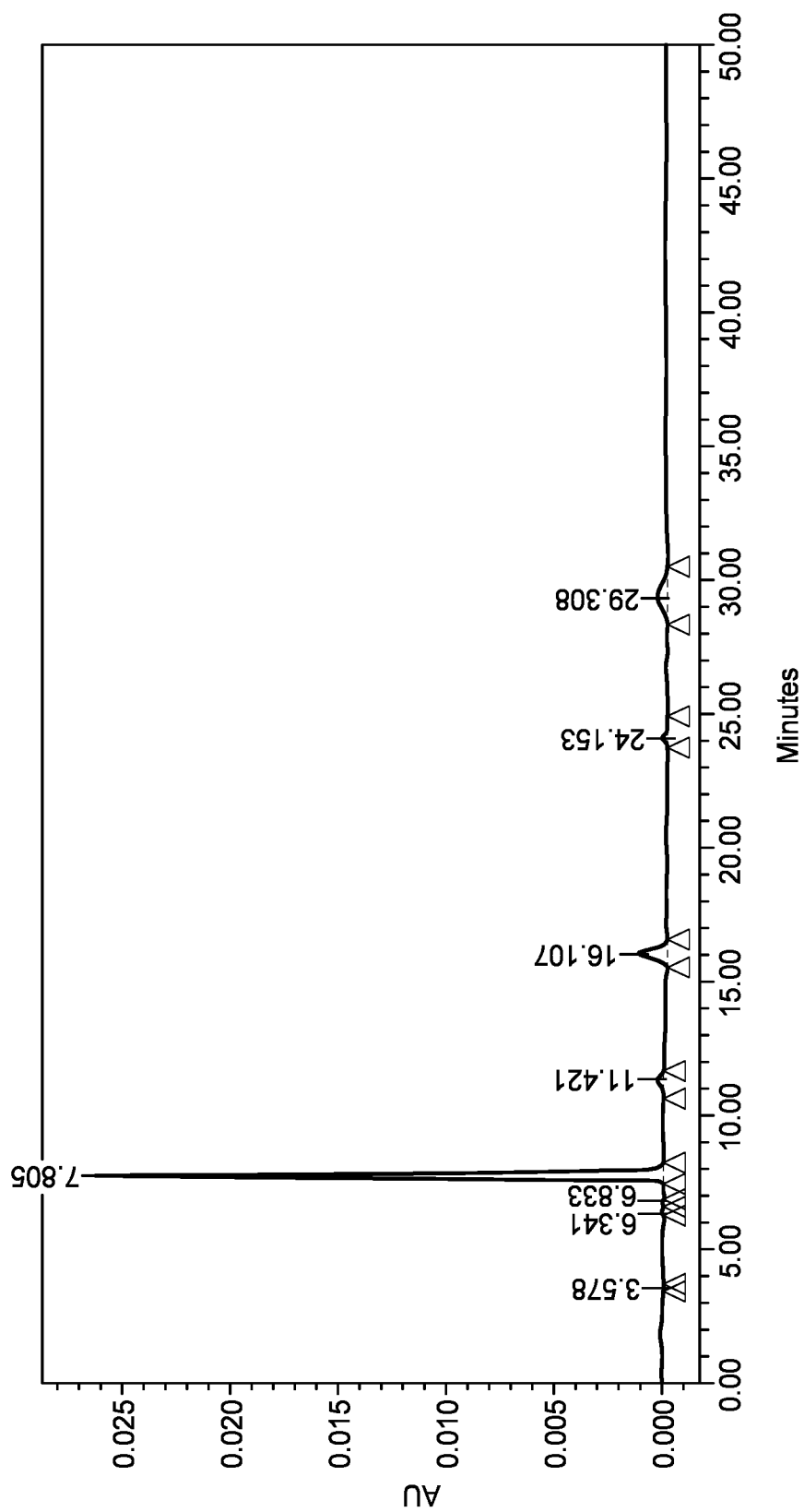
FIG. 10—High performance liquid chromatogram showing the resolution times for components in the synthesis of 1,4-bis(4-glycidyloxyphenoxy)benzene.

The HPLC chromatogram (FIG. 10) also indicates the formation of a pure and single component epoxy resin, although in this example, there is a very modest increase in oligomer formation for this synthetic procedure compared with the 133 BGOPB synthesis as shown by a couple of very small peaks at longer elution times. For the HPLC analysis a 150×4.6 mm Altima C18 column was used. The mobile phase was 65% acetonitrile/water with a flow rate of 1.0 mL min$^{-1}$.

Figure 11:
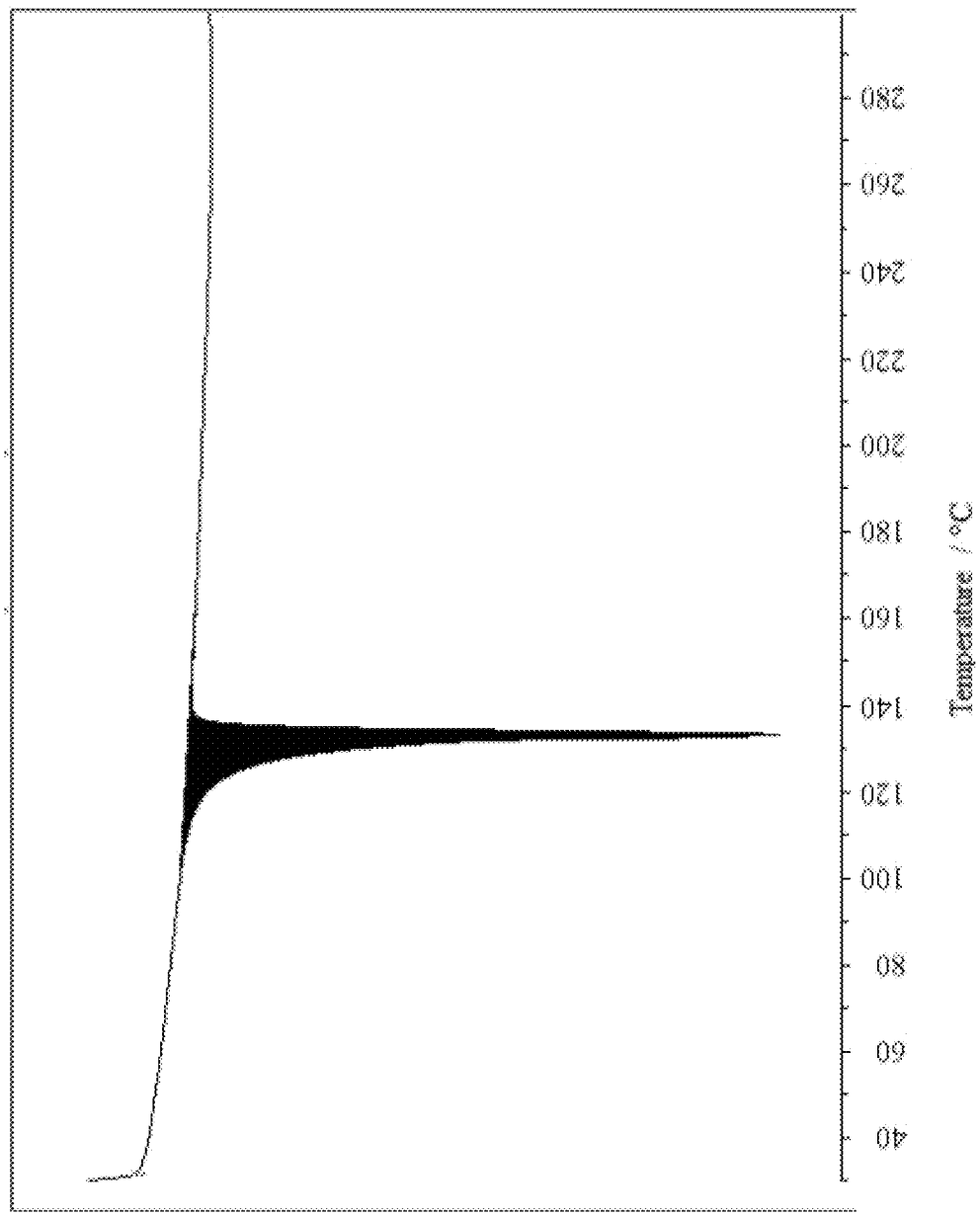
FIG. 11—Differential scanning chromatogram for purified 1,4-bis(4-glycidyloxyphenoxy)benzene.

Since the 144 BGOPB synthesised here was a solid, (indicative of a pure compound) the melting point was determined using DSC as shown in FIG. 11 and was found to be 131° C., certainly a high melting point for typical epoxy resins.

1,3-Bis(4-glycidyloxyphenoxy)benzene (134 BGOPB) can be synthesised using the same process as 44 BGOPB.

Example 6—Synthesis of Meta Substituted
Hydroxy Pre-Cursor to the Epoxy Resin

Step 1—Preparation of the ZnCl$_2$/SiO$_2$ Catalyst

The production of this catalyst was critical to ensure adequate reaction conversion and selectivity. Silica gel-supported zinc chloride was prepared by impregnation of silica gel (Wakogel C-200, 31.7 g) with a solution of anhydrous zinc chloride (5.0 g) in dry methanol (80 ml). The mixture was stirred at room temperature for 0.5 hours and then the methanol was removed using a rotary evaporator. The resulting solid was dried under vacuum (15 mmHg) at 150° C. for 12 hours.

Step 2—Laboratory Scale Synthesis of
Bis(4-hydroxyphenyl)m-xylene (BHPmX)

Phenol (403.30 g, 4.29 moles) and dichloro-m-xylene (75 g, 4.29×10$^{-1}$ moles) were placed in a three necked round bottom flask (3 L). Dichloroethane (1.35 L) was added to the flask and the reaction mixture was stirred in the water bath at ~10° C. under nitrogen. ZnCl$_2$/SiO$_2$ (58.7 g, 8.57×10$^{0.2}$ moles) was added slowly to the reaction mixture and stirred at ~10° C. over 2 hours. During this latter step, at the start, the temperature inside the reaction flask was ~5° C.; after ZnCl$_2$/SiO$_2$ was added into the mixture the temperature was slowly increased to ~10° C. Ice was slowly placed in the water bath in order to maintain the temperature at 10° C.

After 2 hours, the ZnCl₂/SiO₂ was filtered and washed with dichloromethane (100 ml). The solvent was then removed under rotary evaporator (house vacuum first, then oil pump vacuum later). During this state some of the excess phenol was removed with the solvent. The residue oil (product and a lot of excess phenol) was washed with 500 ml hot water (65-70° C.). The washing process was repeated 10 times. Hot water was used in order to effectively remove phenol (8 g phenol/100 ml water at room temperature). The oil became thicker when more phenol removed from the product.

Following the washing, the oil was then redissolved in dichloromethane, dried over Na₂SO₄ (anhydrous) and filtered. The dichloromethane was removed and the product was characterised with NMR, TLC and GC/MS analyses. The yield was normally between 75 to 80%.

It was very difficult to detect <10% phenol in the product by NMR. TLC was the quickest way to check any phenol in the product (silica/CH₂Cl₂ as solvent under UV and iodine, phenol has R$_f$ value ~0.4 to 0.45), but could not determine how many % of phenol presented in the product. GC/MS can be used to check the % of phenol and the % of three isomers in the product but cannot detect the high boiling point oligomer. HPLC will be the best way to determine the % of phenol presented in the product, the three isomers and the oligomer. If the HPLC result showed that there was more than 5% (calculate by % area of the peak) of phenol in the product then the product needs to be washed again with water.

Example 7—Synthesis of Para Substituted Hydroxy Pre-Cursor to the Epoxy Resin

Step 1—Preparation of the ZnCl₂/SiO₂ Catalyst

The catalyst was prepared in the same manner as Step 1 of Example 6.

Step 2—Large Scale Synthesis of Bis(4-hydroxyphenyl)-p-xylene (BHPpX)

Phenol (21.50 kg, 228.57 moles) and dichloro-p-xylene (4.00 kg, 22.86 moles) were placed in a 100 L reaction vessel. Dichloromethane (50 L) was added to the reaction mixture and stirred while the reaction vessel was slowly heated to 40° C. When the temperature inside the reaction vessel reached between 25° C.-30° C., ZnCl₂/SiO₂ (3.13 kg, 4.57 moles) was added slowly to the stirring solution of the reaction mixture and gently refluxed at 35-40° C. over 3 hours. The HCl given off from the reaction need to pass through the sodium hydroxide solution. It was calculated that 4.0 kg scale can produce up to 1170 L HCl gas After 3 hours, the heater was turned off and the volume of the solution inside the reaction vessel was reduced to ~60 L by the vacuum (the original volume was around 70 L). ZnCl₂/SiO₂ was filtered and washed with 2-3 L of dichloromethane (DCM). The dichloromethane solution was stored in buckets (five 20 L buckets) overnight at room temperature. The product precipitated out of DCM solution as a fine white solid which was filtered next day (the filtrate needs to be kept because additional products will be collected from the filtrate later). The white solid product was washed with warm (40-50° C.) water until the pH of the washing solution became neutral. The white solid product was then washed with DCM until the washing solution became colourless (may need to wash between 2 to 3 times). Finally the white solid product was dried in air at room temperature over a weekend. The yield was around 1.8 to 2.0 kg.

The second crop was collected by the following process. The DCM from the filtrate was removed. The residue oil (product and excess phenol) was washed with warm (50-60° C.) water (40 L). The washing process was repeated until the residue oil became a semi solid or a thick paste (may need 7 times of 40 L water). The thick paste was then suspended in DCM (8-10 L) overnight. The product formed as a fine white solid which was filtered and washed with DCM until the washing solution became colourless. The second crop product will have pink colour if the DCM washing is deficient. The white solid product was dried in a vacuum box at room temperature overnight. The yield was around 1.0 to 1.2 kg. The first and second crop products were checked by NMR and HPLC, the total yield was varied between 42 to 48%.

Example 8—Isomer Composition of Bis-hydroxyphenyl-m-xylene (BHPmX) and Bis-hydroxyphenyl-p-xylene (BHPpX)

Figure 12:
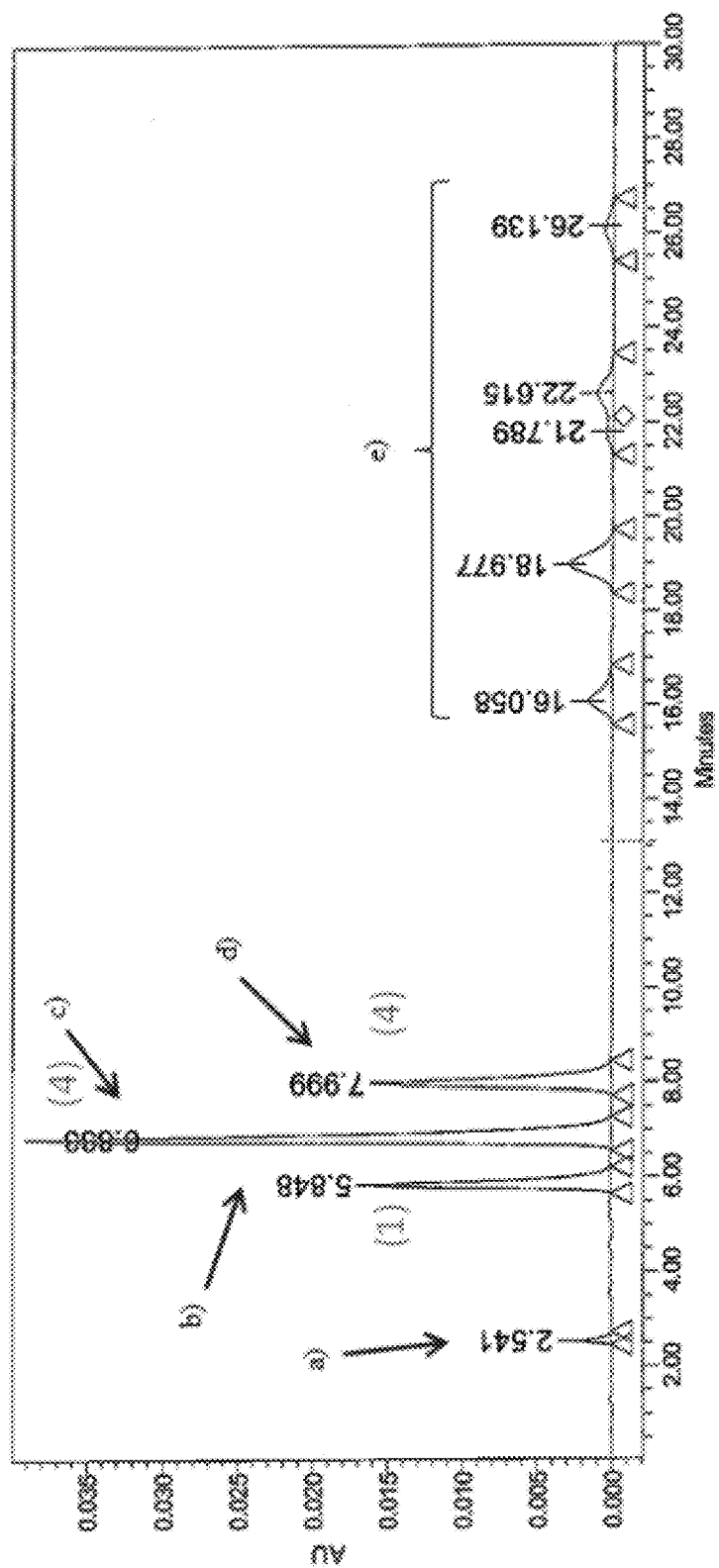
FIG. 12—High performance liquid chromatogram showing the resolution time for isomeric products produced during the synthesis of bis(4-hydroxyphenyl)-m-xylene, wherein: a) indicates phenol; b) indicates the 4,4, isomer; c) indicates the 2,4 isomer; d) indicates the 2,2 isomer; and e) indicates the oligomers.
Figure 13:
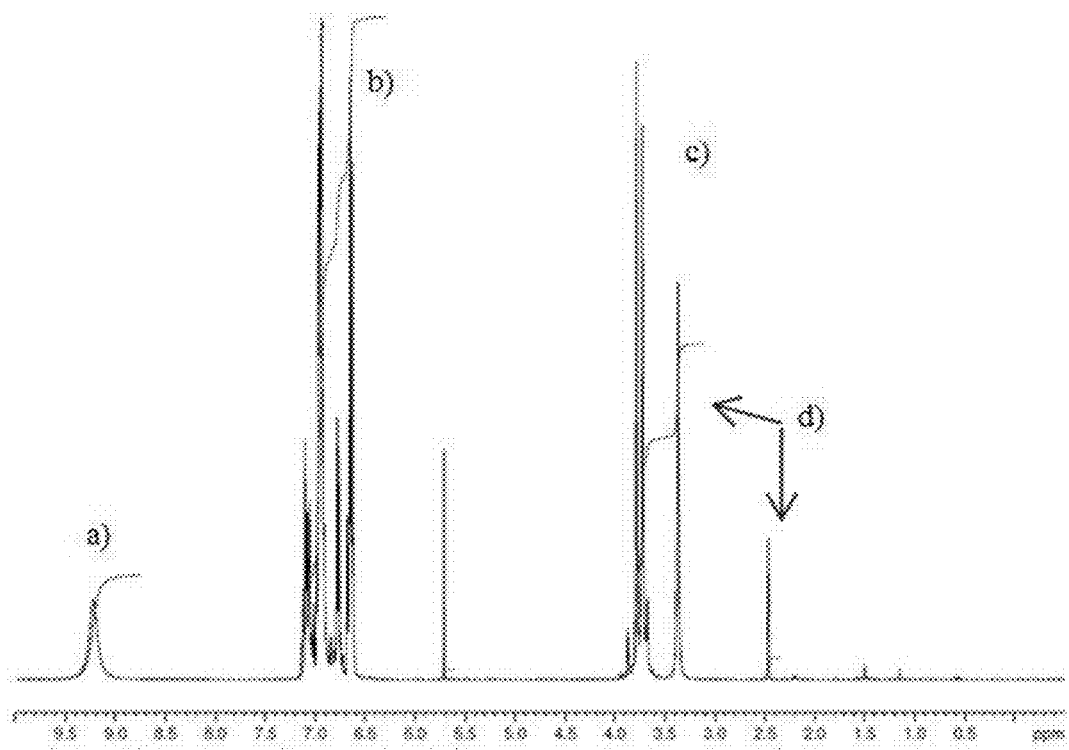
FIG. 13—$^1$H nuclear magnetic resonance spectrum for bis-hydroxyphenyl-m-xylene, wherein: a) represents the two OH groups; b) represents the twelve aromatic C—H groups; c) represents the four aliphatic C—H groups; and d) shows dimethyl sulfoxide (DMSO).

The ortho and para directing nature of the phenol group and the double substitution of the phenol, ensures that a range of isomers of various substitution patterns is expected. This was indeed found to be the case and is shown in a typical HLPC chromatogram in FIG. 12 where three primary peaks are evident. Apart from these peaks, there is some evidence of the phenol starting material and higher molecular weight oligomeric species. Based upon standard geometric considerations the isomers would be expected to consist of the 4,4, 2,4 and 2,2 substituted isomers in a composition 1:4:4 respectively. Clearly this is not what was observed as the composition of these isomers was present in an approximate ratio of 16:43:19. This relative composition was generally found to be present for multiple syntheses of the meta hydroxyl compound. The variation from the expected composition can be explained by steric constraints which promote para substitution in favour of the more difficult ortho substitution. As a result of this the relative concentrations of the 4,4 and 2,4 isomers are increased at the expense of the 2,2 isomer concentration. This is clearly observed to be the case in the HLPC chromatogram shown in FIG. 12. The HLPC trace also shows that the synthesis of the meta hydroxyl compound contains a significant level of higher molecular weight oligomers. The ¹H NMR spectra in FIG. 13 indicates that the compound has been synthesized to a high level of purity.

Figure 14:
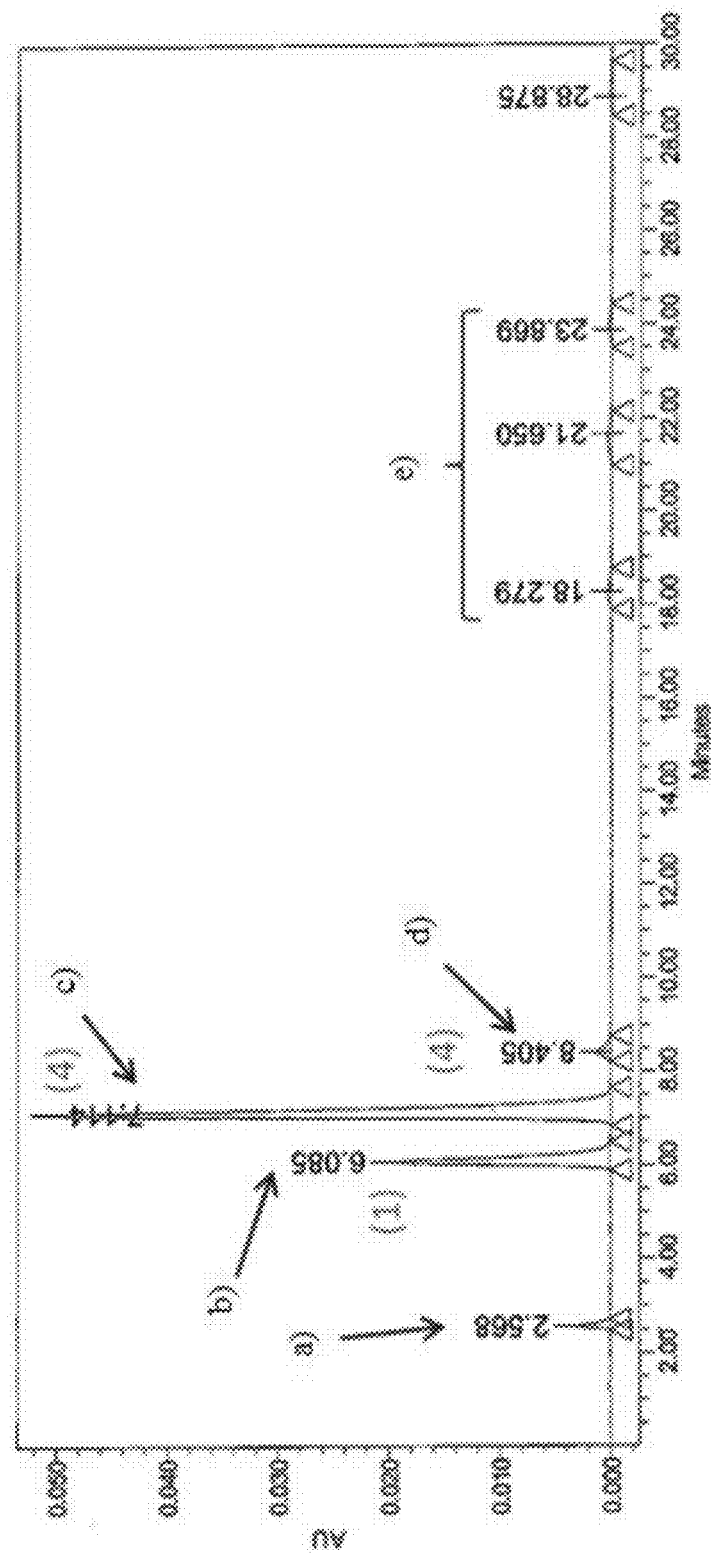
FIG. 14—High performance liquid chromatogram showing the resolution time for isomeric products produced during the synthesis of bis(4-hydroxyphenyl)-p-xylene, wherein: a) indicates phenol; b) indicates the 4,4, isomer; c) indicates the 2,4 isomer; d) indicates the 2,2 isomer; and e) indicates the oligomers.
Figure 15:
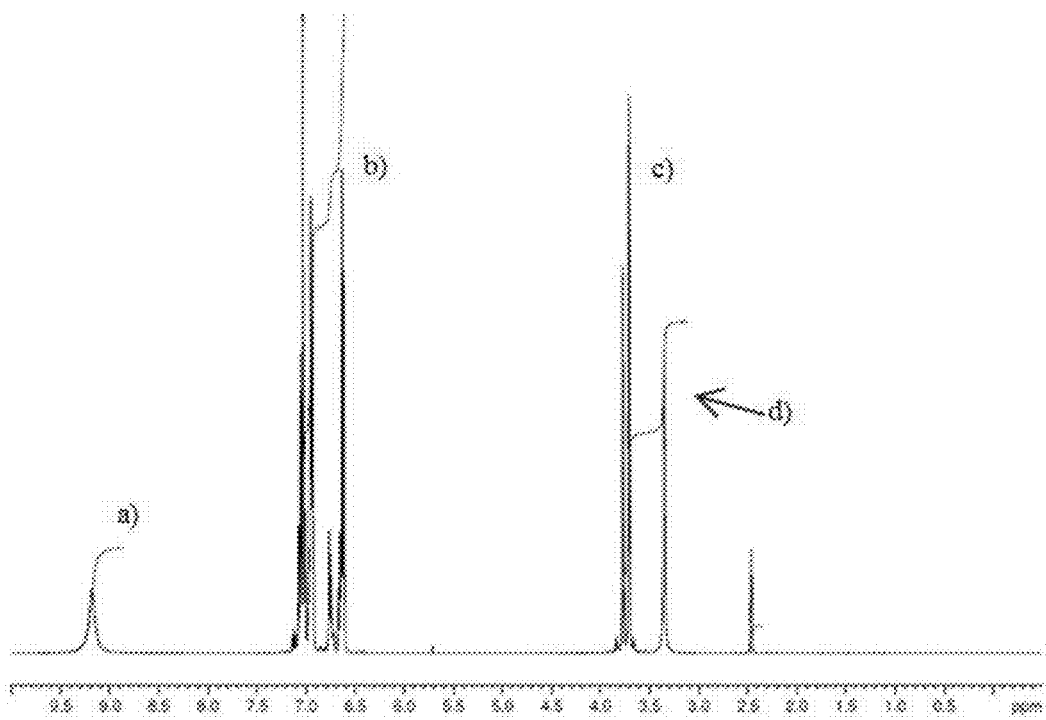
FIG. 15—$^1$H nuclear magnetic resonance spectrum for bis-hydroxyphenyl-p-xylene, wherein: a) represents the two OH groups; b) represents the twelve aromatic C—H groups; c) represents the four aliphatic C—H groups; and d) shows dimethyl sulfoxide (DMSO).

The HPLC trace for the para substituted hydroxyl compound is shown in FIG. 14, where it is observed that there is very little 2,2 isomer present. The differences here between the meta and para substituted xylene synthesis relate to the differing solubilities of the more rigid para substitution of the central phenyl ring compared with the kinked meta substituted hydroxy compound. It was found that the para substituted is less soluble than the meta, and easily precipitated out of solution during the synthesis. This made it easier to isolate, but a disadvantage of this was that the 2,2 isomer remained in solution while and was effectively lost during purification. This is the reason therefore, why there are only two isomers present and why the yield is so much lower than the meta synthesis. Conversely, the advantage of this lack of solubility was the much lower level of oligomer concentration because they were also found to remain in solution. The NMR spectrum shown in FIG. 15 again shows that the para substituted compound had been synthesized to a high level of purity.

Summary of Hydroxy and Epoxy Resin Synthesis

Herein, new epoxy resins made from three benzene groups connected via methylene linkages have been synthesized and characterized for their isomeric composition. The methylene linkages are understood to impart the distortional mobility while the aromatic ring provides thermal stability and resistance to solvent ingress. The structural difference between the bis hydroxyl and epoxy resin derives from the central xylene groups being either meta or para substituted. While not affecting the reaction mechanism to form the molecules the kinked backbone of the meta compound versus the rigid linear backbone of the para compound does have significant impact on the overall product formed. Some of the key experimental aspects of the syntheses that are distinct from the different methods are as follows:

BHPmX
1. After reaction the catalyst is filtered off and the DCM is evaporated completely.
2. The oily product is continuously washed with water to remove phenol. This is an advantage as it helps the washing progress in removing phenol.
3. Final product is an oil containing 3 isomers, high molecular weight oligomers and yield of about 75% in the laboratory.

BHPpX
1. After reaction, catalyst is filtered off and DCM volume is reduced until the product beings crystallizing out of solution.
2. The product is filtered to produce a white solid with 3 isomers. However, the third isomer, the 2,2 substituted isomer is present in extremely low concentrations.
3. Final product has a yield of about 50% and very little evidence of higher molecular weight oligomers.

Example 9—Scale Up Synthesis of Bis(hydroxy phenyl)-p-xylene (BHPpX)

Figure 16:
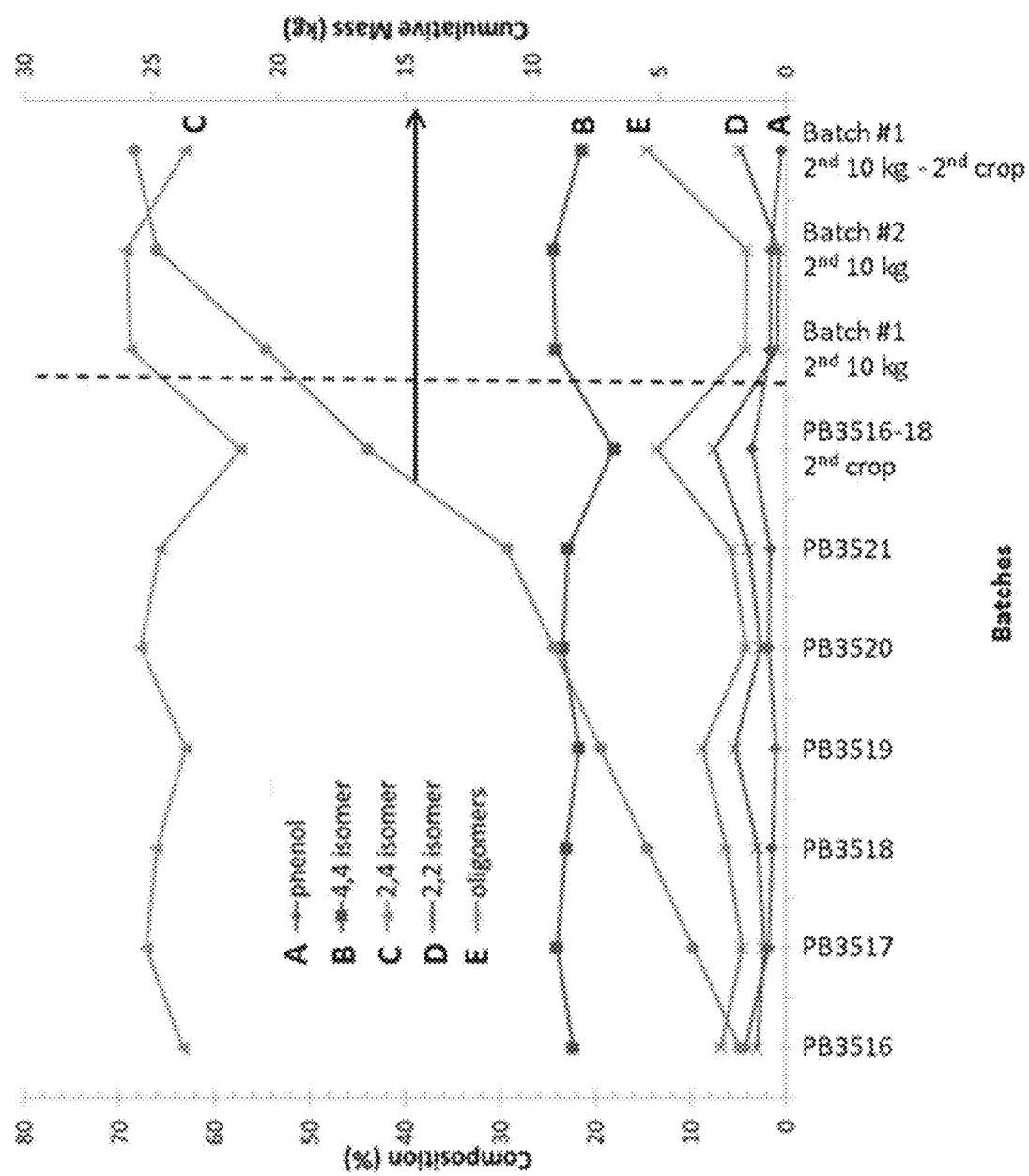
FIG. 16—A plot of the respective concentrations of different isomers, phenol and oligomeric species, during the synthesis of bis(hydroxy phenyl)-p-xylene.

26 kg of the para-hydroxyl compound was synthesized during three separate periods in a CSIRO pilot plant. The first was a 1 kg trial run to optimize conditions, the second period prepared 16.2 kg while the third period made about 10 kg. During scale up, however, between 2 and 4 kg of product were prepared on each occasion due to the manufacturing constraints of the pilot plant. Each batch prepared was characterized according to HPLC to determine the isomeric compositions. FIG. 16 shows a plot of the respective concentrations of the different isomers including the phenol starting reactant and the oligomeric species. During the scale-up synthesis, it was typical to obtain a second crop from the filtrate, for the product that was more miscible than the first product which initially precipitated. These products are noticeable in that their isomeric compositions are affected by the higher levels of oligomers and increased content of the 2,2 substituted isomer, as would be expected. This is important in that it shows that the 2,2 substituted isomer is in fact synthesized, but is simply more soluble in the solvent, so does not precipitate in the first instance.

Example 10—Curing and Characterisation of the Carbonyl Linked Aromatic Amines, 1,3-bis(3-aminobenzoyl)benzene (133 BABB), 1,3-bis(4-aminobenzoyl)benzene (134 BABB) and 1,4-bis(4-aminobenzoyl)benzene (144 BABB)

Preparation of Resins

A series of epoxy/amine formulations were blended in a 1:1 epoxide to amino stoichiometric formulation and mixed and degassed on a rotary evaporator using an oil bath at a temperature of 110° C.

The epoxy resins used were:
diglycidyl ether of bisphenol A (BisA);
diglycidyl ether of bisphenol F (BisF); and
1,4 bis(4-glycidyl ether phenoxy) benzene (144 BGOPB).

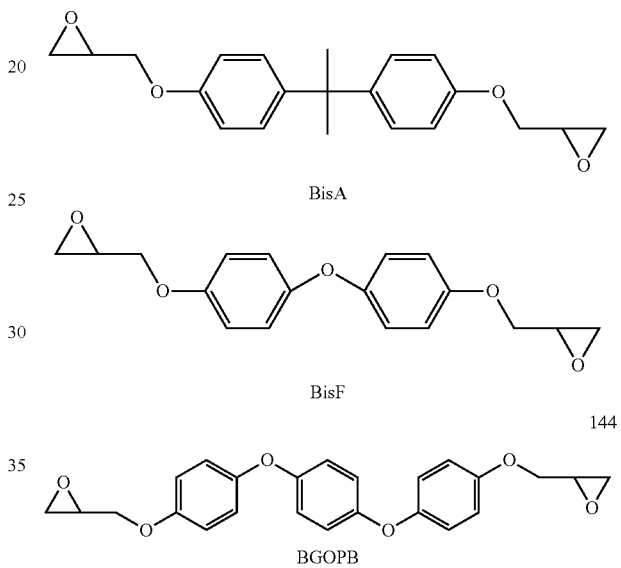

The amines used were based on Compounds of Formula 4':

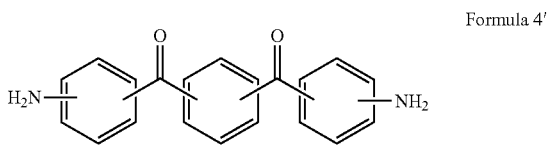

Formula 4'

Specifically, the amines tested were:
1,3-bis(3-aminobenzoyl)benzene (133 BABB);
1,3-bis(4-aminobenzoyl)benzene (134 BABB); and
1,4-bis(4-aminobenzoyl)benzene (144 BABB).

Given the potentially reactive nature and lack of miscibility in some of the formulations, mixing was generally stopped as soon as it was clear that the amine had fully dissolved in the epoxy resin and was free of bubbles.

The resin was then poured into preheated silicon moulds for flexural testing and dynamic mechanical thermal analysis. The moulds were preheated at 110° C. for a minimum of 1 hour. The epoxy resin was then cured in an air circulating ovens typically at 177° C. for 10 hours, and post-cured at 210° C.

Table 3 shows exemplary BABB based resins that were produced. In each case the cure profile was 177° C. for 10 hours and then 210° C. for 2 hours.

TABLE 3

Conditions and compounds used for the production of cured compositions.

| Epoxy resin | Amine | Cure Profile | Stoichiometry |
|---|---|---|---|
| BisA | 133 BABB | 177° C. for 10 hours/210° C. for 2 hours | 1:1 |
| BisF | 133 BABB | 177° C. for 10 hours/210° C. for 2 hours | 1:1 |
| 144 BGOPB | 133 BABB | 177° C. for 10 hours/210° C. for 2 hours | 1:1 |
| BisA | 134 BABB | 177° C. for 10 hours/210° C. for 2 hours | 1:1 |
| BisF | 134 BABB | 177° C. for 10 hours/210° C. for 2 hours | 1:1 |
| 144 BGOPB | 134 BABB | 177° C. for 10 hours/210° C. for 2 hours | 1:1 |
| BisA | 144 BABB | 177° C. for 10 hours/210° C. for 2 hours | 1:1 |
| BisF | 144 BABB | 177° C. for 10 hours/210° C. for 2 hours | 1:1 |
| 144 BGOPB | 144 BABB | 177° C. for 10 hours/210° C. for 2 hours | 1:1 |

Characterisation

Figure 17:
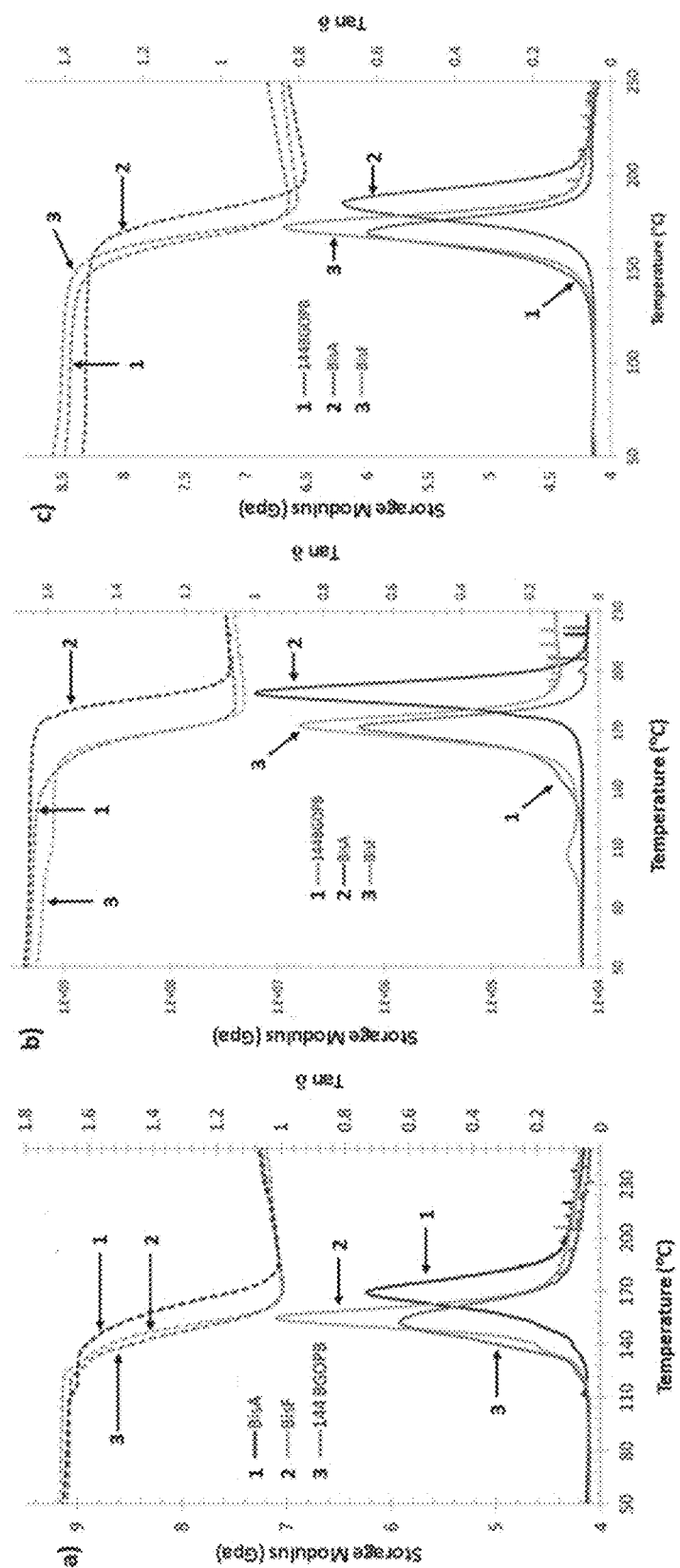
FIG. 17—Dynamic mechanical thermal analysis (DMTA) spectra of: diglycidyl ether of bisphenol A (BisA), diglycidyl ether of bisphenol F (BisF) and 1,4 bis(4-glycidyl ether phenoxy) benzene (144 BGOPB) networks cured with a) 1,3-bis(3-aminobenzoyl)benzene (133 BABB), b) 1,3-bis(4-aminobenzoyl)benzene (134 BABB) and c) 1,4-bis(4-aminobenzoyl)benzene (144 BABB).

Dynamic mechanical thermal analysis (DMTA) spectra are shown in FIG. 17 exhibit fairly typical behaviour for high performance epoxy networks. The tan δ spectra in particular, appear to be sharp and symmetric, often ascribed to being quite homogenous and free from large amounts of chemical defects. The 133 BABB produces the network with the lowest Tg of the order of 140-170° C. (tan δ max) while the 144 BABB cured networks give the highest, being around 160-200° C. The Tg values for the 134 BABB cured networks are quite similar to the 144 BABB, suggesting that the Tg values are dominated by the substitution patterns on the outer aromatic ring. The effect of the different epoxy resins followed the same pattern for each of the amines. The BisA resin gave the highest Tg value, followed by the 144 BGBOP and the BisF which gave similar Tg values regardless of the amine.

Figure 18:
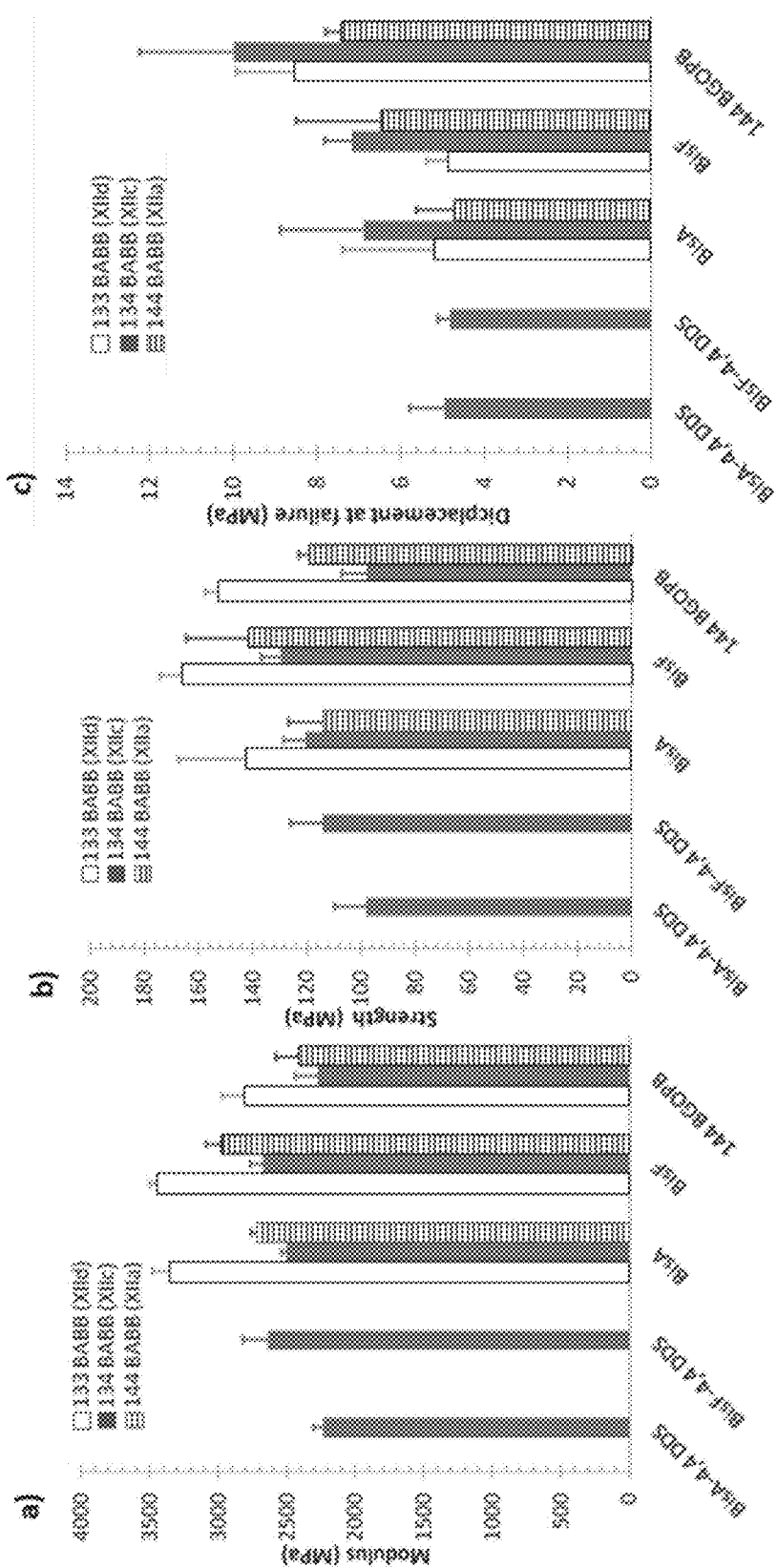
FIG. 18—a) Flexural modulus, b) strength and c) displacement at failure of BisA, BisF and 144 BGOPB networks cured with 133 BABB, 134 BABB and 144 BABB.

The flexural properties of the cured networks are compared against each other in FIG. 18. In this case the results were also compared with BisA and BisF resins cured with 4,4-diaminodiphenylsulfone (44 DDS). As shown, the compressive moduli and strength properties for the BABB cured networks are at least as good as for the BisA and BisF resins, and in fact, show excellent enhancement when cured with the 133 BABB amine. This is somewhat surprising as the meta substituted networks generally have lower glass transition temperatures. The displacement at failure also suggest increased ductility, thus curing the BABB amines with the different epoxy resins has produced networks that have both improved strength, stiffness and ductility, properties that typically do not improve concurrently.

Figure 19:
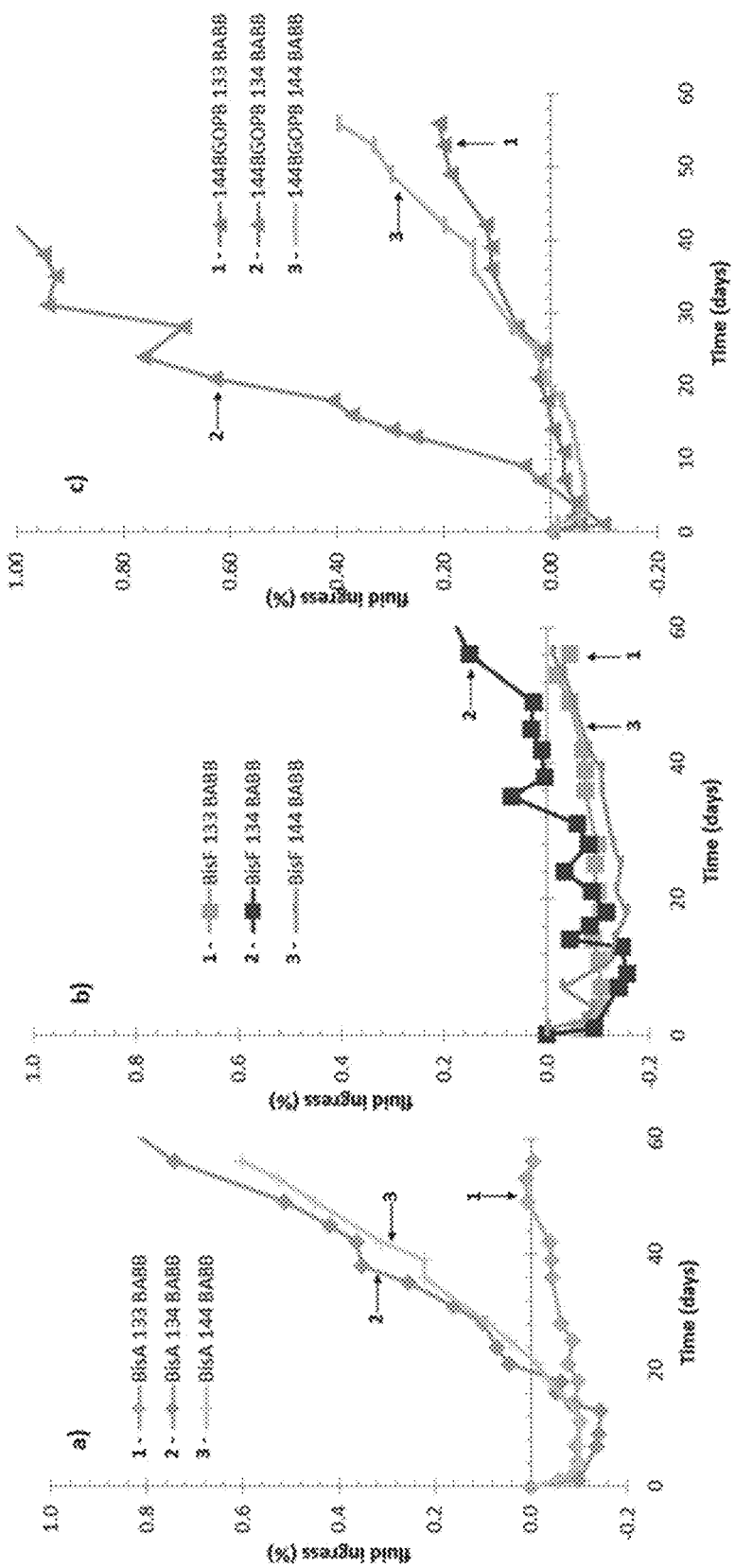
FIG. 19—Methyl ethyl ketone (MEK) ingress as a function of time for 133, 134 and 144 BABB networks cured with a) BisA, b) BisF and c) 144 BGOPB.

FIG. 19 shows results obtained for weight gain during immersion of the cured epoxy networks in methyl ethyl ketone (MEK). Overall, the results show the resistance to MEK uptake by the BABB cured networks. The networks cured with 133 BABB provide the greatest extent of chemical resistance. The greatest resistance to MEK ingress is achieved using BisF followed by 144 BGBOP, then BisA.

Example 11—Curing and Characterisation of the Methylene Linked Aromatic Epoxy Resins, bis amines, 1,3-bis(3-aminobenzoyl)benzene (133 BABB), 1,3-bis(4-aminobenzoyl)benzene (134 BABB) and 1,4-bis(4-aminobenzoyl)benzene (144 BABB)

Preparation of Resins

The formulations used diglycidyl ether of bisphenol F (BisF), bis[(glycidylether)phenyl)]-m-xylene (BGOPmX), bis[(glycidylether)phenyl)]-p-xylene (BGOPpX) and diglycidyletherbiphenyl (BGOBP).

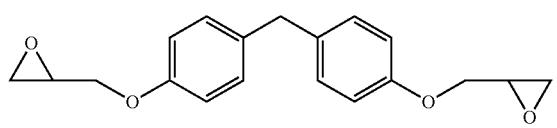

Diglycydyl ether of Bisphenol F

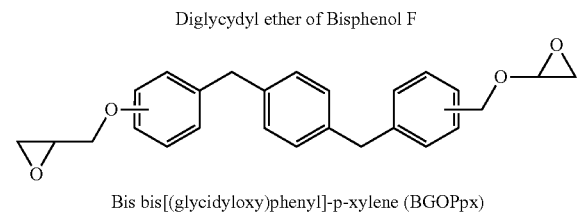

Bis bis[(glycidyloxy)phenyl]-p-xylene (BGOPpx)

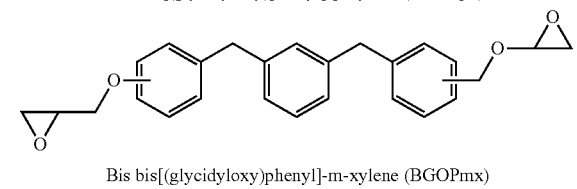

Bis bis[(glycidyloxy)phenyl]-m-xylene (BGOPmx)

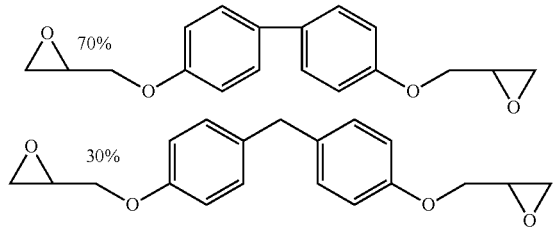

The amine hardeners used to cure the epoxy resins were 4,4 diamino diphenyl sulphone (44 DDS) and methylene dianiline (MDA).

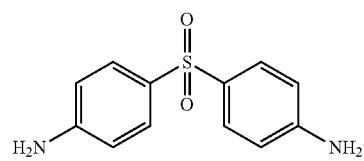

4,4 diamino diphenyl sulphone

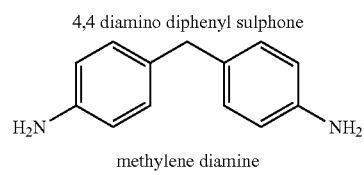

methylene diamine

Sample Preparation

The epoxy resins were conditioned at 100° C. for approximately half an hour before mixing together on a rotary evaporator under vacuum at about 120° C. They were then placed into a vacuum oven set at approximately 95° C. and −100 kPa for 1 hour to minimise the level of dissolved gas. The hardener was then added to the epoxy such that the overall stoichiometry was 1:1 epoxide:amino groups and mixing continued on the rotary evaporator until the hardener had dissolved into the epoxy resin. This continued for approximately 1-2 hours depending upon the reactivity of the formulation. During this time, Teflon coated moulds were preheated at 120-150° C. for 4 hours so that when mixing was complete, the resin samples were poured into the Teflon moulds and cured in an air circulating oven. As a result of the higher reactivity of the MDA system, they were cured at 150° C. for 12 hours, followed by a 3 hour post-cured at 177° C., while the less reactive 4,4 DDS systems were cured at 177° C. for 12 hours, followed by a 3 hour post-cured at 205° C.

To achieve an evenly cured and homogenous network it was necessary to be very scrupulous about ensuring that the hardener was completely dissolved in the epoxy resin prior to cure. This was the case, even if higher temperature was required to dissolve the amine. If this was not done properly, heterogeneous networks with very poor properties were achieved. In addition to this, the BGOBP epoxy resin was a solid at room temperature so it was necessary to blend it with 30 mol % BisF epoxy to improve processability.

A list of the samples prepared in this program and their cure profile and post-cure regimes are shown in Table 4.

TABLE 4

Epoxy/Amine formulations and their cure profiles prepared in Example 11.

| Sample ID | Formulation | Cure and Post-Cure Profile |
|---|---|---|
| 1 | BGOPpX/44 DDS | 177° C. 12 hours/205° C. 3 hours |
| 2 | BGOPpX/MDA | 150° C. 12 hours/177° C. 3 hours |
| 3 | BGOPmX/44 DDS | 177° C. 12 hours/205° C. 3 hours |
| 4 | BGOPmX/MDA | 150° C. 12 hours/177° C. 3 hours |
| 5 | BisF/MDA | 177° C. 12 hours/205° C. 3 hours |
| 6 | BisF/44 DDS | 150° C. 12 hours/177° C. 3 hours |
| 7 | (70 mol % BGOPmX-30 mol % BisF)/44 DDS | 177° C. 12 hours/205° C. 3 hours |
| 8 | (70 mol % BGOPmX-30 mol % BisF)/MDA | 150° C. 12 hours/177° C. 3 hours |

Characterisation

Figure 20:
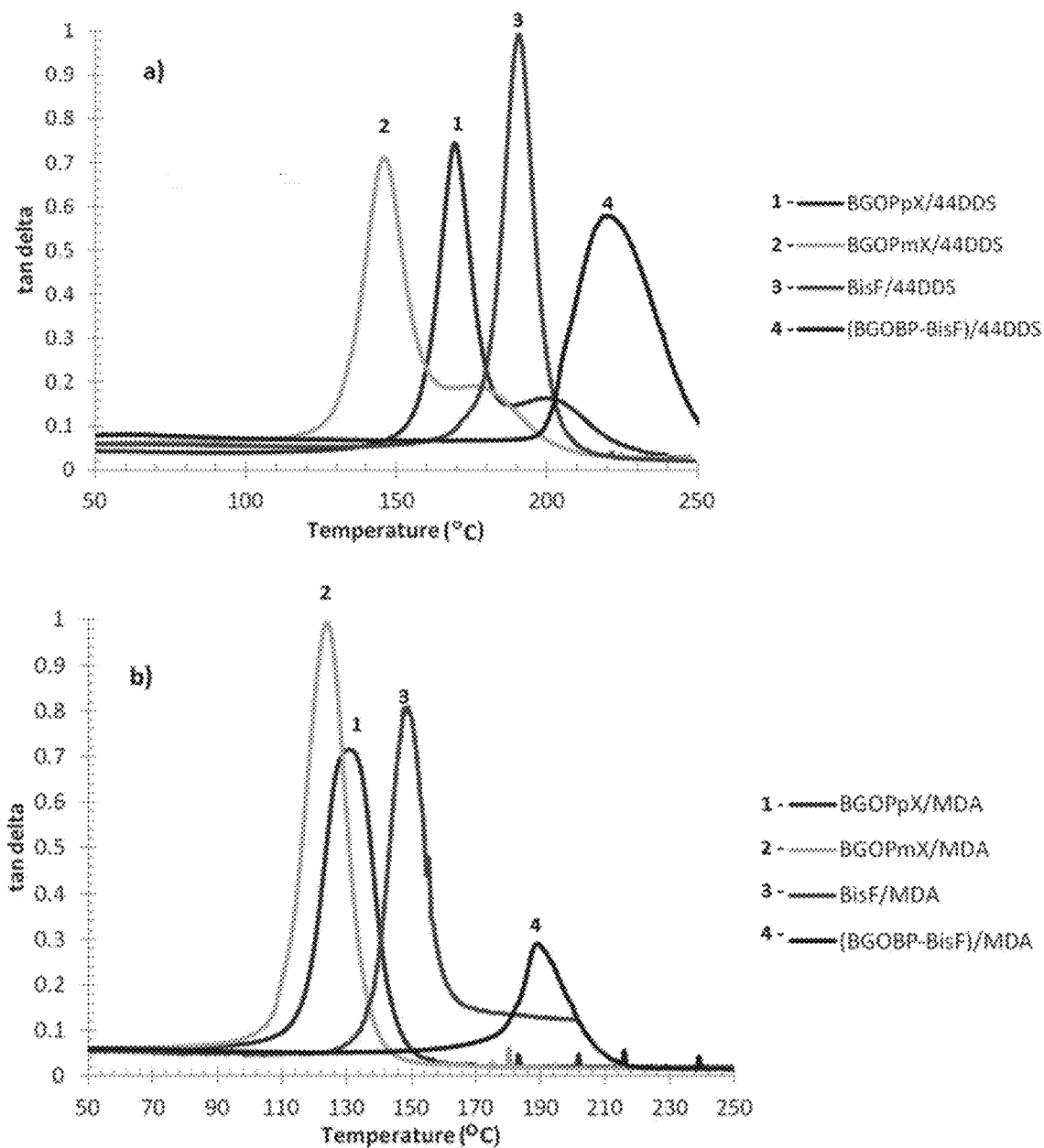
FIG. 20—DMTA tan delta traces showing the variation in Tg for different epoxy resins after curing with a) 44 DDS and b) MDA. The cure was 150° C. for 12 hours and post-cured at 177° C. for 3 hours.

DMTA analysis is shown in FIG. 20 shows that for the 44 DDS and MDA cured systems respectively the Tg values follow a trend with the BGOPmX having the lowest Tg followed by BGOPpX, BisF and finally the BGOBP blended formulation with the highest, despite containing 30 mol % of the BisF epoxy resin. The tan δ traces are observed to be quite symmetrical and homogenous, indicative of a simple curing mechanism for both MDA and 4,4 DDS based systems. However, it should be noted that for the 44 DDS cured systems, the epoxy resins, do display a smaller peak at higher temperatures above the Tg which is exacerbated at higher cure temperatures and also increases with continued post-curing. The peaks in the tan δ spectra are shown in Table 5 for the 44 DDS and MDA systems and confirm that the Tg values are similar to what was found previously.

TABLE 5

Tg values after cure as measured from the tan delta spectra for the 44 DDS and MDA cured systems of Example 11

| Sample | Tg (° C.) Cured |
|---|---|
| BGOPpX/44 DDS | 169.7 |
| BGOPpX/MDA | 128.9 |
| BGOPmX/44 DDS | 144.6 |
| BGOPmX/MDA | 122.3 |
| BisF/MDA | 147.7 |
| BisF/44 DDS | 189.7 |
| (70 mol % BGOPmX-30 mol % BisF)/44 DDS | 217.0 |
| (70 mol % BGOPmX-30 mol % BisF)/MDA | 187.1 |

Figure 21:
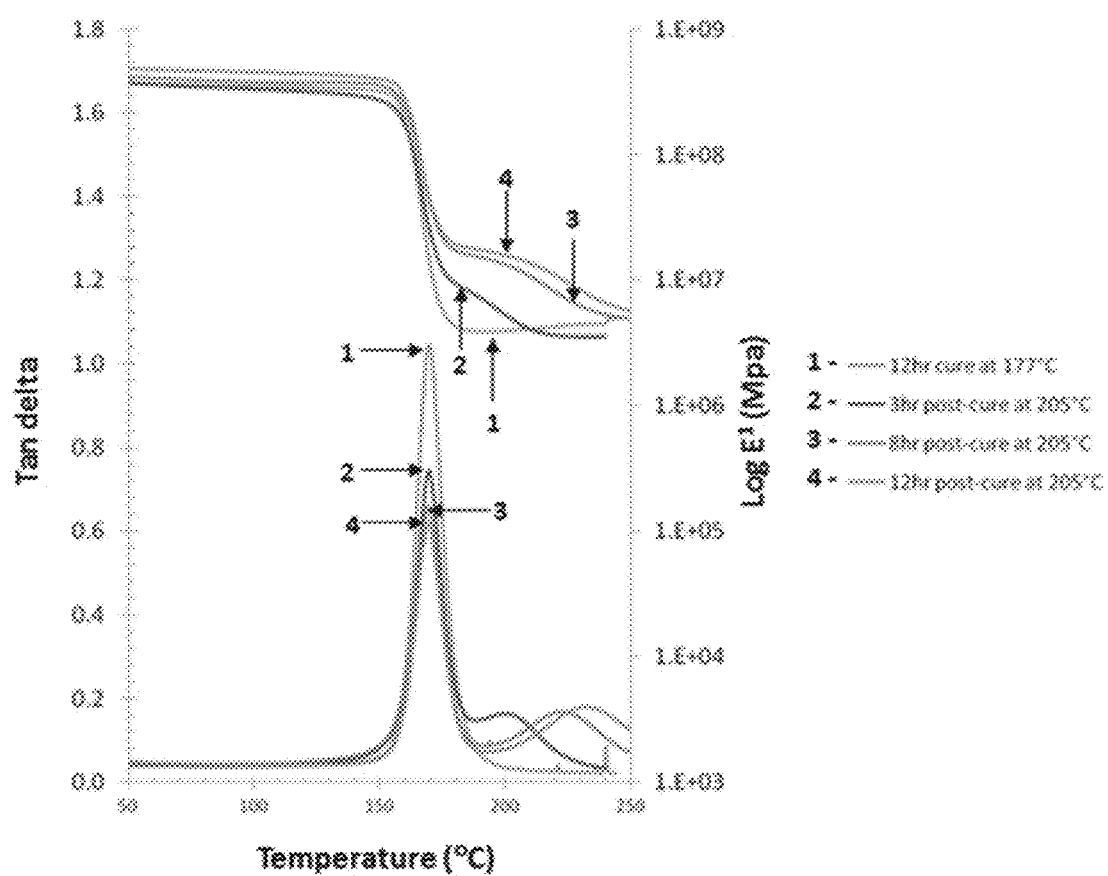
FIG. 21—DMTA spectra of BGOPpX/44 DDS cured networks after curing at different post-curing temperatures.

FIG. 21 shows the impact of varying post-curing on the DMTA spectra. As can be seen, there is negligible effect upon the Tg of the network, though there is some additional reaction occurring in the rubbery region at higher temperatures. The consistency of the Tg values suggests that the cure mechanism is very robust and stable.

Figure 22:
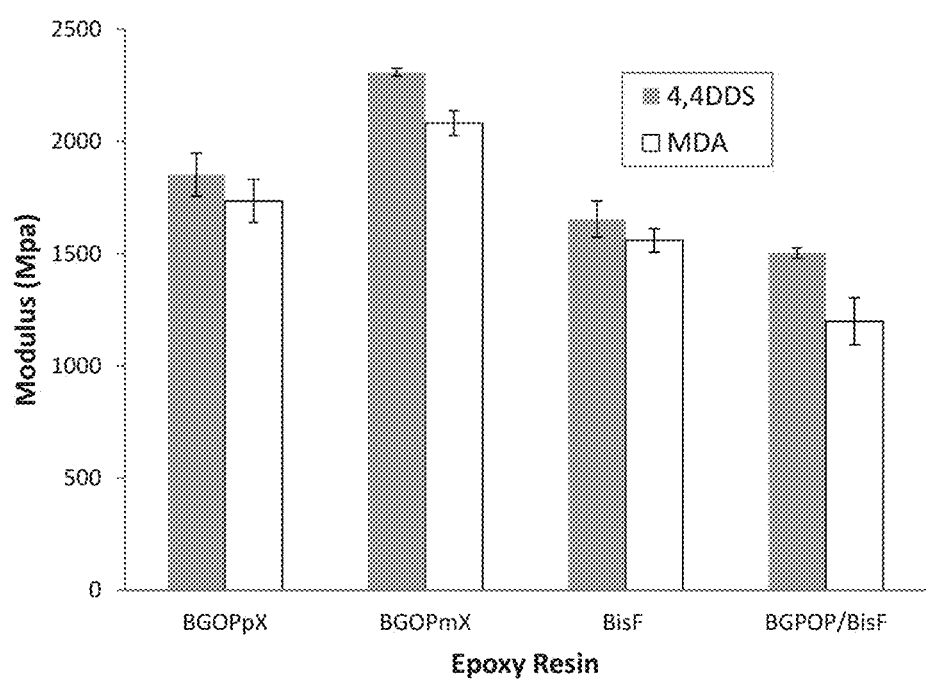
FIG. 22—Plot of modulus of post-cured systems incorporating 44 DDS and MDA hardeners.
Figure 23:
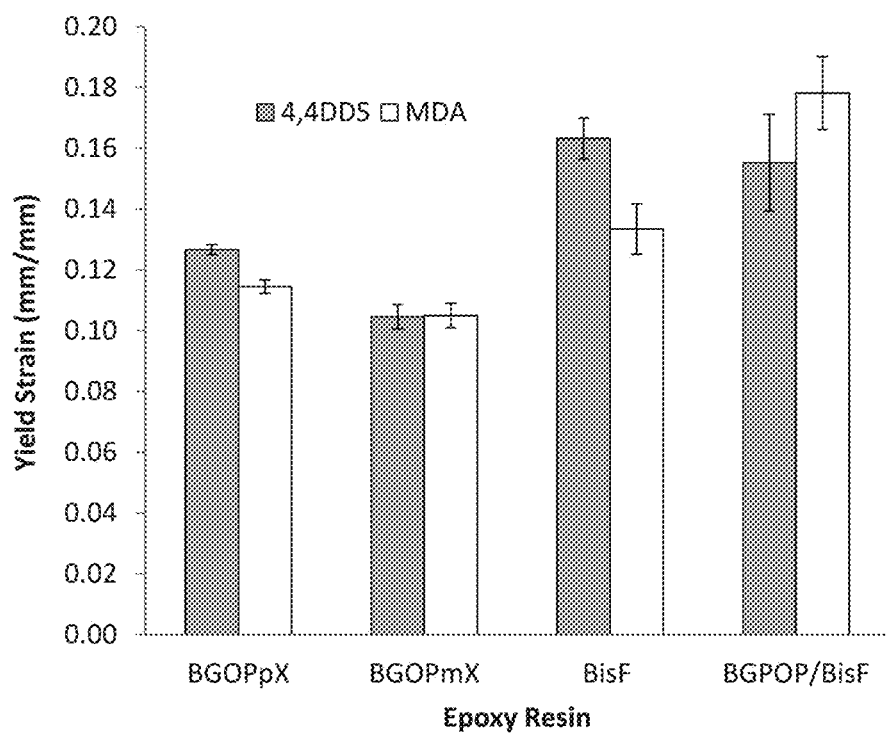
FIG. 23—Plots of a) yield strain and b) yield stress of post-cured systems for both 44 DDS and MDA hardeners.
Figure 23:
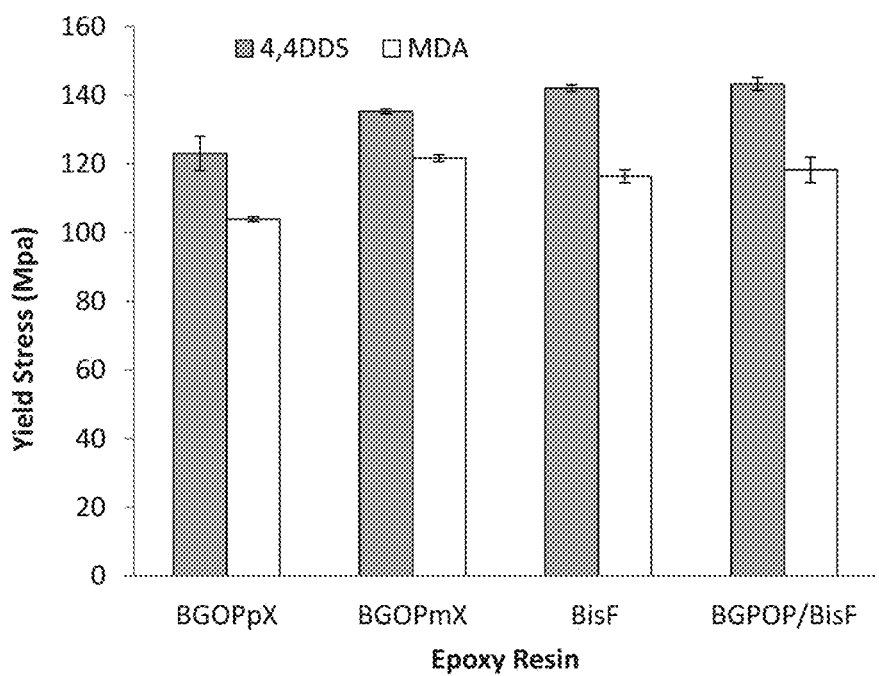

The compressive properties measured for each of the networks are shown in FIG. 22 and FIG. 23. The modulus results in FIG. 22 reveal that the BGOPmX produces the highest modulus followed by the BGOPpX network and then the BisF network. The modulus of the rigid rod biphenyl polymer network is the lowest of them all. These results arise from the fact that modulus in glassy polymers is controlled by short range motions, free volume and packing densities rather than crosslink densities.

In the case of BGOPmX, meta substitution results in a backbone structure which is likely to provide better packing, reduced free volume and hence higher modulus. The BGOPpX para substituted network is a more rigid polymer network and as a consequence has a somewhat lower modulus. The biphenyl based network, as can be imagined has even poorer packing density arising from its rigid structure, producing high free volume, lower density and much lower modulus. In contrast, the yield strain and stress are more controlled by longer range factors such as crosslink density and as a consequence the these parameters are significantly lower for the BGOPpX and BGOPmX epoxy resins compared with the BisF and rigid rod biphenyl network polymers.

Figure 24:
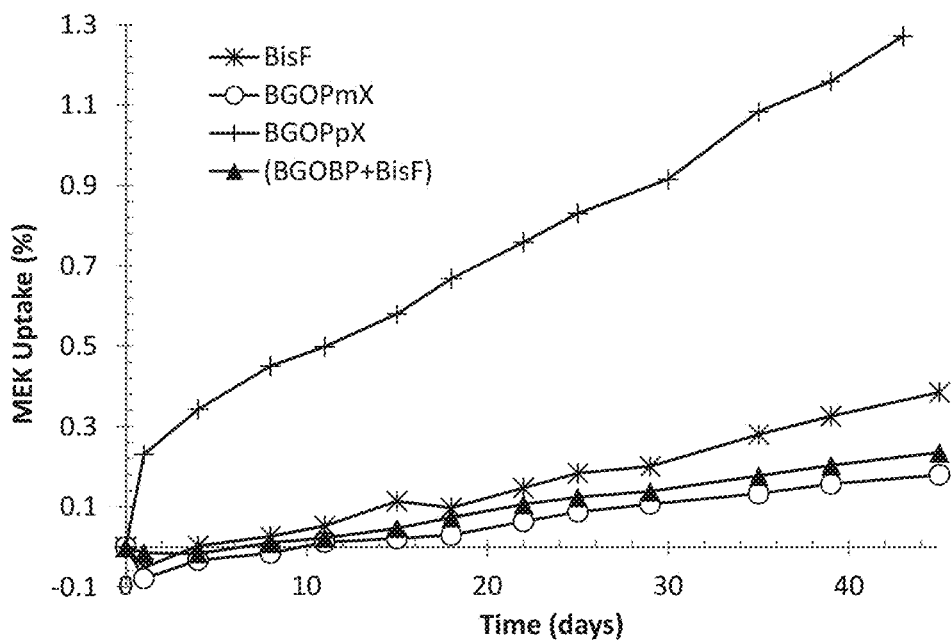
FIG. 24—Plot of the solvent ingress as a function of time utilising MEK at room temperature for a) 44 DDS and b) MDA cured networks.
Figure 24:
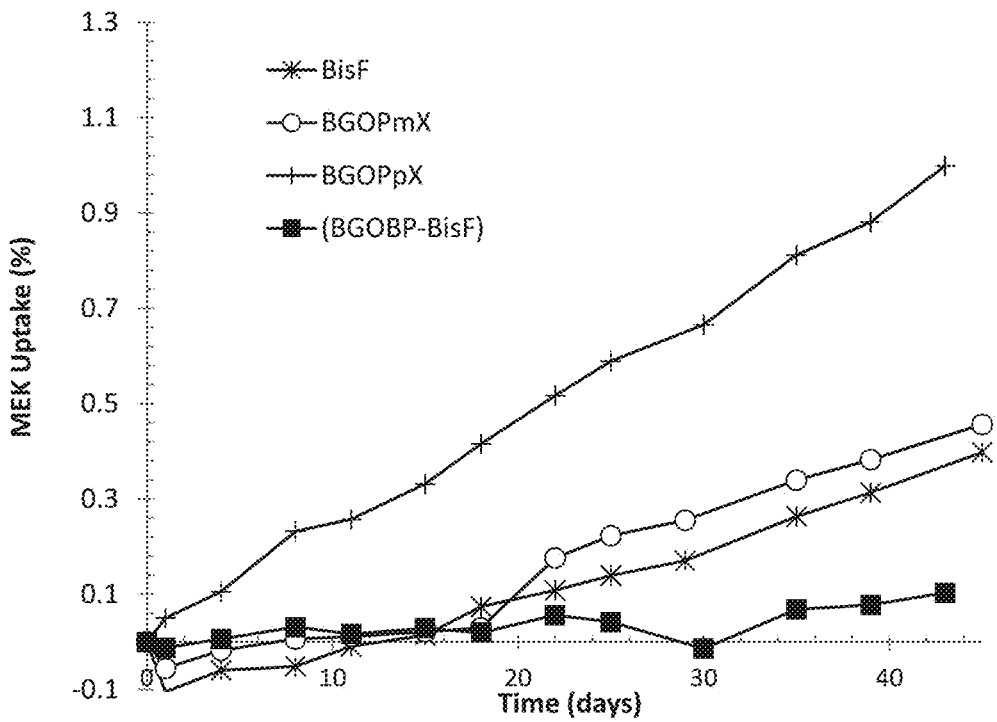

Samples similar to those used for compression measurements were placed in MEK and Skydrol (Solutia Inc.) at room temperature for a period of about 45 days and the weight uptake was measured at appropriate time intervals. FIG. 24 a) and b) show the results obtained for each system cured with 44 DDS and MDA respectively and indicate that both the biphenyl and the BGOPmX epoxy resins cured with 44 DDS reduce the level of MEK absorbed compared with commercially available BisF/44 DDS systems. The results are similar for the corresponding MDA networks, though the BGOPmX network is slightly above the BisF rather than slightly below in this instance. An important result from this study, however is that the BGOPpX, has a much higher level of MEK uptake compared with BisF regardless of which amine was used. This can be explained by an expected higher free volume arising from the reducing packing efficiency, itself deriving from the more rigid and linear nature of the para substituted network structure.

Example 12—Curing and Characterisation of 1,4-bis(4-glycidyloxyphenoxy)benzene (144 BGOPB) and 1,3-bis(3-glycidyloxyphenoxy)benzene (133 BGOPB) cured with 44 diamino diphenyl sulphone (44 DDS) and Compared Against Diglycidyl Ether of Bis Phenol A (BisA) and diglycidyl ether of bis phenol F (BisF) Cured with 44 diamino diphenyl sulphone (44 DDS)

Sample Preparation

The epoxy resins 144-BGOPB and 133-BGOPB were each placed in a round bottom flask in an oil bath at about 140° C. (133-BGOPB) and 145° C. (144-BGOPB) and degassed for 5 minutes on a rotary evaporator. 4,4 diamino diphenyl sulphone (44 DDS) (or 3,3 diamino diphenyl sulphone (33 DDS)), was then added slowly over a period of about 10 minutes and mixing continued until the resin was clear and free of bubbles. The composition was such that the epoxy amine resin was at all times a 1:1 stoichiometric blend. The resins were then poured into Teflon coated moulds that had been pre-heated to 150° C. and cured in an air circulating oven. The formulations prepared and their respective cure profiles are listed in Table 6.

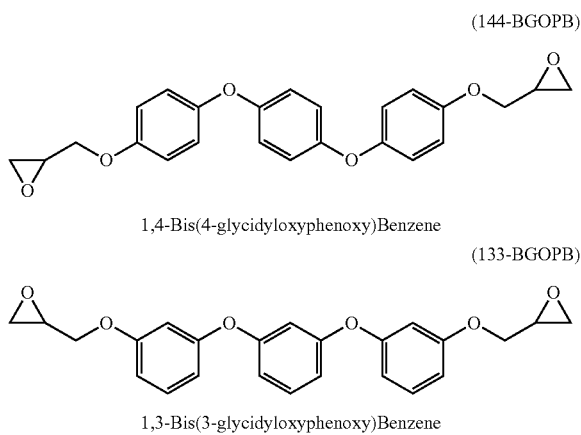

(144-BGOPB)
1,4-Bis(4-glycidyloxyphenoxy)Benzene (133-BGOPB)
1,3-Bis(3-glycidyloxyphenoxy)Benzene

TABLE 6

Cure profile and characterisation methods applied to second generation distortional and BisF epoxy resins.

| Epoxy Resin | Hardener | $T_{cure}$ (° C.) | Time (hours) | Analysis |
|---|---|---|---|---|
| 144 BGOPB | 44 DDS | 130 | 4 | Thermal, chemical and physical |
| 144 BGOPB | 44 DDS | 150 | 4 | Thermal, chemical and physical |
| 144 BGOPB | 44 DDS | 180 | 4 | Thermal, chemical and physical |
| 144 BGOPB | 44 DDS | 177 | 12 | Thermal, chemical, physical, mechanical and fluid ingress |
| 133 BGOPB | 44 DDS | 130 | 4 | Thermal, chemical and physical |
| 133 BGOPB | 44 DDS | 150 | 4 | Thermal, chemical and physical |
| 133 BGOPB | 44 DDS | 180 | 4 | Thermal, chemical and physical |
| 133 BGOPB | 44 DDS | 177 | 12 | Thermal, chemical, physical, mechanical and fluid ingress |
| BisF | 44 DDS | 177 | 12 | Thermal (DMTA), physical, mechanical and fluid ingress |
| BisF | 33 DDS | 177 | 12 | Thermal (DMTA), physical, mechanical and fluid ingress |

Characterisation

Figure 25:
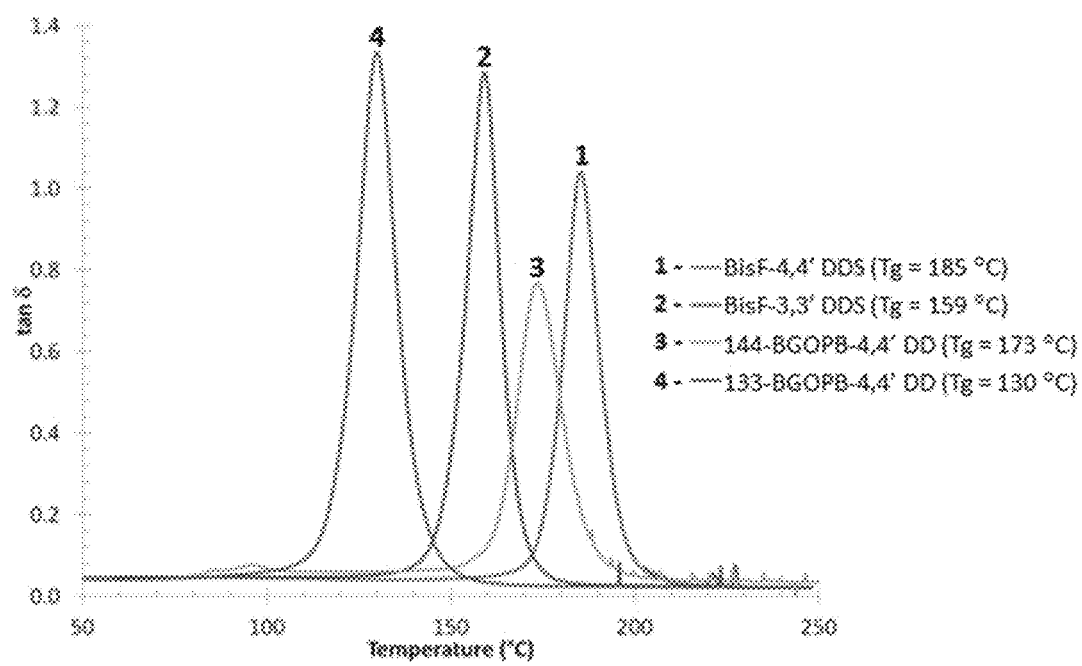
FIG. 25—Comparison of the tan δ spectra of 144-BGOPB and 133-BGOPB epoxy resins with BisF cured with 44 DDS and 33 DDS.

FIG. 25 shows a selection of raw tan δ traces for the 133 and 144 BGOPB systems after curing for 12 hours at 177° C. and compared against the widely used aerospace epoxy resin, BisF, cured under the same conditions, with 33 DDS and 44 DDS. As can be seen the 144 BGOPB polymer network has a Tg of only about 10° C. lower than the BisF/44 DDS network. In contrast, however, the 133 BGOPB/44 DDS cured polymer network is somewhat lower, of the order of 43° C. lower.

Figure 26:
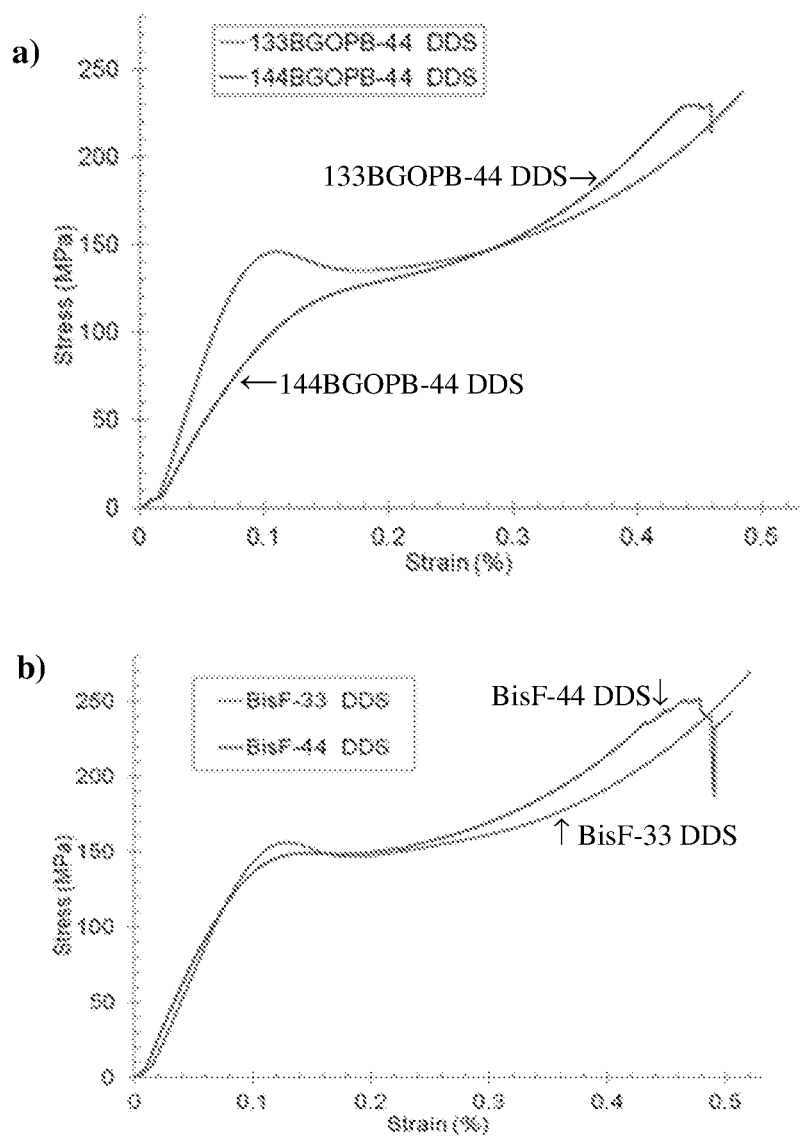
FIG. 26—Raw compressive strength versus strain for a) 144-BGOPB and 133-BGOPB cured networks compared with b) BisF cured with 44 DDS and 33 DDS.

FIG. 26 shows the raw compressive stress versus strain plots illustrating the differences in mechanical properties of the 133 and 144 BGOPB systems, particularly in relation to the extent of yield and the stiffness. The overall results are shown in Table 7. Important points to note are the low modulus of the 144 BGOPB (1239 MPa) in comparison with each other system, the next lowest being the BisF/4,4 DDS system at 1612 MPa. Despite this, the strain at yield for the 144 BGOPB network is significantly higher than the other resins, a key indicator of a networks capacity to act as a distortional resin. Beyond that, the 144 BGOPB has a lower yield stress, although it is likely that there is no significant trend with respect to stress. Failure stress and strain appear to be similar.

TABLE 7

Compressive mechanical properties of the 144-BGOPB and 133-BGOPB based polymer networks with BisF cured with 4,4 DDS and 3,3 DDS.

| System | Modulus/ GPa (Standard Deviation) | Yield Strain/% (Standard Deviation) | Yield Stress/ MPa (Standard Deviation) | Failure Strain/% (Standard Deviation) | Failure Strength/ MPa (Standard Deviation) |
|---|---|---|---|---|---|
| 144 BGOPB/ 44 DDS | 1239.02 (39.22) | 0.1780 (0.0201) | 122.87 (6.36) | 0.4377 (0.0180) | 225.69 (4.59) |
| 133 BGOPB/ 44 DDS | 2047.08 (118.21) | 0.1313 (0.0062) | 139.81 (1.36) | 0.4923 (0.0103) | 239.83 (2.78) |
| BisF/ 44 DDS | 1611.60 (112.35) | 0.1647 (0.0090) | 149.90 (1.49) | 0.4712 (0.0159) | 250.70 (2.60) |
| BisF/ 33 DDS | 1902.73 (110.90) | 0.1455 (0.0031) | 151.66 (2.93) | 0.5281 (0.0125) | 281.45 (12.58) |

It will be appreciated by persons skilled in the art that numerous variations and/or modifications can be made to the above-described examples, without departing from the broad general scope of the present disclosure. The present examples are, therefore, to be considered in all respects as illustrative and not restrictive.

The invention claimed is:

1. A compound of Formula 1a:

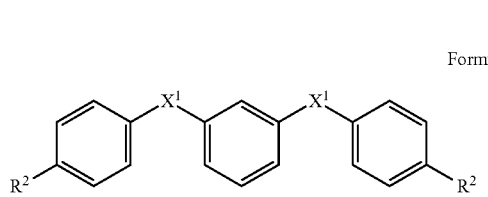
Formula 1a wherein each $X^1$ is C(O) and each $R^2$ is

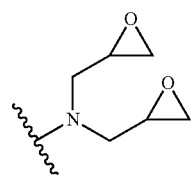

2. A formulation comprising the compound of claim 1 and a curing agent.

3. The formulation of claim 2, further comprising a compound of Formula 2a:

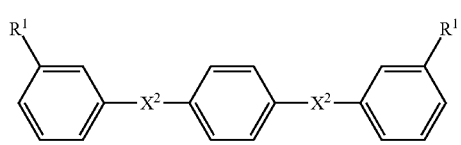
Formula 2a wherein each $X^2$ is C(O) and each $R^1$ is

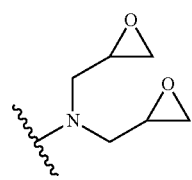

4. The formulation according to claim 2, wherein the curing agent is an aliphatic amine, cycloaliphatic amine, or an aromatic amine.

5. The formulation according to claim 2, wherein the curing agent is a diamine.

6. The formulation according to claim 5, wherein the diamine is represented by Formula 4:

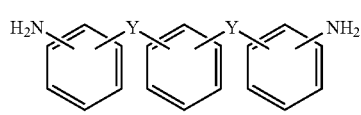
Formula 4 wherein each Y is the same and is O, $CH_2$, or C(O).

7. The formulation of claim 6, wherein the compound of Formula 4 is a compound of Formula 4a:

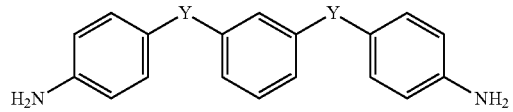
Formula 4a wherein each Y is the same and is O, $CH_2$, or C(O).

8. The formulation of claim 6, wherein the compound of Formula 4 is a compound of Formula 4b:

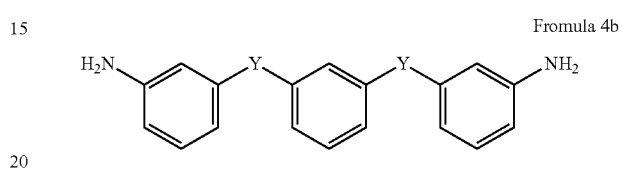
Fromula 4b wherein each Y is the same and is O, $CH_2$, or C(O).

9. The formulation of claim 6, wherein the compound of Formula 4 is a compound of Formula 4c:

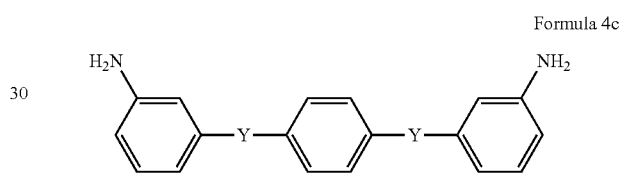
Formula 4c wherein each Y is the same and is O, $CH_2$, or C(O).

10. The formulation of claim 6, wherein the compound of Formula 4 is selected from a compound of Formula 4d:

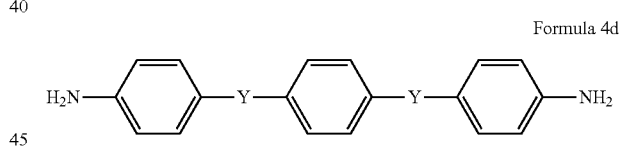
Formula 4d wherein each Y is the same and is O, $CH_2$, or C(O).

11. The formulation according to claim 2, further comprising one or more additives.

12. A composite material comprising a fibrous material and a cured epoxy resin, wherein the cured epoxy resin is formed from the formulation of claim 2.

13. A resin comprising the compound of claim 1 and a curing agent.

14. A compound of Formula 2a:

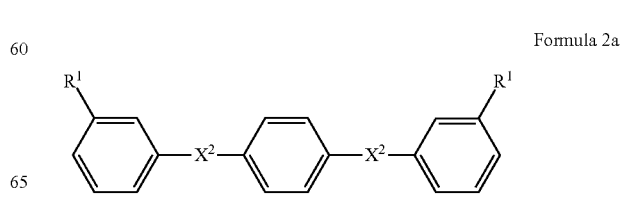
Formula 2a wherein each X² is C(O) and each R¹ is

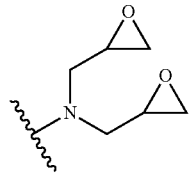
,

15. A formulation comprising the compound of claim 14 and a curing agent.

16. The formulation of claim 15, further comprising a compound of Formula 1a:

Fromula 1a

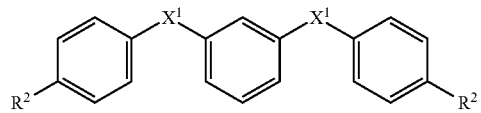

wherein each X¹ is C(O) and each R² is

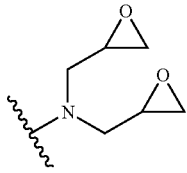
.

17. The formulation according to claim 15, wherein the curing agent is an aliphatic amine, cycloaliphatic amine, or an aromatic amine.

18. The formulation of claim 15, wherein the curing agent is a diamine.

19. The formulation according to claim 18, wherein the diamine is represented by Formula 4:

Formula 4

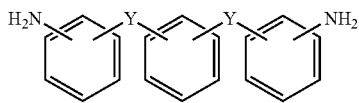

wherein each Y is the same and is O, CH₂, or C(O).

20. The formulation of claim 19, wherein the compound of Formula 4 is a compound of Formula 4a:

Formula 4a

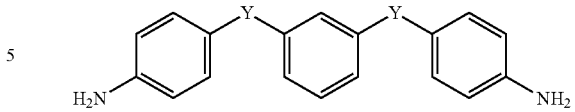

wherein each Y is the same and is O, CH₂, or C(O).

21. The formulation of claim 19, wherein the compound of Formula 4 is a compound of Formula 4b:

Fromula 4b

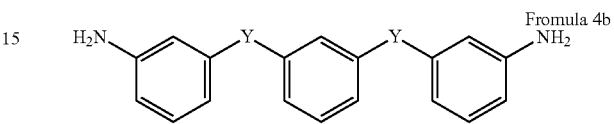

wherein each Y is the same and is O, CH₂, or C(O).

22. The formulation of claim 19, wherein the compound of Formula 4 is a compound of Formula 4c:

Formula 4c

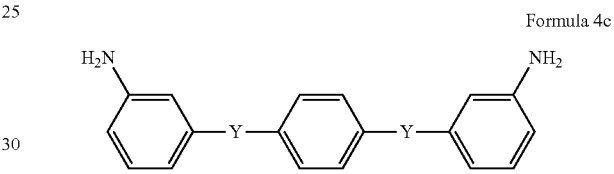

wherein each Y is the same and is O, CH₂, or C(O).

23. The formulation of claim 19, wherein the compound of Formula 4 is a compound of Formula 4d:

Formula 4d

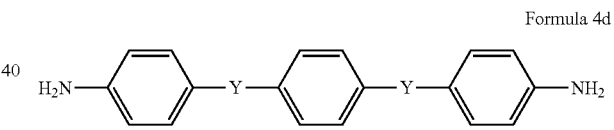

wherein each Y is the same and is O, CH₂, or C(O).

24. The formulation according to claim 15, further comprising one or more additives.

25. A composite material comprising a fibrous material and a cured epoxy resin, wherein the cured epoxy resin is formed from the formulation of claim 15.

26. A resin comprising the compound of claim 14 and a curing agent.

* * * * *

UNITED STATES PATENT AND TRADEMARK OFFICE
CERTIFICATE OF CORRECTION

PATENT NO. : 11,059,937 B2
APPLICATION NO. : 16/320403
DATED : July 13, 2021
INVENTOR(S) : Stephen Christensen et al.

Page 1 of 1

It is certified that error appears in the above-identified patent and that said Letters Patent is hereby corrected as shown below:

In the Specification

In Column 1, Line 7, delete "No" and insert -- No. --.

In Column 1, Line 10, delete "No" and insert -- No. --.

In the Claims

In Column 52, Line 15, in Claim 8, delete "Fromula 4b" and insert -- Formula 4b --.

In Column 53, Lines 2-10, in Claim 14, delete " 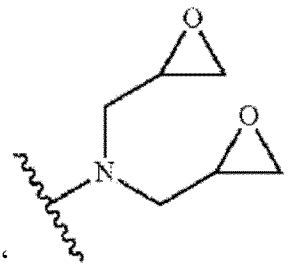 ' " and insert

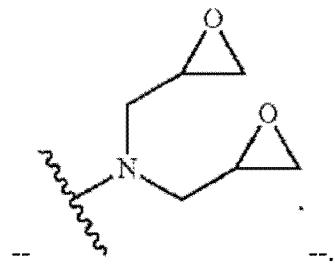

-- --.

In Column 53, Line 18, in Claim 16, delete "Fromula 1a" and insert -- Formula 1a --.

In Column 54, Line 14, in Claim 21, delete "Fromula 4b" and insert -- Formula 4b --.

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*